(12) United States Patent
Zergiebel

(10) Patent No.: US 8,336,556 B2
(45) Date of Patent: Dec. 25, 2012

(54) SURGICAL CLIP APPLIER AND METHOD OF ASSEMBLY

(75) Inventor: Earl M. Zergiebel, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/245,072

(22) Filed: Sep. 26, 2011

(65) Prior Publication Data
US 2012/0042497 A1 Feb. 23, 2012

Related U.S. Application Data

(63) Continuation of application No. 12/539,006, filed on Aug. 11, 2009, now Pat. No. 8,056,565.

(60) Provisional application No. 61/091,485, filed on Aug. 25, 2008.

(51) Int. Cl.
*B23P 11/00* (2006.01)

(52) U.S. Cl. ...................................................... 128/898

(58) Field of Classification Search ............... 227/175.1, 227/19; 29/428; 128/898
See application file for complete search history.

(56) References Cited

U.S. PATENT DOCUMENTS

| | | | |
|---|---|---|---|
| 3,120,230 A | 2/1964 | Skold | |
| 3,638,847 A | 2/1972 | Noiles et al. | |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,412,539 A | 11/1983 | Jarvik | |
| 4,471,780 A * | 9/1984 | Menges et al. | 606/143 |
| 4,478,220 A | 10/1984 | DiGiovanni et al. | |
| 4,480,640 A | 11/1984 | Becht | |
| 4,480,641 A | 11/1984 | Failla et al. | |
| 4,487,204 A | 12/1984 | Hrouda | |
| 4,487,205 A | 12/1984 | Di Giovanni et al. | |
| 4,491,133 A | 1/1985 | Menges et al. | |
| 4,492,232 A | 1/1985 | Green | |
| 4,498,476 A | 2/1985 | Cerwin et al. | |
| 4,500,024 A | 2/1985 | DiGiovanni et al. | |

(Continued)

FOREIGN PATENT DOCUMENTS

EP 0 085 931 A2 8/1983
(Continued)

OTHER PUBLICATIONS

European Search Report corresponding to European Application No. EP 05 80 2686.5, completed Jan. 9, 2012; mailed Jan. 18, 2012; (3 Pages).

(Continued)

*Primary Examiner* — Brian D Nash

(57) ABSTRACT

A method of assembling any one of a relatively small, medium and large clip applier for delivering relatively small, medium and large clips includes providing a housing for a handle assembly, selecting a channel assembly, connecting the channel assembly to the housing, providing a pusher bar in the selected channel assembly that extends to the handle assembly, and connecting a motion multiplier system to the pusher bar. The channel assembly is selected from a first channel assembly containing small surgical clips, a second channel assembly containing medium surgical clips, and a third channel assembly containing large surgical clips. Each channel assembly has an associated stroke length. The motion multiplier system varies the stroke of the pusher bar in accordance with the associated stroke length such that, upon firing, the pusher bar is translated the associated stroke length to load one of the clips into jaws of the clip applier.

10 Claims, 76 Drawing Sheets

U.S. PATENT DOCUMENTS

| | | |
|---|---|---|
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |

| | | | | | | |
|---|---|---|---|---|---|---|
| 5,527,319 A | 6/1996 | Green et al. | | 5,895,394 A | 4/1999 | Kienzle et al. |
| 5,527,320 A | 6/1996 | Carruthers et al. | | 5,897,565 A | 4/1999 | Foster |
| 5,542,949 A | 8/1996 | Yoon | | 5,904,693 A | 5/1999 | Dicesare et al. |
| 5,547,474 A | 8/1996 | Kloeckl et al. | | 5,913,862 A | 6/1999 | Ramsey et al. |
| 5,569,274 A | 10/1996 | Rapacki et al. | | 5,918,791 A | 7/1999 | Sorrentino et al. |
| 5,571,121 A | 11/1996 | Heifetz | | 5,921,996 A | 7/1999 | Sherman |
| 5,575,802 A | 11/1996 | McQuildin et al. | | 5,921,997 A | 7/1999 | Fogelberg et al. |
| 5,582,615 A | 12/1996 | Foshee et al. | | 5,928,251 A | 7/1999 | Aranyi et al. |
| 5,584,840 A | 12/1996 | Ramsey et al. | | 5,938,667 A | 8/1999 | Peyser et al. |
| 5,591,178 A | 1/1997 | Green et al. | | 5,951,574 A | 9/1999 | Stefanchik et al. |
| 5,593,414 A | 1/1997 | Shipp et al. | | 5,972,003 A | 10/1999 | Rousseau et al. |
| 5,593,421 A | 1/1997 | Bauer | | 5,976,159 A | 11/1999 | Bolduc et al. |
| 5,601,573 A | 2/1997 | Fogelberg et al. | | 5,993,465 A | 11/1999 | Shipp et al. |
| 5,601,574 A | 2/1997 | Stefanchik et al. | | 6,004,335 A | 12/1999 | Vaitekunas et al. |
| 5,607,436 A | 3/1997 | Pratt et al. | | 6,017,358 A | 1/2000 | Yoon et al. |
| 5,618,291 A | 4/1997 | Thompson et al. | | RE36,720 E | 5/2000 | Green et al. |
| 5,618,306 A | 4/1997 | Roth et al. | | 6,059,799 A | 5/2000 | Aranyi et al. |
| 5,620,452 A | 4/1997 | Yoon | | 6,099,536 A | 8/2000 | Petillo |
| 5,626,585 A | 5/1997 | Mittelstadt et al. | | 6,099,537 A | 8/2000 | Sugai et al. |
| 5,626,586 A | 5/1997 | Pistl et al. | | 6,139,555 A | 10/2000 | Hart et al. |
| 5,626,592 A | 5/1997 | Phillips et al. | | 6,210,418 B1 | 4/2001 | Storz et al. |
| 5,632,432 A | 5/1997 | Schulze et al. | | 6,217,590 B1 | 4/2001 | Levinson |
| RE35,525 E | 6/1997 | Stefanchik et al. | | 6,228,097 B1 | 5/2001 | Levinson et al. |
| 5,634,930 A | 6/1997 | Thornton et al. | | 6,241,740 B1 | 6/2001 | Davis et al. |
| 5,643,291 A | 7/1997 | Pier et al. | | 6,258,105 B1 | 7/2001 | Hart et al. |
| 5,645,551 A | 7/1997 | Green et al. | | 6,261,302 B1 | 7/2001 | Voegele et al. |
| 5,645,553 A | 7/1997 | Kolesa et al. | | 6,273,898 B1 | 8/2001 | Kienzle et al. |
| 5,649,937 A | 7/1997 | Bito et al. | | 6,277,131 B1 | 8/2001 | Kalikow |
| 5,653,720 A | 8/1997 | Johnson et al. | | 6,306,149 B1 | 10/2001 | Meade |
| 5,662,676 A | 9/1997 | Koninckx | | 6,318,619 B1 | 11/2001 | Lee |
| 5,662,679 A | 9/1997 | Voss et al. | | 6,322,571 B1 | 11/2001 | Adams |
| 5,665,097 A | 9/1997 | Baker et al. | | 6,350,269 B1 | 2/2002 | Shipp et al. |
| 5,676,676 A | 10/1997 | Porter | | 6,352,541 B1 | 3/2002 | Kienzle et al. |
| 5,681,330 A | 10/1997 | Hughett et al. | | 6,391,035 B1 | 5/2002 | Appleby et al. |
| 5,683,405 A | 11/1997 | Yacoubian et al. | | 6,423,079 B1 | 7/2002 | Blake, III |
| 5,695,502 A | 12/1997 | Pier et al. | | 6,428,548 B1 | 8/2002 | Durgin et al. |
| 5,695,505 A | 12/1997 | Yoon | | 6,440,144 B1 | 8/2002 | Bacher |
| 5,697,938 A | 12/1997 | Jensen et al. | | 6,461,363 B1 | 10/2002 | Gadberry et al. |
| 5,700,270 A | 12/1997 | Peyser et al. | | 6,464,710 B1 | 10/2002 | Foster |
| 5,700,271 A | 12/1997 | Whitfield et al. | | 6,494,886 B1 | 12/2002 | Wilk et al. |
| 5,702,048 A | 12/1997 | Eberlin | | 6,517,536 B2 | 2/2003 | Hooven et al. |
| 5,709,706 A | 1/1998 | Kienzle et al. | | 6,520,972 B2 | 2/2003 | Peters |
| 5,713,911 A | 2/1998 | Racenet et al. | | 6,527,786 B1 | 3/2003 | Davis et al. |
| 5,713,912 A | 2/1998 | Porter | | 6,537,289 B1 | 3/2003 | Kayan et al. |
| 5,720,756 A | 2/1998 | Green et al. | | 6,546,935 B2 | 4/2003 | Hooven |
| 5,722,982 A | 3/1998 | Ferreira et al. | | 6,551,333 B2 | 4/2003 | Kuhns et al. |
| 5,725,537 A | 3/1998 | Green et al. | | 6,569,171 B2 | 5/2003 | DeGuillebon et al. |
| 5,725,538 A | 3/1998 | Green et al. | | 6,579,304 B1 | 6/2003 | Hart et al. |
| 5,725,542 A | 3/1998 | Yoon | | 6,599,298 B1 | 7/2003 | Forster et al. |
| 5,728,110 A * | 3/1998 | Vidal et al. ............ 606/143 | | 6,602,252 B2 | 8/2003 | Mollenauer |
| 5,733,295 A | 3/1998 | Back et al. | | 6,607,540 B1 | 8/2003 | Shipp |
| 5,755,726 A | 5/1998 | Pratt et al. | | 6,613,060 B2 | 9/2003 | Adams et al. |
| 5,766,189 A | 6/1998 | Matsuno | | 6,626,916 B1 | 9/2003 | Yeung et al. |
| 5,769,857 A | 6/1998 | Reztzov et al. | | 6,626,922 B1 | 9/2003 | Hart et al. |
| 5,772,673 A | 6/1998 | Cuny et al. | | 6,648,898 B1 | 11/2003 | Baxter |
| 5,776,146 A | 7/1998 | Sackier et al. | | 6,652,538 B2 | 11/2003 | Kayan et al. |
| 5,776,147 A | 7/1998 | Dolendo | | 6,652,539 B2 | 11/2003 | Shipp et al. |
| 5,779,718 A | 7/1998 | Green et al. | | 6,673,083 B1 | 1/2004 | Kayan et al. |
| 5,779,720 A | 7/1998 | Walder-Utz et al. | | 6,676,659 B2 | 1/2004 | Hutchins et al. |
| 5,782,844 A | 7/1998 | Yoon et al. | | 6,679,894 B2 | 1/2004 | Damarati |
| 5,788,698 A | 8/1998 | Savornin | | RE38,445 E | 2/2004 | Pistl et al. |
| 5,792,149 A | 8/1998 | Sherts et al. | | 6,695,854 B1 | 2/2004 | Kayan et al. |
| 5,792,150 A | 8/1998 | Pratt et al. | | 6,706,057 B1 | 3/2004 | Bidoia et al. |
| 5,797,922 A | 8/1998 | Hessel et al. | | 6,716,226 B2 | 4/2004 | Sixto, Jr. et al. |
| 5,810,853 A | 9/1998 | Yoon | | 6,723,109 B2 | 4/2004 | Solingen |
| 5,817,116 A | 10/1998 | Takahashi et al. | | 6,743,240 B2 | 6/2004 | Smith et al. |
| 5,827,306 A | 10/1998 | Yoon | | 6,773,438 B1 | 8/2004 | Knodel et al. |
| 5,833,695 A | 11/1998 | Yoon | | 6,773,440 B2 | 8/2004 | Gannoe et al. |
| 5,833,696 A | 11/1998 | Whitfield et al. | | 6,776,783 B1 | 8/2004 | Frantzen et al. |
| 5,833,700 A | 11/1998 | Fogelberg et al. | | 6,776,784 B2 | 8/2004 | Ginn |
| 5,843,097 A | 12/1998 | Mayenberger et al. | | 6,780,195 B2 | 8/2004 | Porat |
| 5,843,101 A | 12/1998 | Fry | | 6,793,663 B2 | 9/2004 | Kneifel et al. |
| 5,846,255 A | 12/1998 | Casey | | 6,793,664 B2 | 9/2004 | Mazzocchi et al. |
| 5,849,019 A | 12/1998 | Yoon | | 6,802,848 B2 | 10/2004 | Anderson et al. |
| 5,858,018 A | 1/1999 | Shipp et al. | | 6,814,742 B2 | 11/2004 | Kimura et al. |
| 5,861,005 A | 1/1999 | Kontos | | 6,818,009 B2 | 11/2004 | Hart et al. |
| 5,868,759 A | 2/1999 | Peyser et al. | | 6,821,273 B2 | 11/2004 | Mollenauer |
| 5,868,761 A | 2/1999 | Nicholas et al. | | 6,821,284 B2 | 11/2004 | Sturtz et al. |
| 5,876,410 A | 3/1999 | Petillo | | 6,824,547 B2 | 11/2004 | Wilson, Jr. et al. |

| | | | | | |
|---|---|---|---|---|---|
| 6,824,548 B2 | 11/2004 | Smith et al. | 2001/0047178 A1 | 11/2001 | Peters |
| 6,835,199 B2 | 12/2004 | McGuckin, Jr. et al. | 2002/0068947 A1 | 6/2002 | Kuhns et al. |
| 6,835,200 B2 | 12/2004 | Laufer et al. | 2002/0082618 A1 | 6/2002 | Shipp et al. |
| 6,837,893 B2 | 1/2005 | Miller | 2002/0087169 A1 | 7/2002 | Brock et al. |
| 6,837,894 B2 | 1/2005 | Pugsley, Jr. et al. | 2002/0087170 A1 | 7/2002 | Kuhns et al. |
| 6,837,895 B2 | 1/2005 | Mayenberger | 2002/0099388 A1 | 7/2002 | Mayenberger |
| 6,840,945 B2 | 1/2005 | Manetakis et al. | 2002/0120279 A1 | 8/2002 | Deguillebon et al. |
| 6,843,794 B2 | 1/2005 | Sixto, Jr. et al. | 2002/0128668 A1 | 9/2002 | Manetakis et al. |
| 6,849,078 B2 | 2/2005 | Durgin et al. | 2002/0177859 A1 | 11/2002 | Monassevitch et al. |
| 6,849,079 B1 | 2/2005 | Blake, III et al. | 2002/0198537 A1 | 12/2002 | Smith et al. |
| 6,853,879 B2 | 2/2005 | Sunaoshi | 2002/0198538 A1 | 12/2002 | Kortenbach et al. |
| 6,869,435 B2 | 3/2005 | Blake, III | 2002/0198539 A1 | 12/2002 | Sixto, Jr. et al. |
| 6,869,436 B2 | 3/2005 | Wendlandt | 2002/0198540 A1 | 12/2002 | Smith et al. |
| 6,889,116 B2 | 5/2005 | Jinno | 2002/0198541 A1 | 12/2002 | Smith et al. |
| 6,896,682 B1 | 5/2005 | McClellan et al. | 2003/0014060 A1 | 1/2003 | Wilson, Jr. et al. |
| 6,905,503 B2 | 6/2005 | Gifford, III et al. | 2003/0018345 A1 | 1/2003 | Green |
| 6,911,032 B2 | 6/2005 | Jugenheimer et al. | 2003/0023249 A1 | 1/2003 | Manetakis |
| 6,911,033 B2 | 6/2005 | de Guillebon et al. | 2003/0040759 A1 | 2/2003 | de Guillebon et al. |
| 6,913,607 B2 | 7/2005 | Ainsworth et al. | 2003/0105476 A1 | 6/2003 | Sancoff et al. |
| 6,916,327 B2 | 7/2005 | Northrup, III et al. | 2003/0114867 A1 | 6/2003 | Bolduc et al. |
| 6,923,818 B2 | 8/2005 | Muramatsu et al. | 2003/0135224 A1 | 7/2003 | Blake, III |
| 6,939,356 B2 | 9/2005 | Debbas | 2003/0167063 A1 | 9/2003 | Kerr |
| 6,942,674 B2 | 9/2005 | Belef et al. | 2003/0225423 A1 | 12/2003 | Huitema |
| 6,942,676 B2 | 9/2005 | Buelna | 2003/0233105 A1 | 12/2003 | Gayton |
| 6,945,978 B1 | 9/2005 | Hyde | 2004/0010272 A1 | 1/2004 | Manetakis et al. |
| 6,945,979 B2 | 9/2005 | Kortenbach et al. | 2004/0097970 A1 | 5/2004 | Hughett |
| 6,949,107 B2 | 9/2005 | McGuckin, Jr. et al. | 2004/0097971 A1 | 5/2004 | Hughett |
| 6,953,465 B2 | 10/2005 | Dieck et al. | 2004/0138681 A1 | 7/2004 | Pier |
| 6,955,643 B2 | 10/2005 | Gellman et al. | 2004/0153100 A1 | 8/2004 | Ahlberg et al. |
| 6,959,852 B2 | 11/2005 | Shelton, IV et al. | 2005/0080440 A1 | 4/2005 | Durgin et al. |
| 6,960,218 B2 | 11/2005 | Rennich | 2005/0085830 A1 | 4/2005 | Lehman et al. |
| 6,960,221 B2 | 11/2005 | Ho et al. | 2005/0090837 A1 | 4/2005 | Sixto, Jr. et al. |
| 6,962,594 B1 | 11/2005 | Thevenet | 2005/0090838 A1 | 4/2005 | Sixto, Jr. et al. |
| 6,963,792 B1 | 11/2005 | Green | 2005/0096670 A1 | 5/2005 | Wellman et al. |
| 6,964,363 B2 | 11/2005 | Wales et al. | 2005/0096671 A1 | 5/2005 | Wellman et al. |
| 6,964,668 B2 | 11/2005 | Modesitt et al. | 2005/0096672 A1 | 5/2005 | Manetakis et al. |
| 6,966,875 B1 | 11/2005 | Longobardi | 2005/0101975 A1 | 5/2005 | Nguyen et al. |
| 6,966,917 B1 | 11/2005 | Suyker et al. | 2005/0107807 A1 | 5/2005 | Nakao |
| 6,966,919 B2 | 11/2005 | Sixto, Jr. et al. | 2005/0107809 A1 | 5/2005 | Litscher et al. |
| 6,969,391 B1 | 11/2005 | Gazzani | 2005/0107810 A1 | 5/2005 | Morales et al. |
| 6,972,023 B2 | 12/2005 | Whayne et al. | 2005/0107811 A1 | 5/2005 | Starksen et al. |
| 6,972,027 B2 | 12/2005 | Fallin et al. | 2005/0107812 A1 | 5/2005 | Starksen et al. |
| 6,973,770 B2 | 12/2005 | Schnipke et al. | 2005/0107871 A1 | 5/2005 | Realyvasquez et al. |
| 6,974,462 B2 | 12/2005 | Sater | 2005/0113847 A1 | 5/2005 | Gadberry et al. |
| 6,974,466 B2 | 12/2005 | Ahmed et al. | 2005/0119671 A1 | 6/2005 | Reydel et al. |
| 6,974,475 B1 | 12/2005 | Wall | 2005/0119673 A1 | 6/2005 | Gordon et al. |
| 6,981,505 B2 | 1/2006 | Krause et al. | 2005/0119677 A1 | 6/2005 | Shipp |
| 6,981,628 B2 | 1/2006 | Wales | 2005/0125010 A1 | 6/2005 | Smith et al. |
| 6,991,635 B2 | 1/2006 | Takamoto et al. | 2005/0143767 A1 | 6/2005 | Kimura et al. |
| 7,044,353 B2 * | 5/2006 | Mastri et al. ............... 227/176.1 | 2005/0149063 A1 | 7/2005 | Young et al. |
| 7,052,504 B2 | 5/2006 | Hughett | 2005/0149064 A1 | 7/2005 | Peterson et al. |
| 7,056,330 B2 | 6/2006 | Gayton | 2005/0149068 A1 | 7/2005 | Williams et al. |
| 7,108,703 B2 | 9/2006 | Danitz et al. | 2005/0149069 A1 | 7/2005 | Bertolero et al. |
| 7,144,402 B2 | 12/2006 | Kuester, III | 2005/0165415 A1 | 7/2005 | Wales |
| 7,175,648 B2 | 2/2007 | Nakao | 2005/0165418 A1 | 7/2005 | Chan |
| 7,179,265 B2 | 2/2007 | Manetakis et al. | 2005/0171560 A1 | 8/2005 | Hughett |
| 7,207,997 B2 | 4/2007 | Shipp et al. | 2005/0173490 A1 | 8/2005 | Shelton |
| 7,211,091 B2 | 5/2007 | Fowler et al. | 2005/0177176 A1 | 8/2005 | Gerbi et al. |
| 7,211,092 B2 | 5/2007 | Hughett | 2005/0177177 A1 | 8/2005 | Viola |
| 7,214,230 B2 | 5/2007 | Brock et al. | 2005/0203547 A1 | 9/2005 | Weller et al. |
| 7,214,232 B2 | 5/2007 | Bowman et al. | 2005/0203548 A1 | 9/2005 | Weller et al. |
| 7,220,266 B2 * | 5/2007 | Gambale ...................... 606/144 | 2005/0216036 A1 | 9/2005 | Nakao |
| 7,223,271 B2 | 5/2007 | Muramatsu et al. | 2005/0216056 A1 | 9/2005 | Valdevit et al. |
| 7,223,272 B2 | 5/2007 | Francese et al. | 2005/0222588 A1 | 10/2005 | Vandenbroek et al. |
| 7,232,445 B2 | 6/2007 | Kortenbach et al. | 2005/0222590 A1 | 10/2005 | Gadberry et al. |
| 7,261,724 B2 | 8/2007 | Molitor et al. | 2005/0222665 A1 | 10/2005 | Aranyi |
| 7,261,725 B2 | 8/2007 | Binmoeller | 2005/0228411 A1 | 10/2005 | Manzo |
| 7,264,625 B1 | 9/2007 | Buncke | 2005/0228416 A1 | 10/2005 | Burbank et al. |
| 7,288,098 B2 | 10/2007 | Huitema et al. | 2005/0234478 A1 | 10/2005 | Wixey et al. |
| 7,297,149 B2 | 11/2007 | Vitali et al. | 2005/0251183 A1 | 11/2005 | Buckman et al. |
| 7,316,693 B2 | 1/2008 | Viola | 2005/0251184 A1 | 11/2005 | Anderson |
| 7,316,696 B2 | 1/2008 | Wilson, Jr. et al. | 2005/0256529 A1 | 11/2005 | Yawata et al. |
| 7,326,223 B2 | 2/2008 | Wilson, Jr. | 2005/0267495 A1 | 12/2005 | Ginn et al. |
| 7,329,266 B2 | 2/2008 | Royse et al. | 2005/0273122 A1 | 12/2005 | Theroux et al. |
| 7,331,968 B2 | 2/2008 | Arp et al. | 2005/0277951 A1 | 12/2005 | Smith et al. |
| 7,338,503 B2 | 3/2008 | Rosenberg et al. | 2005/0277952 A1 | 12/2005 | Arp et al. |
| 7,357,287 B2 | 4/2008 | Shelton et al. | 2005/0277953 A1 | 12/2005 | Francese et al. |
| 7,357,805 B2 | 4/2008 | Masuda et al. | 2005/0277954 A1 | 12/2005 | Smith et al. |
| 7,673,781 B2 | 3/2010 | Swayze et al. | 2005/0277955 A1 | 12/2005 | Palmer et al. |

| | | |
|---|---|---|
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Rosenberg et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149788 A1 | 6/2007 | Michler et al. |
| 2007/0149989 A1 | 6/2007 | Santili et al. |
| 2007/0162060 A1 | 7/2007 | Wild |
| 2007/0175956 A1 | 8/2007 | Swayze et al. |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0246508 A1* | 10/2007 | Green ........................ 227/180.1 |
| 2007/0250080 A1 | 10/2007 | Jones et al. |
| 2007/0262116 A1 | 11/2007 | Hueil et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0243145 A1 | 10/2008 | Whitfield et al. |
| 2009/0299382 A1* | 12/2009 | Zergiebel ...................... 606/142 |

FOREIGN PATENT DOCUMENTS

| | | |
|---|---|---|
| EP | 0 089 737 A1 | 9/1983 |
| EP | 0 324 166 A2 | 7/1989 |
| EP | 0 392 750 A1 | 10/1990 |
| EP | 0 409 569 A1 | 1/1991 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 191 A2 | 10/2006 |
| EP | 1 813 199 A1 | 8/2007 |
| EP | 1 908 423 A2 | 4/2008 |
| EP | 1 913 881 A1 | 4/2008 |
| EP | 2 229 895 A1 | 9/2010 |
| JP | 2003 033361 A | 2/2003 |
| WO | WO 2005/091457 A1 | 9/2005 |
| WO | WO 2006/042076 A2 | 4/2006 |
| WO | WO 2006/042084 A2 | 4/2006 |
| WO | WO 2006/042110 A2 | 4/2006 |
| WO | WO 2008/118928 A2 | 10/2008 |
| WO | WO 2008/127968 A2 | 10/2008 |

OTHER PUBLICATIONS

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

The extended International Search Report corresponding to European Application No. 07 25 3905.9, completed Jan. 29, 2008; mailed Feb. 7, 2008; (7 Pages).

The partial International Search Report corresponding to European Application No. EP 07 25 3807.7, completed Jul. 23, 2008; mailed Aug. 1, 2008; (3 Pages).

International Search Report corresponding to International Application No. PCT/US08/58185, completed Sep. 4, 2008; mailed Sep. 9, 2008; (2 Pages).

The International Search Report corresponding to International Application No. PCT/US08/59859, completed Sep. 14, 2008; mailed Sep. 18, 2008; (2 Pages).

The extended European Search Report corresponding to European Application No. EP 07 25 3807.7, completed Nov. 7, 2008; mailed Nov. 26, 2008; (11 Pages).

The extended European Search Report corresponding to European Application No. EP 09252049.3, completed Dec. 11, 2009; mailed Jan. 12, 2010; (3 Pages).

The extended European Search Report corresponding to European Application No. EP 09252050.1, completed Dec. 23, 2009; mailed Jan. 21, 2010; (3 Pages).

The extended European Search Report corresponding to European Application No. EP 09252051.9, completed Dec. 21, 2009; mailed Jan. 28, 2010; (3 Pages).

The extended European Search Report corresponding to European Application No. EP 09252052.7, completed Nov. 16, 2009; mailed Nov. 24, 2009; (3 Pages).

The extended European Search Report corresponding to European Application No. EP 09252053.5, completed Nov. 24, 2009; mailed Dec. 1, 2009; (3 Pages).

The extended European Search Report corresponding to European Application No. EP 09252054.3, completed Jan. 7, 2010; mailed Jan. 22, 2010; (3 Pages).

Extended European Search Report corresponding to European Application No. EP 09252056.8, completed Jan. 8, 2010; mailed Feb. 5, 2010; (3 Pages).

Extended European Search Report corresponding to European Application No. EP 10250497.4, completed May 4, 2010; mailed May 12, 2010; (6 Pages).

Extended European Search Report corresponding to European Application No. EP 10252079.8, completed Mar. 8, 2011; mailed Mar. 17, 2011; (3 Pages).

Extended European Search Report corresponding to European Application No. EP 11002681.2, completed May 31, 2011; mailed Jun. 10, 2011; (3 Pages).

European Search Report corresponding to European Application No. EP 05810218.7, completed Apr. 18, 2011; mailed May 20, 2011; (3 pages).

European Search Report corresponding to European Application No. EP 05807612.6, completed May 2, 2011; mailed May 20, 2011; (3 pages).

Extended European Search Report corresponding to European Application No. EP 10251737.2, completed May 9, 2011; mailed May 20, 2011; (4 pages).

"Salute II Disposable Fixation Device", Technique Guide—Laparoscopic and Open Inguinal and Ventral Hernia Repair; Davol, A Bard Company, 2006; (7 Pages).

The extended European Search Report corresponding to European Application No. EP 11250214.1, completed May 25, 2011; mailed Jun. 1, 2011; (3 Pages).

\* cited by examiner

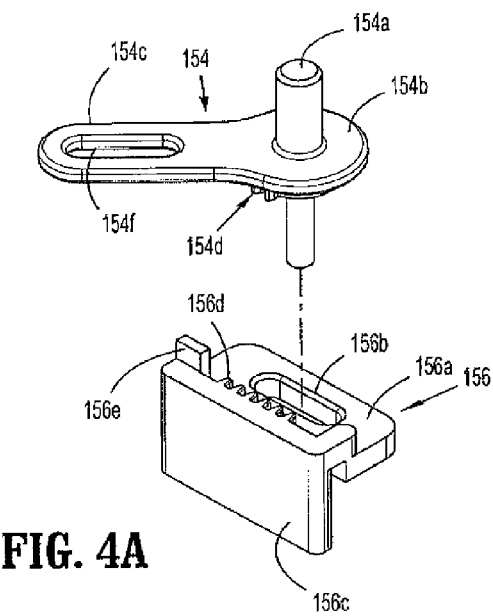
FIG. 4A
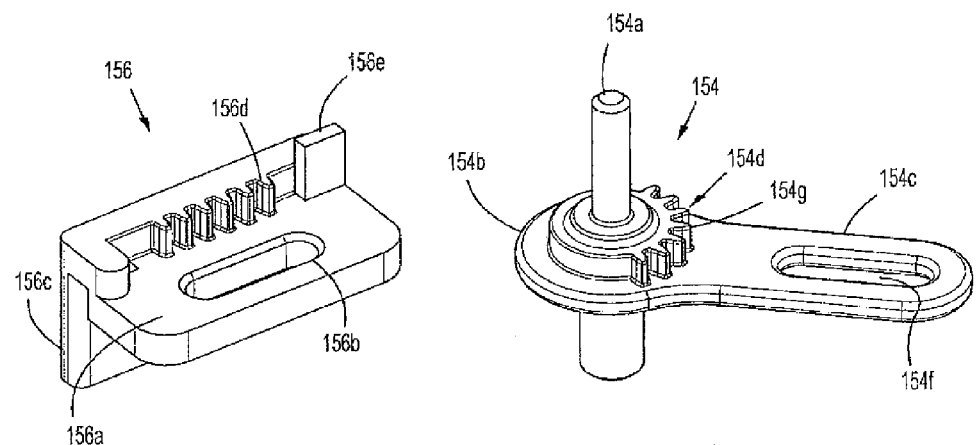
FIG. 4B  FIG. 4C

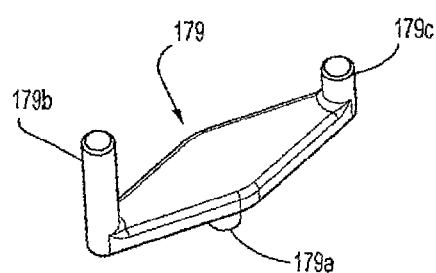
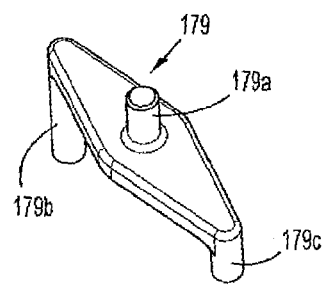
FIG. 4D  FIG. 4E
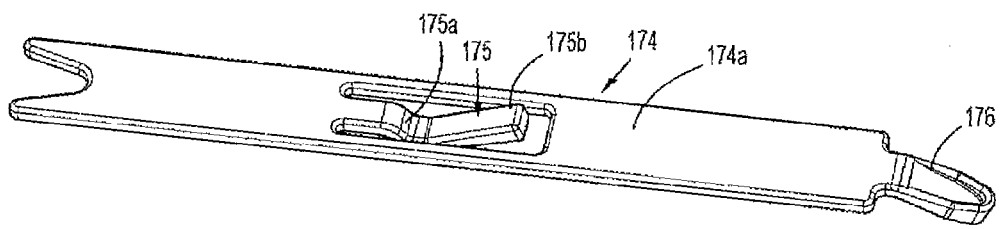
FIG. 4F
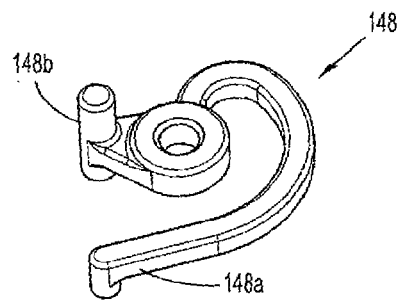
FIG. 4G
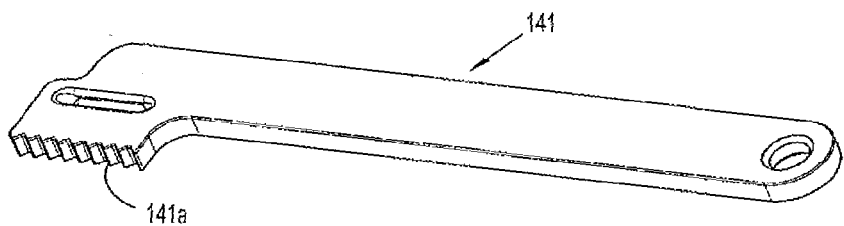
FIG. 4H

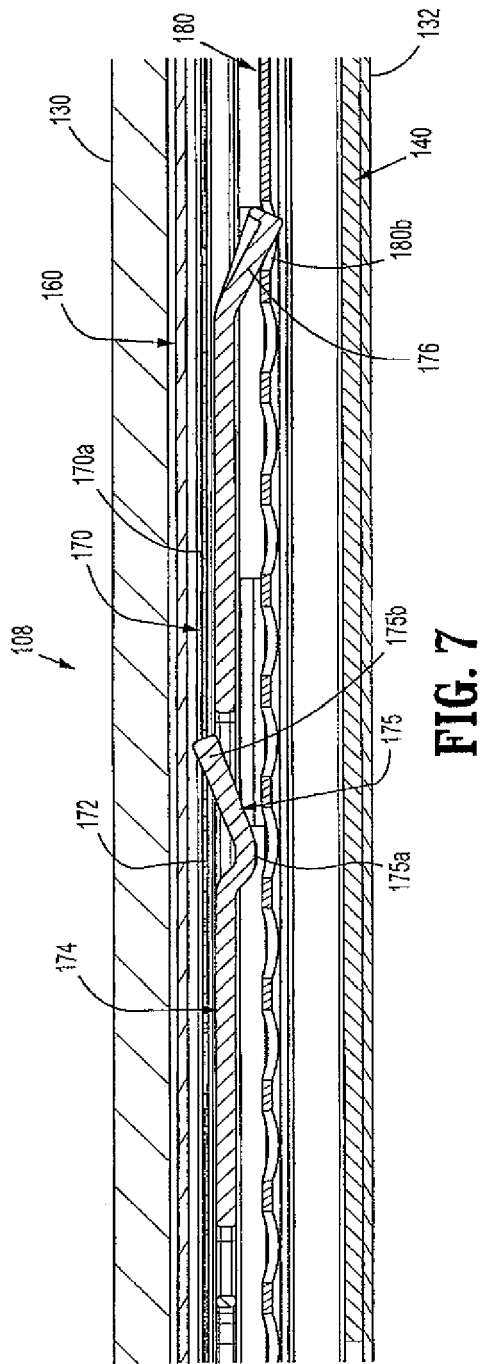
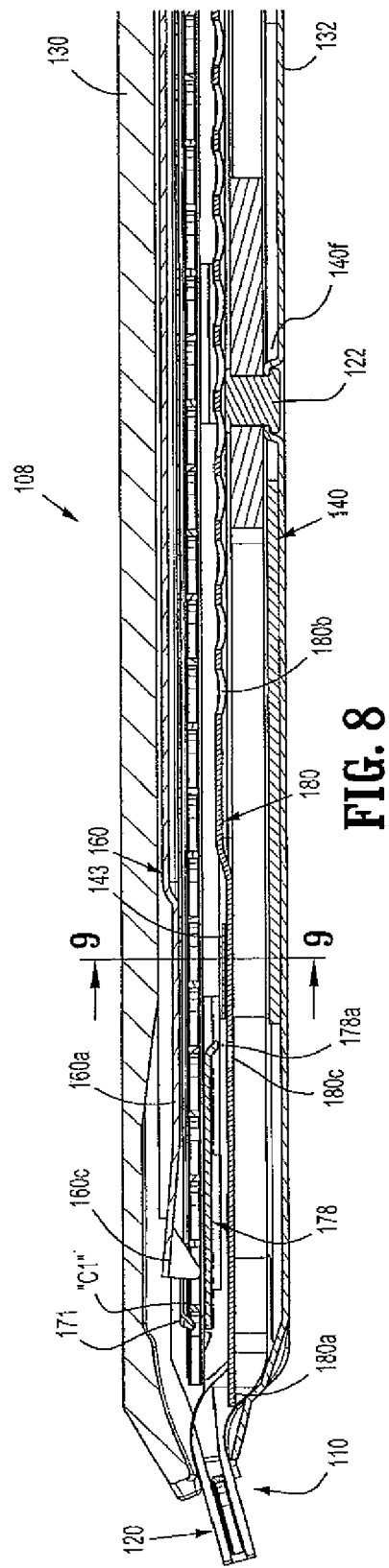
FIG. 7
FIG. 8

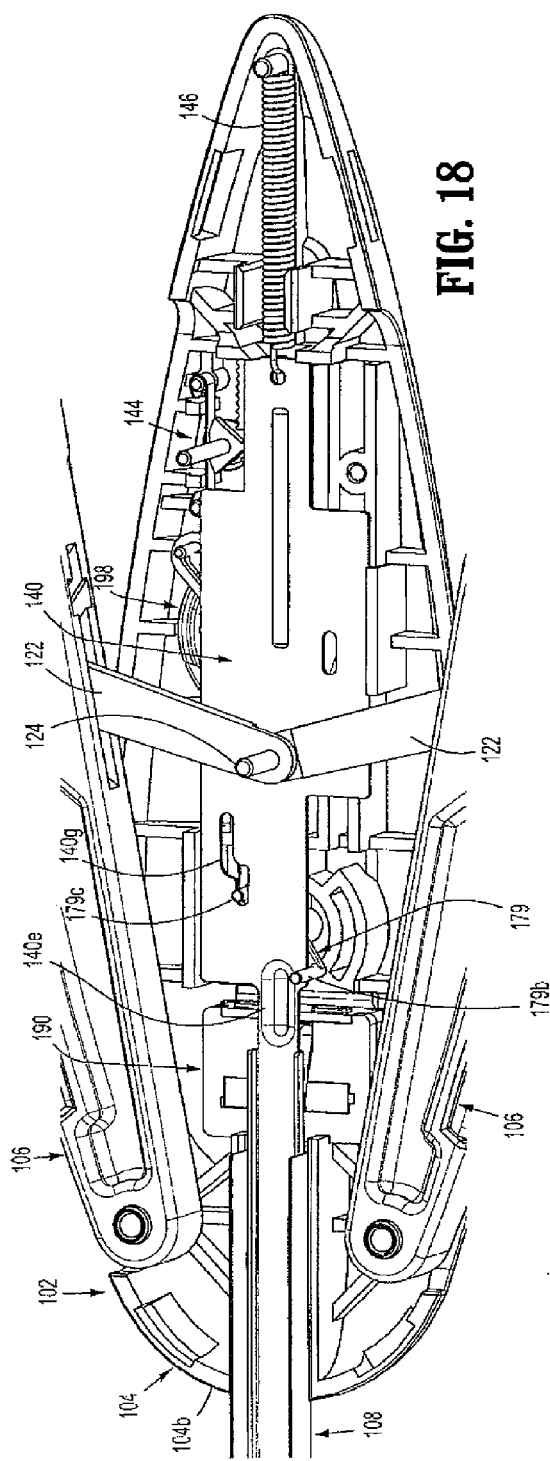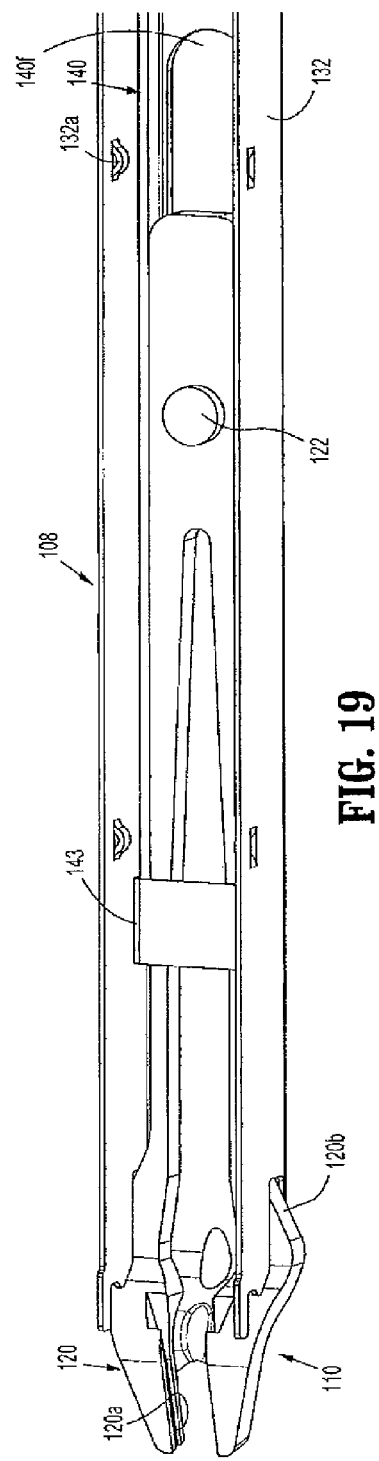

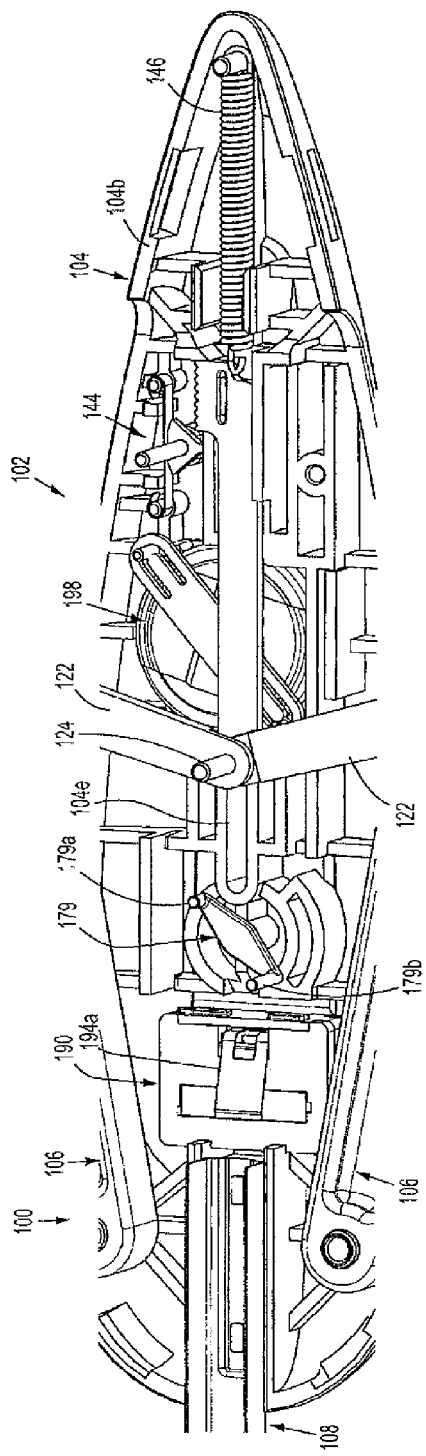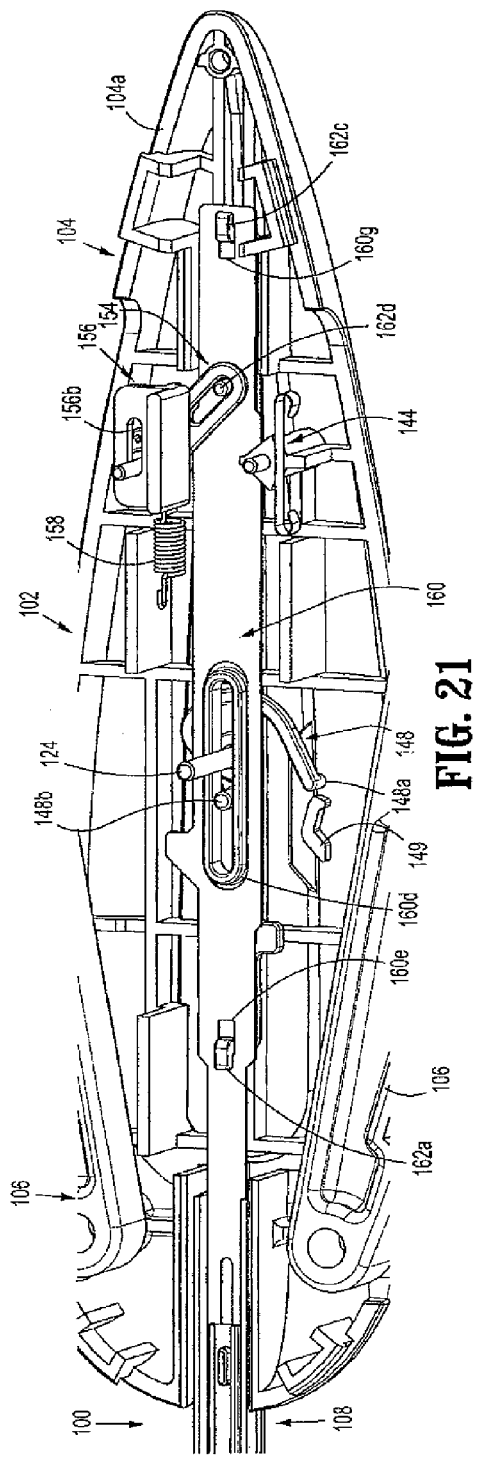

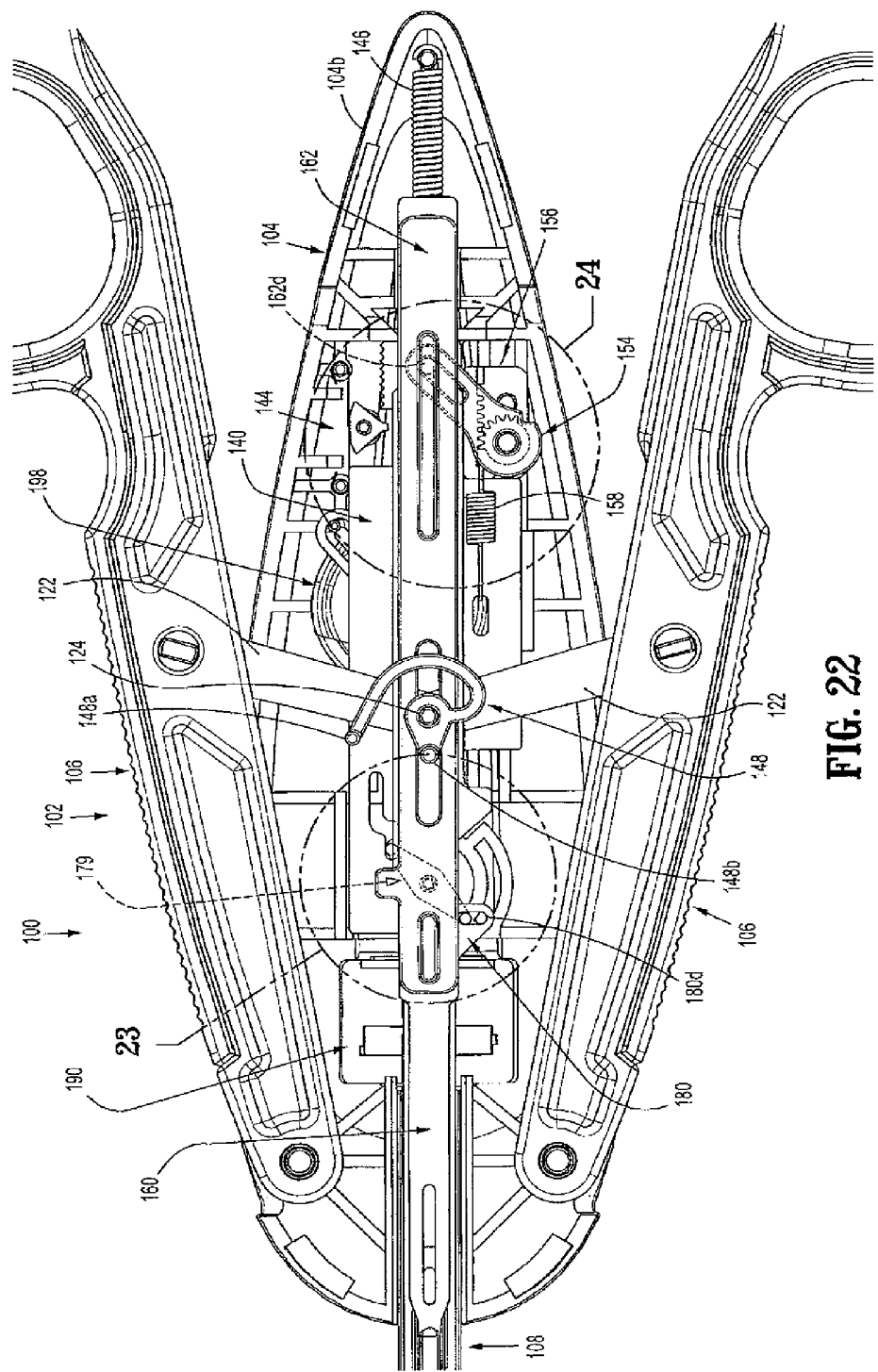

SURGICAL CLIP APPLIER AND METHOD OF ASSEMBLY

CROSS REFERENCE TO RELATED APPLICATION

The present application is a continuation application of U.S. application Ser. No. 12/539,006, filed Aug. 11, 2009, now U.S. Pat. No. 8,056,565, which claims the benefit of and priority to U.S. Provisional Application Ser. No. 61/091,485, filed on Aug. 25, 2008, the entire content of which are incorporated herein by reference.

BACKGROUND

1. Technical Field

The present application relates to surgical instruments and their methods of assembly, and more particularly, to surgical clip appliers having a plurality of clips for applying the clips to body tissues and vessels during surgical procedures and their methods of assembly.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Surgical clip appliers are typically available in a variety of sizes and/or scales ranging from relatively small, relatively medium to relatively large. Generally, each particular size of surgical clip appliers includes different components. As such, the method of assembling the various sized surgical clip appliers differs from one size to another.

As a consequence, the technicians must be taught different routines and procedures for assembling the various sized surgical clip appliers. As a result, errors in the assembling of the various sized surgical clip appliers may occur on an elevated level as the technicians' mistake the assembly procedure of one sized surgical clip applier for the assembly procedure of another sized surgical clip applier.

The need therefore exists for a family of different sized instruments for applying surgical clips which may be assembled in the same manner from one size to another size.

Also, a need exists for a uniform method of assembling each of the different sized instruments in order to improve the efficiency of production.

SUMMARY

The present application relates to surgical clip appliers having a plurality of clips for applying the clips to body tissues and vessels during surgical procedures and their methods of assembly.

According to an aspect of the present disclosure, a surgical clip applier is provided including a housing; at least one handle pivotably connected to the housing; a channel assembly extending from the housing; a clip carrier disposed within said channel assembly and defining a channel and a plurality of windows therein; a plurality of clips slidably disposed within said channel of said clip carrier; a wedge plate reciprocally disposed within said channel assembly, said wedge plate being operatively connected to said handles and including a plurality of apertures formed along a length thereof; and a clip follower slidably disposed within said channel of said clip carrier at a location proximal of said plurality of clips, said clip follower being configured and adapted for selective engagement with said windows of said clip carrier and said apertures of said wedge plate. The clip follower is configured and adapted to distally urge said plurality of clips relative to said clip carrier upon reciprocal movement of said wedge plate.

The clip follower may be configured to engage the wedge plate and move distally upon distal translation of the wedge plate, and may be configured to engage the clip carrier and stop proximal movement thereof upon proximal translation of the wedge plate.

The clip applier may further include a jaw assembly including a pair of jaws extending from an end of said channel assembly, opposite said housing. The jaw assembly may be adapted to accommodate a clip therein and may be operable to effect formation of a clip in response to movement of said handles.

The clip applier may further include a clip pusher bar reciprocally positioned within at least one of said housing and said channel assembly. The pusher bar may have a first end operatively connected to said at least one handle and a second end defining a pusher. The pusher bar may be movable towards said jaws as said at least one handle is moved in a first direction by an initial amount in order to move a distal-most clip between said jaws. The pusher bar may be configured and adapted to move towards said housing as said at least one handle is moved an additional amount in said first direction to move said pusher behind a distal-most clip in said plurality of clips.

The clip applier may further include a motion multiplier system configured to distally move the pusher bar by an incremental amount upon an initial actuation of the handles, and configured to proximally move the pusher bar and the wedge plate subsequent to the initial actuation of the handles.

The clip applier may still further include a drive channel translatably slidably disposed within at least one of said housing and said channel assembly. The drive channel may have a first end operatively connected to at least one of said handles and a second end configured and dimensioned to selectively engage said pair of jaws to effectuate closure of said pair of jaws. The drive channel may be moved towards said jaw assembly as said handles are actuated in a first direction to move said second end thereof against said jaws to close said jaws. The drive channel may be moved away from said jaws as said handles are moved in a second direction to move said second end thereof away from said jaws to allow said jaws to open.

The clip applier may further include a pivot arm operatively connected to said wedge plate and said drive channel. Rotation of said pivot arm, during distal movement of said drive channel, may result in proximal movement of said wedge plate.

The clip applier may further include a motion multiplier system having a bell crank gear pivotally supported in the housing and pivotally connected to the pusher bar; an accelerator rack slidably supported in the housing and operatively joined to the bell crank gear; and a biasing member interconnecting the drive channel and the accelerator rack. A distal translation of the drive channel may cause distal translation of the accelerator rack via the biasing member. Distal translation of the accelerator rack may cause a first rotation of the bell crank gear and distal translation of the pusher bar.

The bell crank gear may include an arm extending radially therefrom and an elongate slot formed in the arm, wherein the elongate slot slidably receives a boss operatively associated with the pusher bar.

The clip applier may further include a motion reversing mechanism operatively connected to said drive channel and said wedge plate and selectively engageable with said pusher bar. Rotation of said motion reversing mechanism, during said distal translation of said drive channel, may result in proximal movement of said wedge plate and said pusher bar.

The clip applier may further comprise a ratchet mechanism including a rack, having a plurality of ratchet teeth, associated with said drive channel; and a pawl, having at least one tooth, disposed at a location to selectively engage said rack. The pawl may be biased into engagement with said rack. As said drive channel is longitudinally reciprocated, said plurality of teeth may be passed over said pawl. The pawl may prevent inadvertent return of said drive channel before full actuation of said at least one handle.

The clip applier may further include a lockout disposed in a distal end of said channel assembly. The lockout may be actuated by said clip follower when a last clip is expelled from said clip applier. The lockout may be urged by said clip follower to extend across a path of said drive channel, thereby preventing said drive channel from moving distally.

The clip applier may further include a counter mechanism supported in at least one of said housing and said channel assembly. The counter mechanism may be configured and adapted to display a change in said clip applier upon each actuation of said handles.

The drive channel may be configured and dimensioned to at least partially surround said jaws and said wedge plate. The drive channel may include a strap extending across a distal end thereof for maintaining said jaws and said wedge plate within said drive channel.

According to another aspect of the present disclosure, a surgical clip applier is provided including a housing; at least one handle pivotably connected to opposite sides of the housing; a channel assembly fixed to and extending from the housing; a pair of jaws supported on and extending from a distal end of the channel assembly; a clip carrier disposed within said channel assembly and defining a channel; a plurality of clips slidably disposed within said channel of said clip carrier; a clip follower slidably disposed within said channel of said clip carrier at a location proximal of said plurality of clips; a drive channel translatably disposed within at least one of said housing and said channel assembly, said drive channel having a first end operatively connected to at least one of said handles and a second end configured and dimensioned to selectively engage said pair of jaws to effectuate closure thereof; a pusher bar translatably disposed within at least one of said housing and said channel assembly, said pusher bar being connected to said drive channel via a motion multiplier system, a distal end of said pusher bar being configured to engage a distal-most clip of the plurality of clips; a wedge plate reciprocally disposed within at least one of said housing and said channel assembly, wherein a distal end of said wedge plate is selectively insertable between said pair of jaws; and a motion reversing mechanism including a first end connected to said drive channel, and a second end connected to said wedge plate and engageable by said pusher bar. In use, distal translation of said drive channel causes said pusher bar to translate distally via said motion multiplier system; and distal translation of said drive channel causes said pusher bar and said wedge plate to translate proximally, via said motion reversing mechanism, following a dwell period.

The wedge plate may define a plurality of apertures formed along a length thereof. The clip carrier may define a plurality of windows formed along a length thereof. The clip follower may be configured and adapted for selective engagement with said windows of said clip carrier and said apertures of said wedge plate. The clip follower may be configured and adapted to distally incrementally urge said plurality of clips relative to said clip carrier upon a distal advancement of said wedge plate.

The clip applier may further include an indicator configured to create at least one of an audible indication and a tactile indication upon at least one of a loading of a clip into said pair of jaws and a formation of a clip by said pair of jaws.

The motion multiplier system may include an accelerator rack having a series of teeth and the bell crank gear may include a series of teeth engaged with the teeth of the accelerator rack. Axial translation of the accelerator rack may result in rotation of the bell crank gear and axial translation of the pusher bar.

The accelerator rack may be connected to the drive channel via a biasing member.

According to a further aspect of the present disclosure, a surgical clip applier mechanism operable to deliver at least relatively small and large surgical clips, the surgical clip applier mechanism is provided and includes a drive channel capable of translatable movement; a pair of jaws engageable by a distal end of the drive channel, wherein the pair of jaws are approximated upon distal translation of the drive channel; a wedge plate capable of reciprocal translation relative to the drive channel, wherein a distal end of the wedge plate is selectively positionable between the pair of jaws, the wedge plate defining a plurality of apertures formed along a length thereof; a clip carrier fixedly located with respect to the drive channel, the clip carrier defining a channel and a plurality of windows formed along a length thereof; a plurality of clips slidably disposed within said channel of said clip carrier; a clip follower slidably disposed within said channel of said clip carrier at a location proximal of said plurality of clips; a pusher bar capable of reciprocal translation relative to the drive channel, wherein a distal end of the pusher bar is configured for engagement with a distal-most clip of the plurality of clips; a motion multiplier system including bell crank gear and an accelerator rack, the accelerator rack being coupled to the drive channel via a biasing member, the bell crank gear being coupled to the accelerator rack via complementary gear teeth, and the bell crank gear being coupled to the pusher bar, wherein distal translation of the drive channel causes the accelerator rack to translate distally, causing the bell crank gear to rotate, causing the pusher bar to translate distally; and a pivot arm including a first end connected to the drive channel, and a second end connected to the wedge plate and engageable by the pusher bar. In use, distal translation of the drive channel causes the first end of the pivot arm to translate distally, causing the second end of the pivot arm to translate in a proximal direction, thus causing the wedge plate to translate in a proximal direction; and distal translation of the pusher bar is stopped upon contact of the pusher bar with the second end of the pivot arm.

The further translation of the second end of the pivot arm in the proximal direction may cause the pusher bar to translate in a proximal direction. Actuation of the pivot arm by the drive channel may occur after a dwell period.

BRIEF DESCRIPTION OF THE DRAWINGS

The present clip applier will be more fully appreciated as the same becomes better understood from the following detailed description when considered in connection with the following drawings, in which:

FIG. 4A is an exploded perspective view of a bell crank gear and accelerator rack assembly of the surgical clip applier of FIGS. 1-4;

FIG. 4B is a perspective view of the accelerator rack of the surgical clip applier of FIGS. 1-4;

FIG. 4C is a perspective view of the bell crank gear of the surgical clip applier of FIGS. 1-4;

FIG. 4D is a top, perspective view of a pivot arm of the surgical clip applier of FIGS. 1-4;

FIG. 4E is a bottom, perspective view of the pivot arm of FIG. 4D;

FIG. 4F is a top, perspective view of a clip follower of the surgical clip applier of FIGS. 1-4;

FIG. 4G is a perspective view of an audible/tactile indicator of the surgical clip applier of FIGS. 1-4;

FIG. 4H is a perspective view of a rack member of the surgical clip applier of FIGS. 1-4;

FIG. 7 is an enlarged view of the indicated area of detail of FIG. 5;

FIG. 8 is an enlarged view of the indicated area of detail of FIG. 5;

FIG. 18 is a top, perspective view of the surgical clip applier of FIGS. 1-4, illustrated with the upper housing half, the pusher bar and a wedge plate removed therefrom;

FIG. 19 is a top, perspective view of a distal end of the channel assembly of FIG. 12, with the cover, the pusher bar, the clip carrier, the surgical clips, the clip follower and the wedge plate removed therefrom;

FIG. 20 is a top, perspective view of the surgical clip applier of FIGS. 1-4, illustrated with the upper housing half, the pusher bar, the wedge plate and a drive channel removed therefrom;

FIG. 21 is a bottom, perspective view of the surgical clip applier of FIGS. 1-4, illustrated with a lower housing half, the drive channel and the wedge plate removed therefrom;

FIG. 22 is a top, plan view of the surgical clip applier of FIGS. 1-4, with the upper housing half removed therefrom and shown in an un-actuated condition;

DETAILED DESCRIPTION OF EMBODIMENTS

Figure 1:
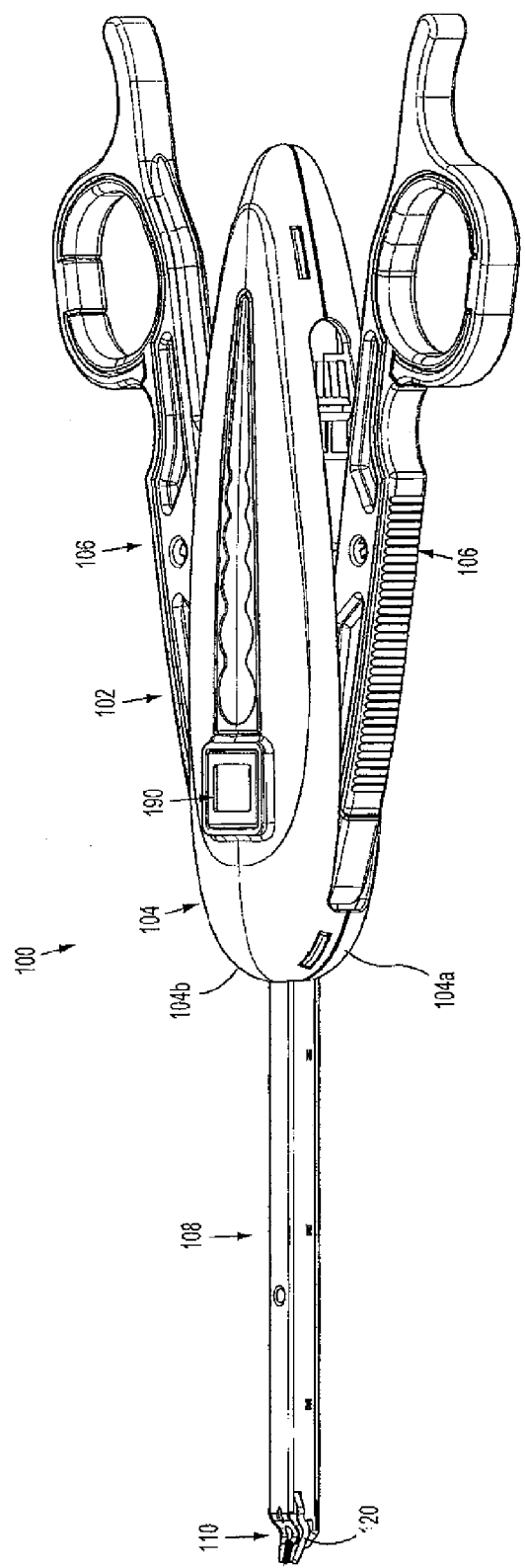
FIG. 1 is a perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-5, a surgical clip applier in accordance with an embodiment of the present disclosure is generally designated as 100. Surgical clip applier 100 generally includes a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends outwardly therefrom, terminating in a jaw assembly 110.

As seen in FIGS. 1-4, housing halves 104a and 104b of clip applier 100 fit together by snap fit engagement with one another. Housing 104 defines a window 104c formed in lower housing half 104b for supporting and displaying a counter mechanism, as will be discussed in greater detail below. Housing 104 is formed of a suitable plastic material.

Figure 4:
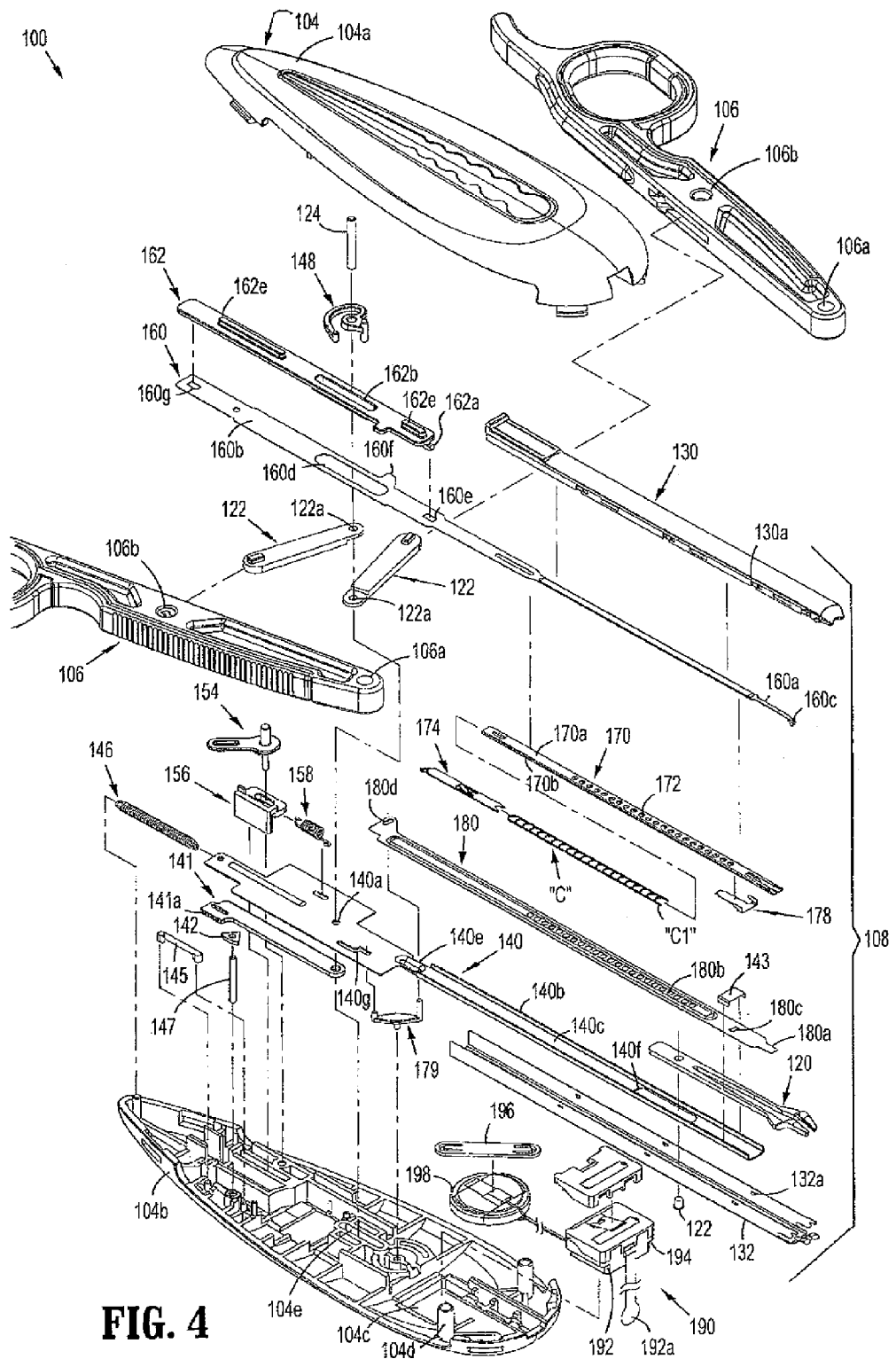
FIG. 4 is an exploded perspective view of the surgical clip applier of FIGS. 1-3.
Figure 5:
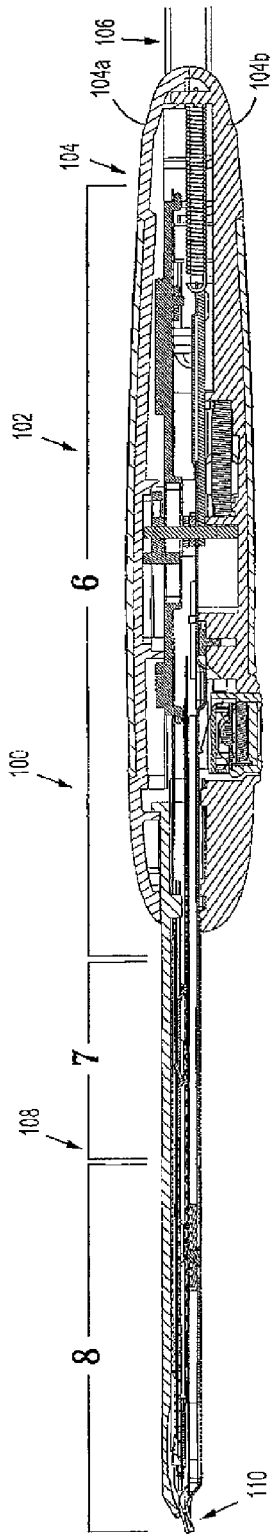
FIG. 5 is a longitudinal cross-sectional view of the surgical clip applier of FIGS. 1-4, illustrating the surgical clip applier in an unactuated condition.

As seen in FIG. 4, handles 106 are secured to housing 104 by handle pivot posts 104d extending from lower housing half 104b and into respective apertures 106a formed in handles 106. Handle assembly 102 includes a link member 122 pivotally connected to each handle 106 at a pivot point 106b formed in a respective handle 106. A distal end 122a of each link member 122 is pivotally connected to a pivot point 140a formed in a drive channel 140 via a drive pin 124. Each end of drive pin 124 is slidably received in an elongate channel 104e formed in a respective upper and lower housing half 104a, 104b. In use, as will be described in greater detail below, as handles 106 are squeezed, link members 122 push drive channel 140 distally via drive pin 124.

Channel assembly 108 includes a channel or cartridge cover 130 and an outer or lower channel 132 each having a proximal end retained in housing assembly 102, between upper and lower housing halves 104a, 104b. Cartridge cover 130 includes at least one retention element 130a configured and adapted to selectively engage, in a snap-fit engagement, a complementary or corresponding retention element 132a provided on outer channel 132.

As seen in FIGS. 4 and 6-12, clip applier 100 includes a clip pusher bar 160 slidably disposed beneath cartridge cover 130. Pusher bar 160 includes a distal end 160a defining a pusher 160c configured and adapted to selectively engage/move a distal-most clip "C1" stored in surgical clip applier 100. Pusher bar 160 further includes a proximal end 160b defining a proximal window 160d therein for slidably receiving drive pin 124 therein. Pusher bar 160 further defines a distal window 160e therein for operative engagement with a stabilizer 162, as will be discussed in greater detail below. Pusher bar 160 also includes a fin 160f projecting from a side edge thereof and located in relative close proximity to proximal window 160d.

Figure 6:
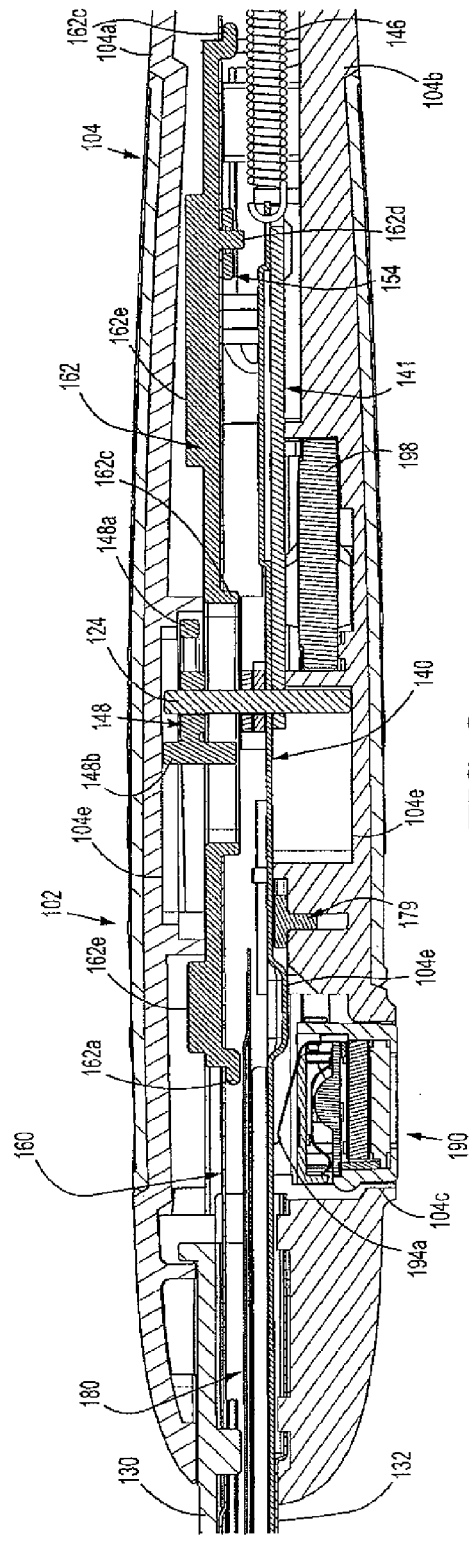
FIG. 6 is an enlarged view of the indicated area of detail of FIG. 5.

Clip applier 100 further includes a stabilizer 162 configured to overlie and engage pusher bar 160. Stabilizer 162 includes a distal tab 162a configured to engage distal window 160e of pusher bar 160, an elongate window 162b defined therein at a location to substantially overlie and be in registration with proximal window 160d formed in pusher bar 160. Stabilizer 162 further includes a nub 162c extending from a bottom surface thereof, at a location proximal of elongate window 162b, which is configured and dimensioned for receipt in a proximal-most aperture 160g formed in pusher bar 160. As seen in FIGS. 4 and 6, stabilizer 162 further includes a pair of tabs 162e extending from a top surface thereof, at a proximal and a distal location, which are configured and dimensioned for receipt in respective channels formed in upper housing half 104a.

As seen in FIGS. 4 and 4A-4C, clip applier 100 further includes a motion multiplier system having a bell crank gear 154 pivotally supported in housing 104 and an accelerator housing 156 slidably supported in housing 104. Bell crank gear 154 includes a pivot pin 154a configured for pivotable connection to housing 104, a disk-like body 154b supported on pivot pin 154a, an arm 154c extending radially from disk-like body 154b, and a spur gear 154d supported on pivot pin 154a or integrally formed therewith and located adjacent disk-like body 154b. Bell crank gear 154 defines a detent or notch 154e (see FIG. 24) formed in a side edge of disk-like body 154b and a longitudinally oriented slot 154f formed in arm 154c. Spur gear 154d of bell crank gear 154 defines a plurality of gear teeth 154g formed in a side edge thereof and may be a sector gear as best shown in FIG. 4C.

Bell crank gear 154 is a common part for each of the small and large scaled clip appliers 100. Notch 154e formed in side edge of disk-like body 154b of bell crank gear 154 is provided for the assembly of the large scaled clip applier. The larger scaled clip applier requires a greater pusher stroke and therefore a greater degree of rotation of bell crank gear 154. Due to the greater rotation of bell crank gear 154, disk-like body 154b will contact a tab 156e (see FIGS. 4A and 4B) extending from an accelerator rack 156. During assembly, bell crank gear 154 is rotated until notch 154e contacts tab 156e of accelerator rack 156.

With continued reference to FIGS. 4 and 4A-4C, accelerator rack 156 of motion multiplier system includes a base wall 156a defining an elongate, longitudinally extending slot 156b formed therein, for slidable receipt of pivot pin 154a of bell crank gear 154. Accelerator rack 156 includes a side wall 156c projecting in opposite directions from a side edge of base wall 156a, and a gear rack 156d formed in side wall 156c and in registration or alignment with slot 156b of base wall 156a. Gear rack 156d is configured for engagement with gear teeth 154g of spur gear 154d of bell crank gear 154.

Clip applier 100 further includes a biasing member 158 interconnecting accelerator rack 156 and drive channel 140.

As seen in FIG. 6, slot 154f of arm 154c of bell crank gear 154 is configured and dimensioned to slidably and rotatably receive a nub 162d of stabilizer 162 therein. In use, as drive channel 140 is translated distally, biasing member 158, which interconnects drive channel 140 and accelerator rack 156, subsequently moves accelerator rack 156 distally. As accelerator rack 156 is moved distally, since nub 162d of stabilizer 162 rides in slot 154f of arm 154c of bell crank gear 154, accelerator rack 156 causes bell crank gear 154 to rotate and push stabilizer 162 and, in turn, pusher bar 160 distally.

Clip applier 100 further includes a clip carrier 170 disposed within channel assembly 108 and beneath pusher bar 160. Clip carrier 170 is generally a box-like structure having an upper wall 170a, a pair of side walls 170b and a lower wall 170c defining a channel 170d therethrough. Clip carrier 170 includes a plurality of spaced apart windows 172 formed in upper wall 170a and extending longitudinally along a length thereof. Clip carrier 170 includes an elongate window 170e (see FIG. 9) formed in lower wall 170c and extending longitudinally along a length thereof.

Figure 9:
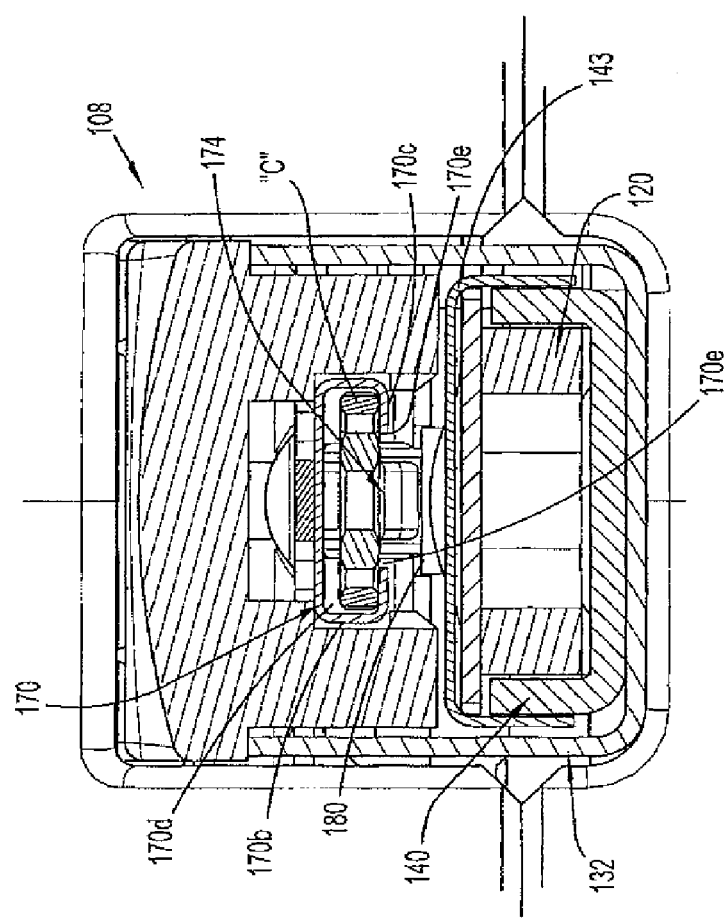
FIG. 9 is a cross-sectional view of the surgical clip applier of FIGS. 1-4, as taken through 9-9 of FIG. 8.
Figure 10:
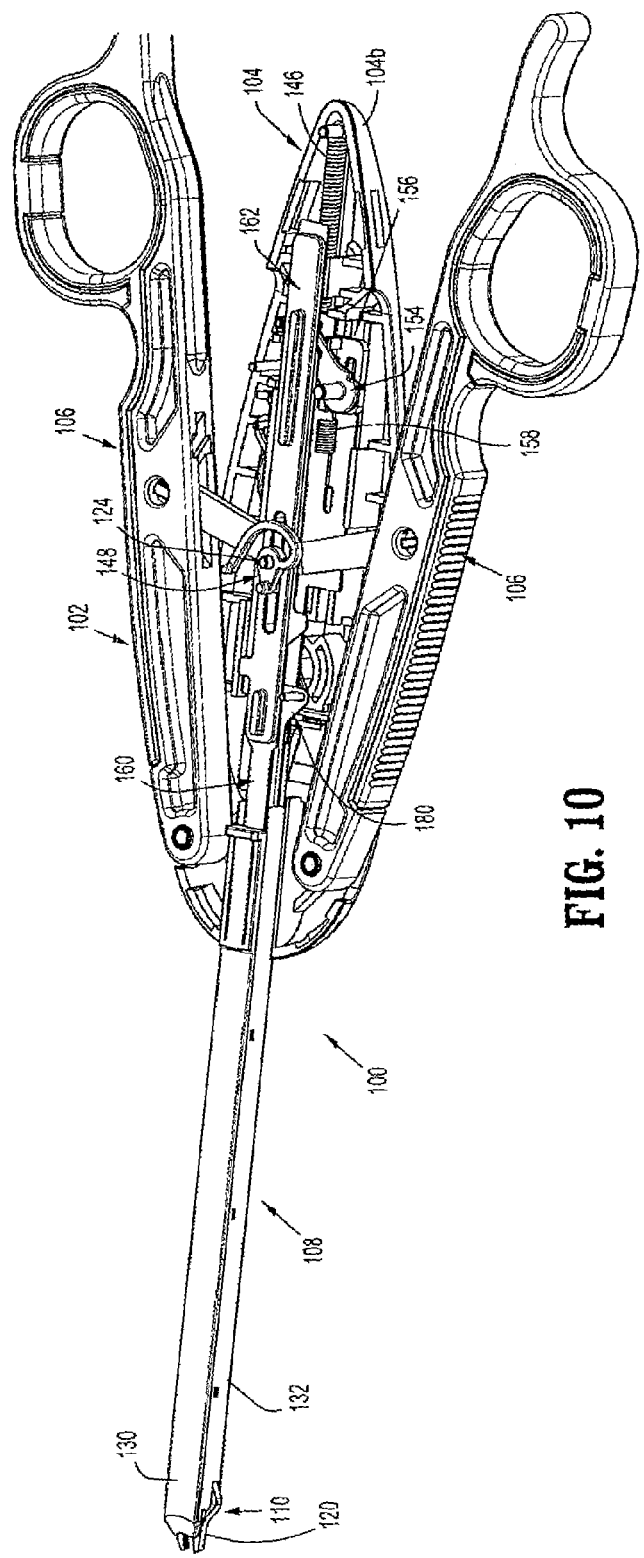
FIG. 10 is a perspective view of the surgical clip applier of FIGS. 1-4, illustrated with an upper housing half removed therefrom.
Figure 11:
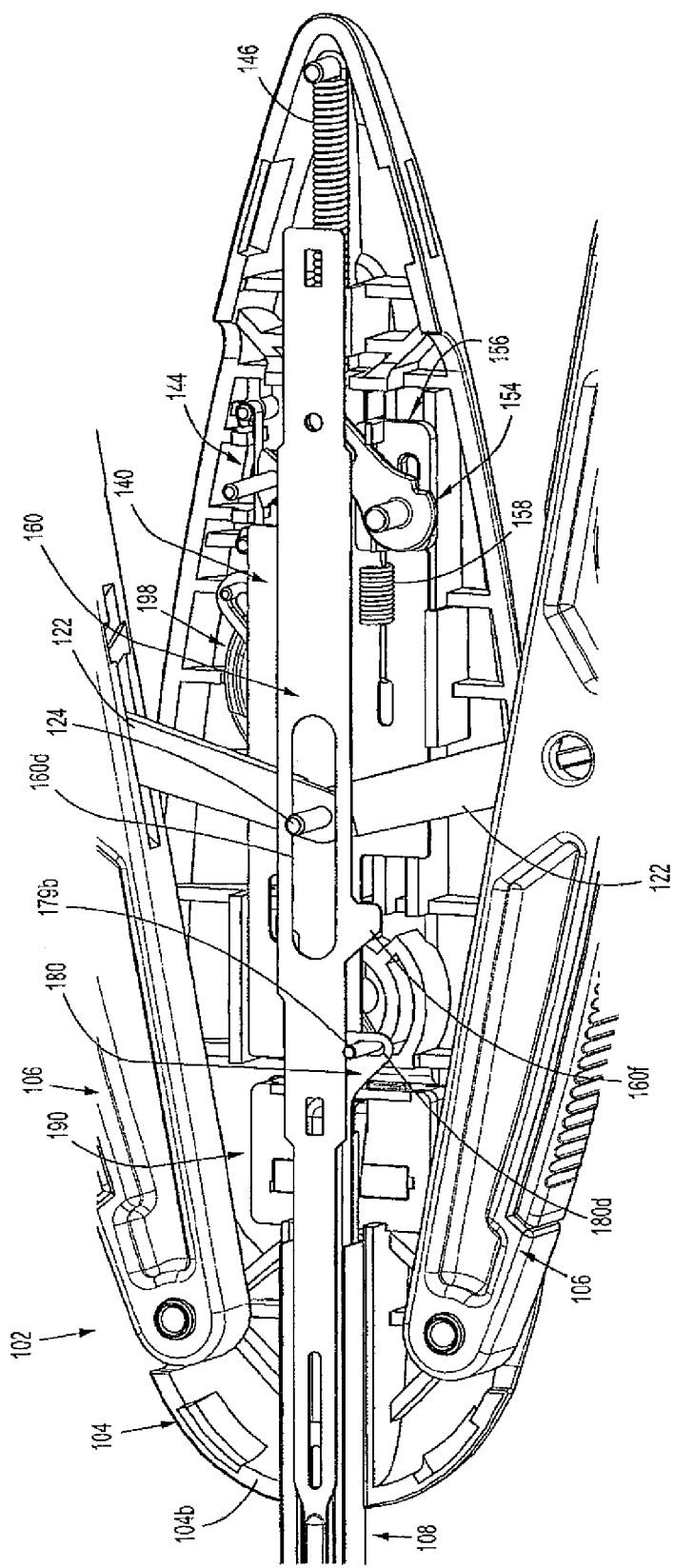
FIG. 11 is an enlarged view of the surgical clip applier of FIGS. 1-4, as shown in FIG. 10.
Figure 14:
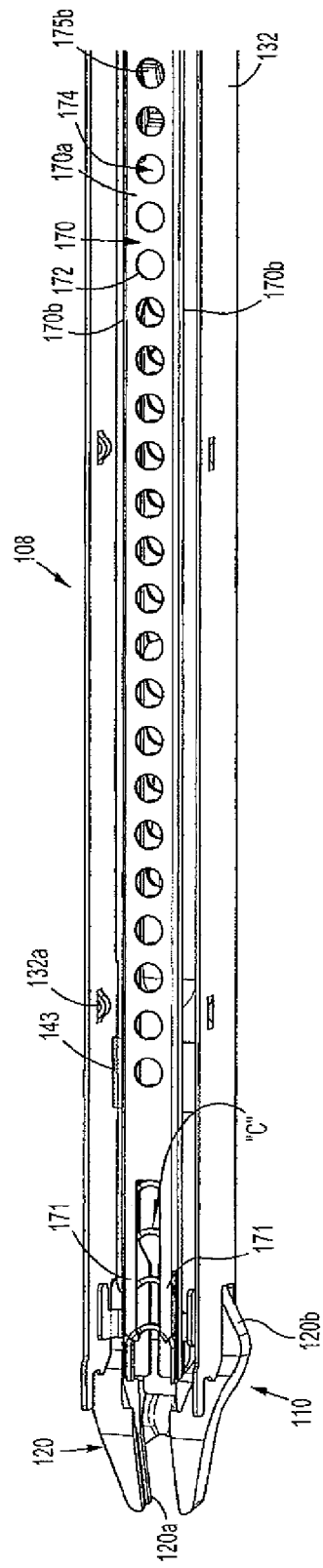
FIG. 14 is a top, perspective view of a distal end of the channel assembly of FIG. 12, with the cover and the pusher bar removed therefrom.
Figure 15:
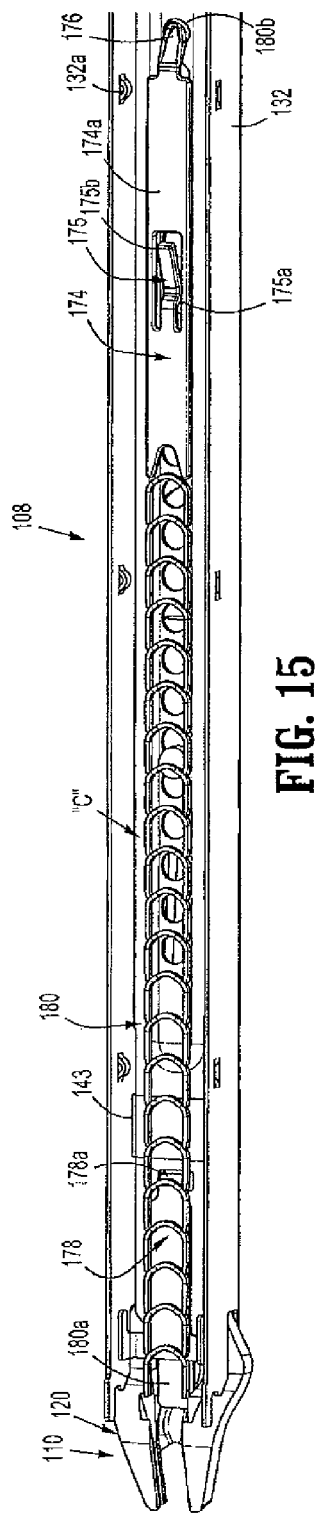
FIG. 15 is a top, perspective view of a distal end of the channel assembly of FIG. 12, with the cover, the pusher bar and a clip carrier removed therefrom.
Figure 16:
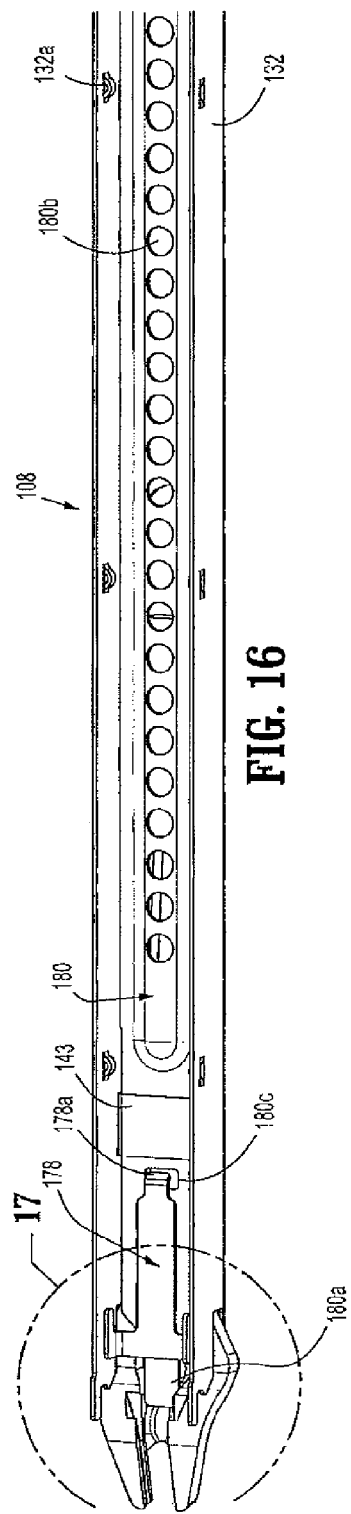
FIG. 16 is a top, perspective view of a distal end of the channel assembly of FIG. 12, with the cover, the pusher bar, the clip carrier, the surgical clips and the clip follower removed therefrom.

As seen in FIGS. 4, 9 and 14, a stack of surgical clips "C" is loaded and/or retained within channel 170d of clip carrier 170 in a manner so as to slide therewithin and/or therealong. Channel 170d is configured and dimensioned to slidably retain a stack or plurality of surgical clips "C" in tip-to-tail fashion therewithin.

Figure 12:
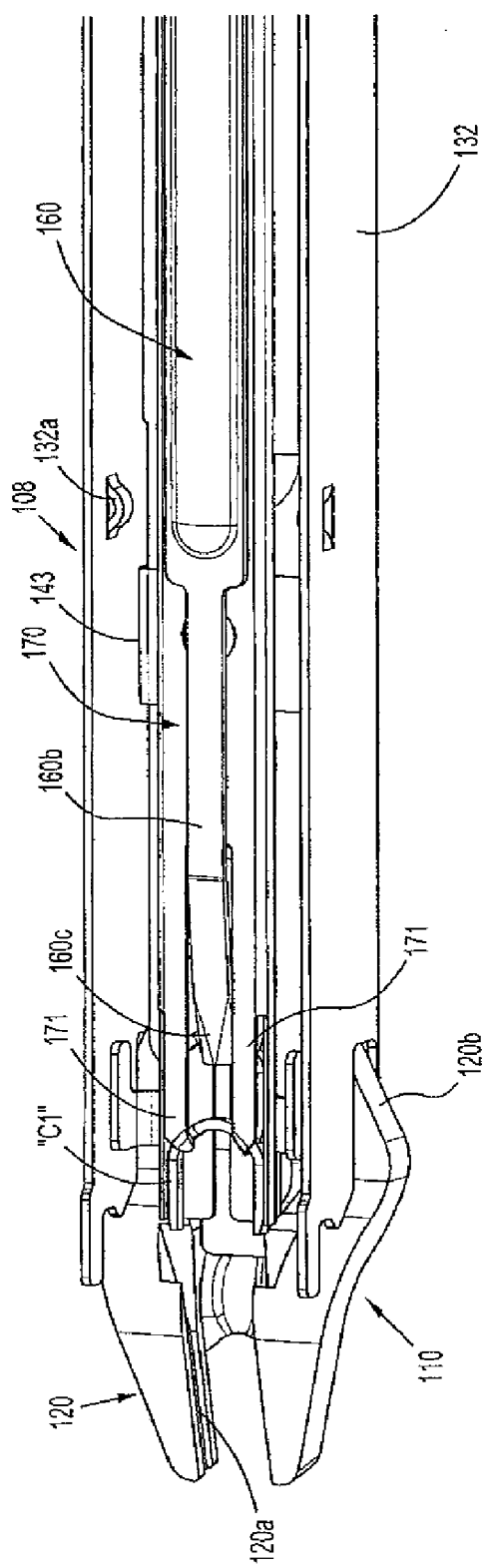
FIG. 12 is a top, perspective view of a distal end of a channel assembly of the surgical clip applier of FIGS. 1-4, with a cover removed therefrom.
Figure 13:
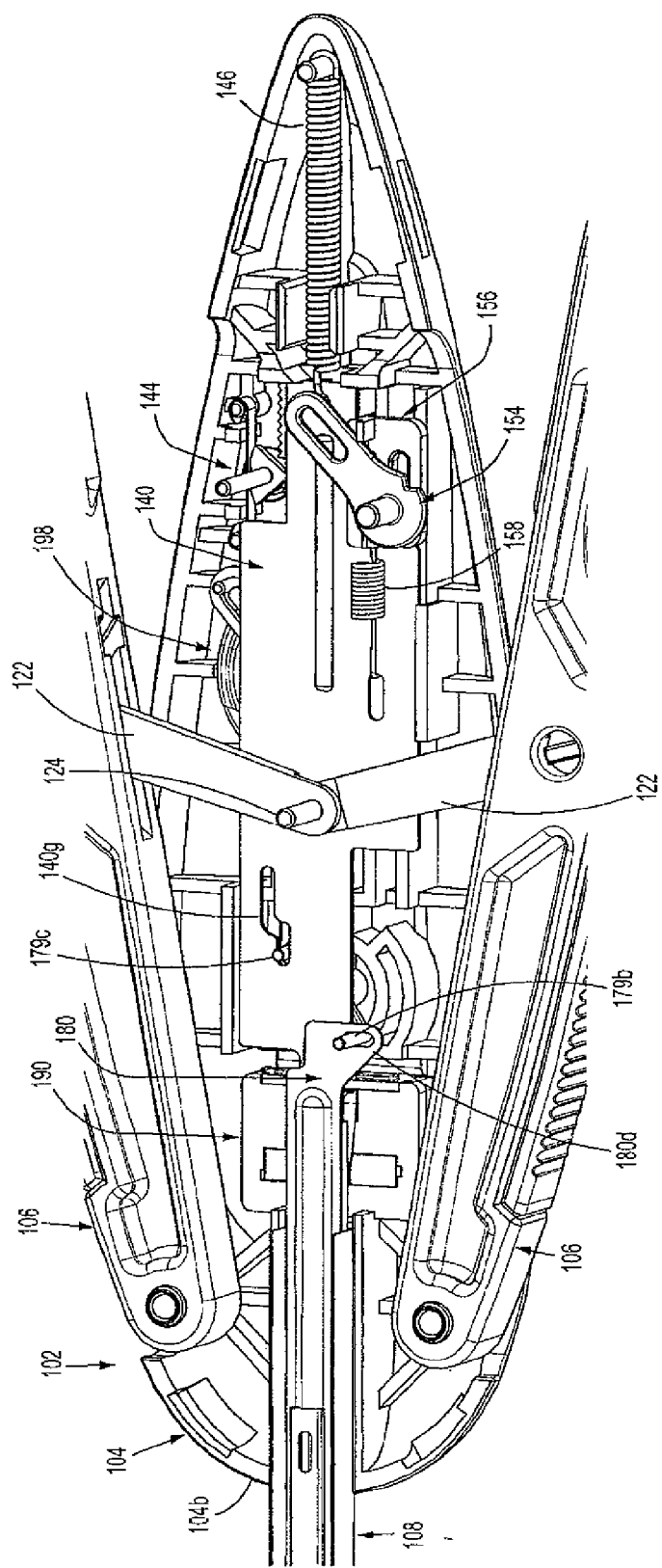
FIG. 13 is a top, perspective view of the surgical clip applier of FIGS. 1-4, illustrated with the upper housing half and a pusher bar removed therefrom.

As seen in FIGS. 12 and 14, a distal end of clip carrier 170 includes a pair of spaced apart, resilient tangs 171. Tangs 171 are configured and adapted to selectively engage a backspan of a distal-most surgical clip "C1" of the stack of surgical clips "C" retained within carrier 170.

As seen in FIGS. 4, 4F, 7 and 15, clip applier 100 further includes a clip follower 174 slidably disposed within channel 170d of clip carrier 170. As will be discussed in greater detail below, clip follower 174 is positioned behind the stack of surgical clips "C" and is provided to urge the stack of clips "C" forward during an actuation of clip applier 100. As will be described in greater detail below, clip follower 174 is actuated by the reciprocating forward and backward motion of wedge plate 180.

As seen in FIGS. 4F and 7, clip follower 174 includes body portion 174a defining a plane, a distal tab 175 extending substantially upwardly and rearwardly from body portion 174a, and a proximal tab 176 extending substantially downwardly and rearwardly from body portion 174a. Distal tab 175 includes a distal portion 175a extending downwardly below the plane defined by body portion 174a and a proximal portion 175b extending upwardly above the plane defined by body portion 174a.

Proximal portion 175b of distal tab 175 is configured and dimensioned to selectively engage windows 172 formed in upper wall 170a of clip carrier 170. In use, engagement of proximal portion 175b of distal tab 175 of clip follower 174 in a window 172 formed in upper wall 170a of clip carrier 170 prevents clip follower from traveling or moving in a proximal direction.

Proximal tab 176 is configured and dimensioned to selectively engage windows 180b formed in wedge plate 180. In use, engagement of proximal tab 176 of clip follower 174 in a window 180h formed in wedge plate 180 allows for clip follower 174 to be advanced or moved distally upon a distal movement of wedge plate 180.

As seen in FIGS. 4, 7-9, 16 and 17, clip applier 100 further includes a wedge plate 180 slidably disposed within handle assembly 102 and channel assembly 108. Wedge plate 180 is positioned or disposed below clip carrier 170. Wedge plate 180 includes a substantially tapered distal end 180a for selective operative interposition between jaws 120. Wedge plate 180 defines a plurality of spaced apart windows or apertures 180b extending longitudinally along a length thereof and formed in a raised section thereof, a distal window or aperture 180c located distal of apertures 180b, and a proximal-most transversely oriented slot 180d located proximal of aperture 180c.

As seen in FIGS. 4, 8, 16 and 17, clip applier 100 includes a distal lockout 178 supported by cartridge cover 130. Distal lockout 178 includes a tail or tab 178a extending substantially rearwardly and downwardly and being configured and dimensioned for receipt in distal window or aperture 180c of wedge plate 180.

As seen in FIGS. 4, 4D, 4E, 6, 11, 13, 18 and 20, clip applier 100 includes a wedge plate motion reversing mechanism, in the form of a pivot arm 179, pivotally supported in lower housing half 104b of housing 104 for transmitting the translation of drive channel 140 to a reverse translation of wedge plate 180. Pivot arm 179 includes a pivot boss 179a configured for pivotable connection to housing 104, a first stem or finger 179b provided at one end of pivot arm 179 and extending in a direction opposite to pivot boss 179a, and second stem or finger 179c provided at a second end of pivot arm 179 and extending in a direction opposite to pivot boss 179a. First stem or finger 179b is configured and adapted for engagement in proximal-most slot 180d of wedge plate 180. Second stem or finger 179c is configured for engagement in a slot 140g formed in drive channel 140 which is connected to a window 140g defined in a drive channel 140. Slot 140g includes a longitudinally extending distal portion and a longitudinally extending proximal portion that are axially and transversely offset from one another, and a transverse portion interconnecting the distal and proximal portions.

Figure 17:
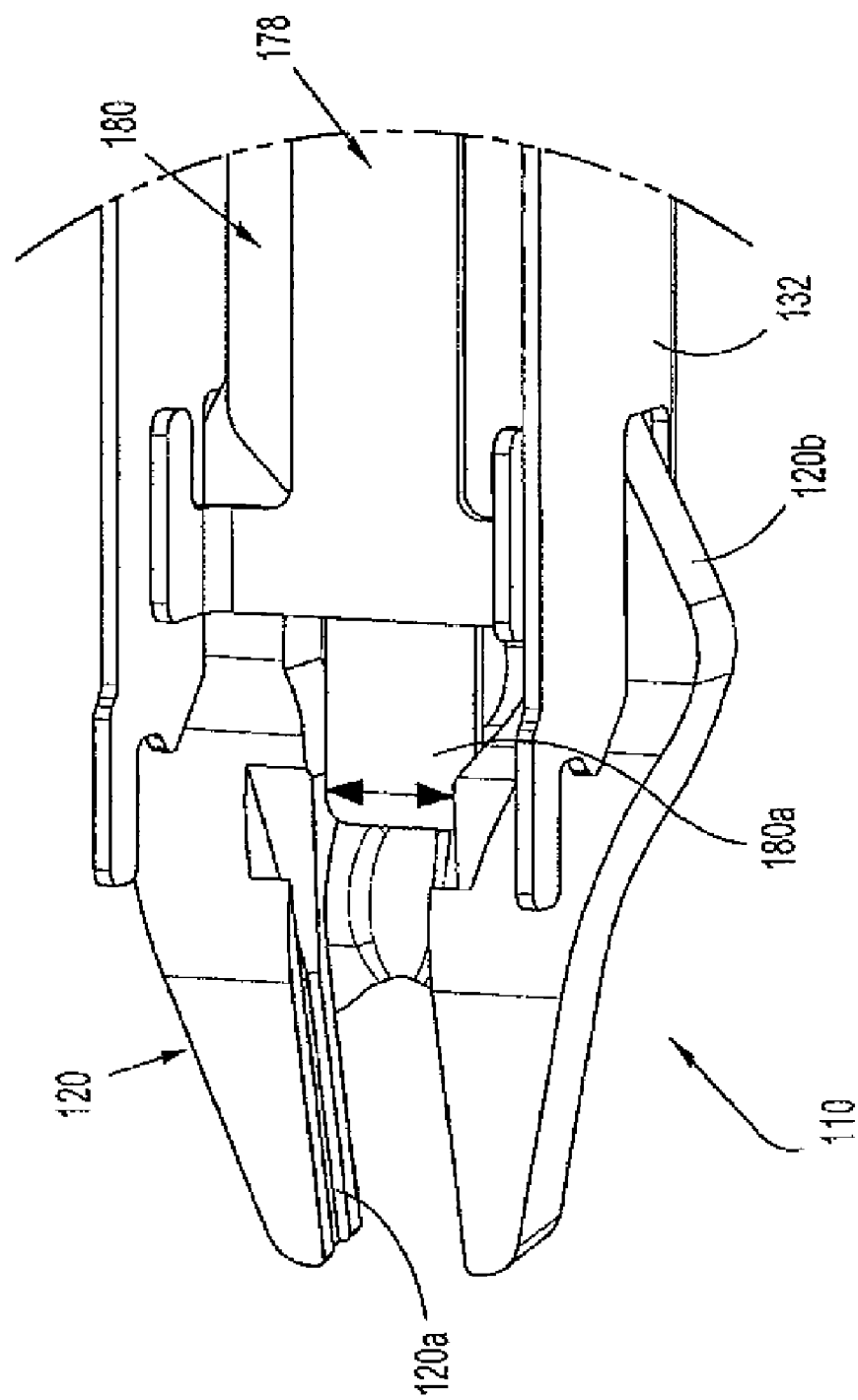
FIG. 17 is an enlarged view of the indicated area of detail of FIG. 16.

In use, as will be discussed in greater detail below, as drive channel 140 is moved distally, after a dwell period (i.e., the length of the longitudinally extending distal portion of slot 140g of drive channel 140), second stem or finger 179c is moved in a distal direction, rotating pivot arm 179 and thereby moving first stem or finger 179b in a second direction. As first stem or finger 179b is moved in the second direction, first stem or finger 179b pulls wedge plate 180 out from between jaws 120 urges against as well as urges or pushes proximally against fin 160f of pusher 160 to move pusher 160 in a proximal direction so that pusher bar 160c thereof is removed from between jaws 120, and vice-versa. As wedge plate 180 is moved in a distal direction, as seen in FIG. 17, distal end 180a of wedge plate 180 cams against an inner surface of jaws 120 to thereby maintain jaws 120 spaced apart from one another.

As seen in FIGS. 4, 6-11, 13, 18 and 19, clip applier 100 includes a drive channel 140 reciprocally supported in and extending between housing 104 of handle assembly 102 and channel assembly 108. A proximal end of drive channel 140 is supported between upper and lower housing halves 104a, 104b of housing 104 and a distal end of drive channel 140 is supported between cartridge cover 130 and outer channel 132 of channel assembly 108, at a location below wedge plate 180.

A distal end of drive channel 140 is a substantially U-shaped channel including a pair of spaced apart side walls 140b extending from a backspan 140c thereof, in a direction away from outer channel 132 and toward cartridge cover 130. Drive channel 140 further defines a drive pin recess 140a formed in backspan 140c for pivotally receiving drive pin 124 therethrough. Drive channel 140 further defines a rib 140e projecting from backspan 140c at a location distal of drive pin recess 140a. Drive channel 140 further defines a reciprocation limiting slot 140f formed in backspan 140c at a location distal of slot 140e.

As seen in FIGS. 4, 8, 9, 12, 14-16 and 19, clip applier 100 includes a drive channel strap 143 secured to drive channel 140. Strap 143 is secured to uprights 140b of drive channel 140 so as to extend transversely thereacross. Strap 143 is secured to drive channel 140 at a location distal of reciprocation limiting slot 140f. Strap 143 is secured to drive channel 140 such that wedge plate 180 extends beneath strap 143 and above jaws 120.

As seen in FIGS. 4, 4G, 6, 10 and 21, clip applier 100 further includes an audible/tactile indicator 148 connected to drive channel 140 via drive pin 124. Indicator 148 includes a resilient finger 148a and a pair of bosses 148b. In use, as will be described in greater detail below, as clip applier 100 is actuated and drive channel 140 is reciprocated, first resilient finger 148a of indicator 148 interacts with corresponding complementary structure or ledge 149 provided in clip applier 100 to create an audible and/or a tactile feedback to the user. Bosses 148b of indicator 148 ride within channel 104e formed in upper housing half 104a and provide support to indicator 148 to prevent indicator 148 from rotating.

As seen in FIGS. 4, 6, 10, 11, 13, 18 and 20, clip applier 100 further includes a biasing member 146, in the form of a tension spring, operatively secured to and between a proximal end of drive channel 140 and housing 104, tending to maintain drive channel 140 in a retracted or proximal-most position. Biasing member 146 functions to retract or facilitate retraction of drive channel 140 following formation of a clip "C" positioned between jaws 120.

As seen in FIGS. 4, 4H, 11, 13, 18 and 20, a proximal end of drive channel 140 includes a ratchet rack member 141 secured to drive pin 124 and movable with drive channel 140. Ratchet rack member 141 is configured and adapted to engage with a ratchet pawl 142 supported in housing 104. Rack member 141 and pawl 142 define a ratchet mechanism 144. In use, as drive channel 140 is moved axially, rack member 141 is also moved. Rack member 141 defines a series of rack teeth 141a having a length which allows pawl 142 to reverse and advance back over rack member 141 when rack member 141 changes between proximal and distal movement as drive channel 140 reaches a proximal-most or distal-most position.

Pawl 142 is pivotally connected to lower housing half 104b by a pawl pin 147 at a location wherein pawl 142 is in substantial operative engagement with rack member 141. Pawl 142 is engageable with rack member 141 to restrict longitudinal movement of rack member 141 and, in turn, drive channel 140. Ratchet mechanism 144 further includes a pawl spring 145 configured and positioned to bias pawl 142 into operative engagement with rack member 141. Pawl spring 145 functions to maintain the teeth of pawl 142 in engagement with the teeth 141a of rack member 141, as well as to maintain pawl 142 in a rotated or canted position.

As seen in FIGS. 1-4, 8, 10, 12, 14-17 and 19, clip applier 100 includes a pair of jaws 120 mounted on or at a distal end of channel assembly 108 and actuatable by handles 106 of handle assembly 102. Jaws 120 are formed of a suitable biocompatible material such as, for example, stainless steel or titanium.

Jaws 120 are mounted in a distal end of drive channel 140 via a rivet 122 or the like extending through reciprocation limiting slot 140f of drive channel 140 such that jaws 120 are longitudinally stationary relative to outer channel 132 and drive channel 140. As seen in FIGS. 12, 14, 17 and 19, jaws 120 define a channel 120a therebetween for receipt of a surgical clip "C1" therein.

As seen in FIGS. 1-4, 6, 11, 13 and 20, clip applier 100 further includes a counter mechanism 190 supported in housing 104 of handle assembly 102. Counter mechanism 190 includes a display 192, a processor 194, and an energy source 198 in the form of a battery or the like. Display 192 is a liquid crystal display that displays one or more operating parameters of clip applier 100 to the surgeon. The operating parameter displayed may be an amount or number of remaining clips, a number of clips that have been used, a position parameter, a surgical time of usage, or any other parameter of the procedure.

Figure 1A:
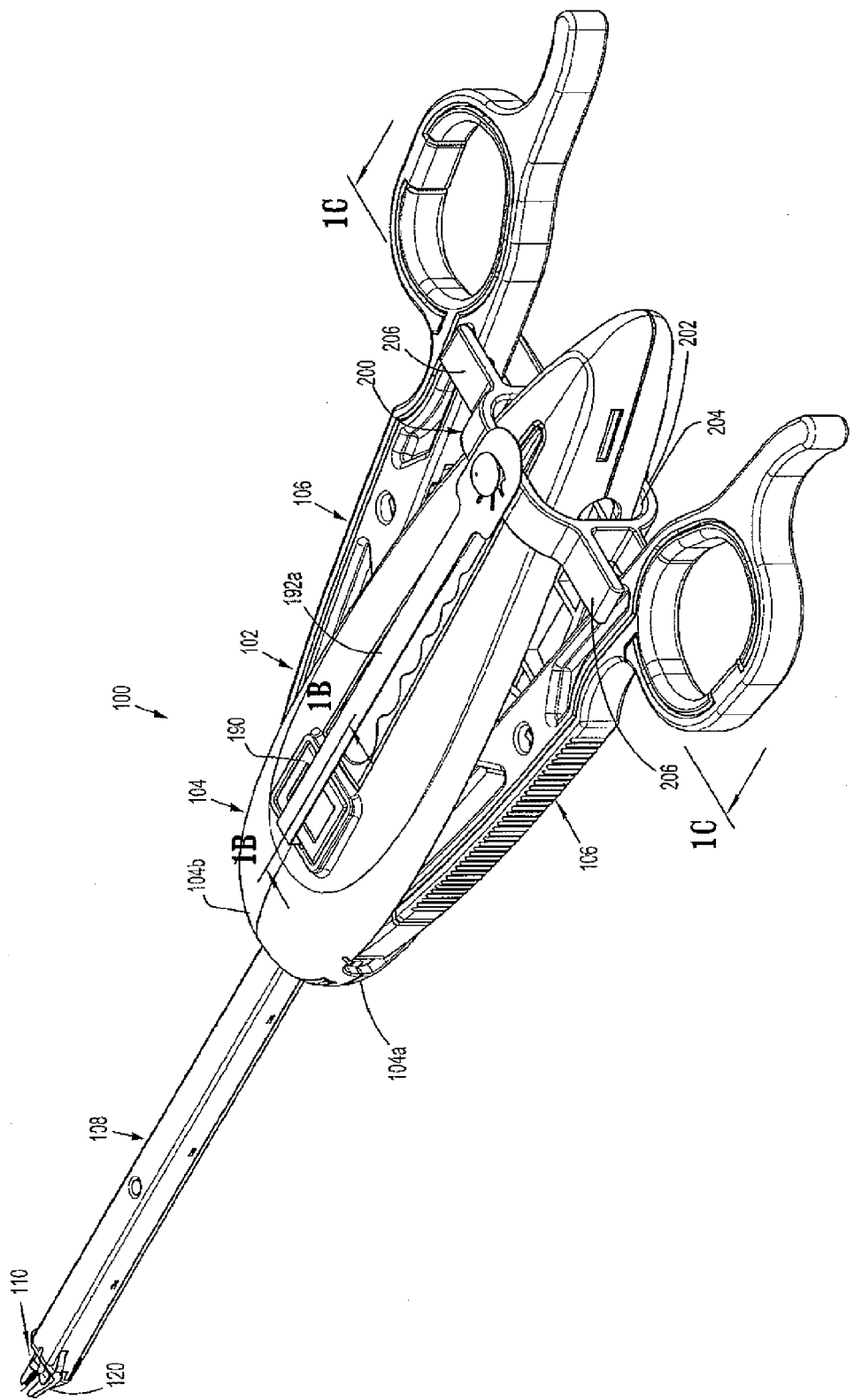
FIG. 1A is a rear, perspective view of the surgical clip applier of FIG. 1, shown with a shipping wedge in position.
Figure 1B:
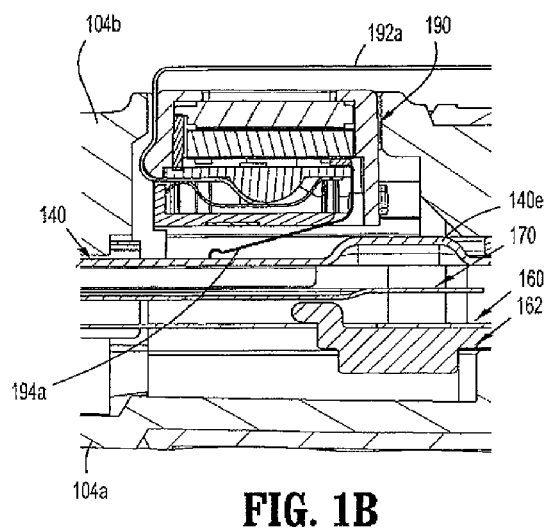
FIG. 1B is a cross-sectional view as taken through 1B-1B of FIG. 1A.

Counter mechanism 190 includes a tab 192a, made from PVC, disposed between battery or energy source 198 and a contact 194a of processor 194 or between the contacts 194a of processor 194 to prevent the battery or energy source 198 from becoming drained during storage. As seen in FIGS. 1A and 1B, tab 192a extends out of housing 104 of clip applier 100 in order to allow for easy removal of the tab therefrom. Once the tab 192a is removed, battery or energy source 198 comes into electrical contact with the contact 194a of processor 194 or between the contacts 194a of the processor 194.

Figure 36:
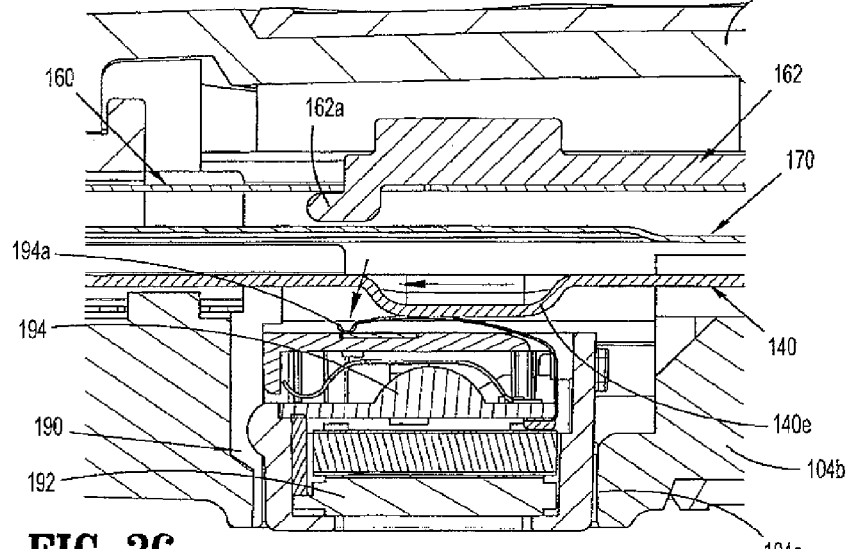
FIG. 36 is an enlarged, cross-sectional view illustrating an actuation of a counter mechanism of the surgical clip applier of FIGS. 1-4.

Counter mechanism 190 is actuated by nub 140e formed in drive channel 140. In use, as seen in FIG. 36, as drive channel 140 is driven forward, nub 140e thereof engages contact 194a causing contact 194a to complete a circuit and trigger processor 194 to perform a function (e.g., reduce the number appearing on display 192 by a give increment or value).

Figure 1C:
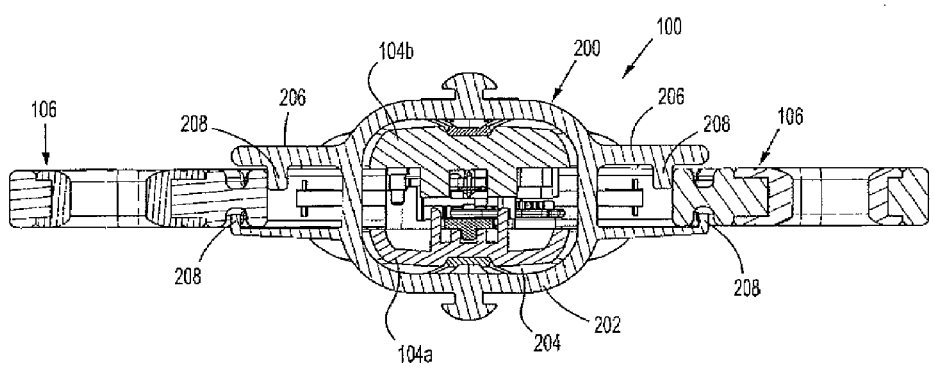
FIG. 1C is a cross-sectional view as taken through 1C-1C of FIG. 1A.
Figure 2:
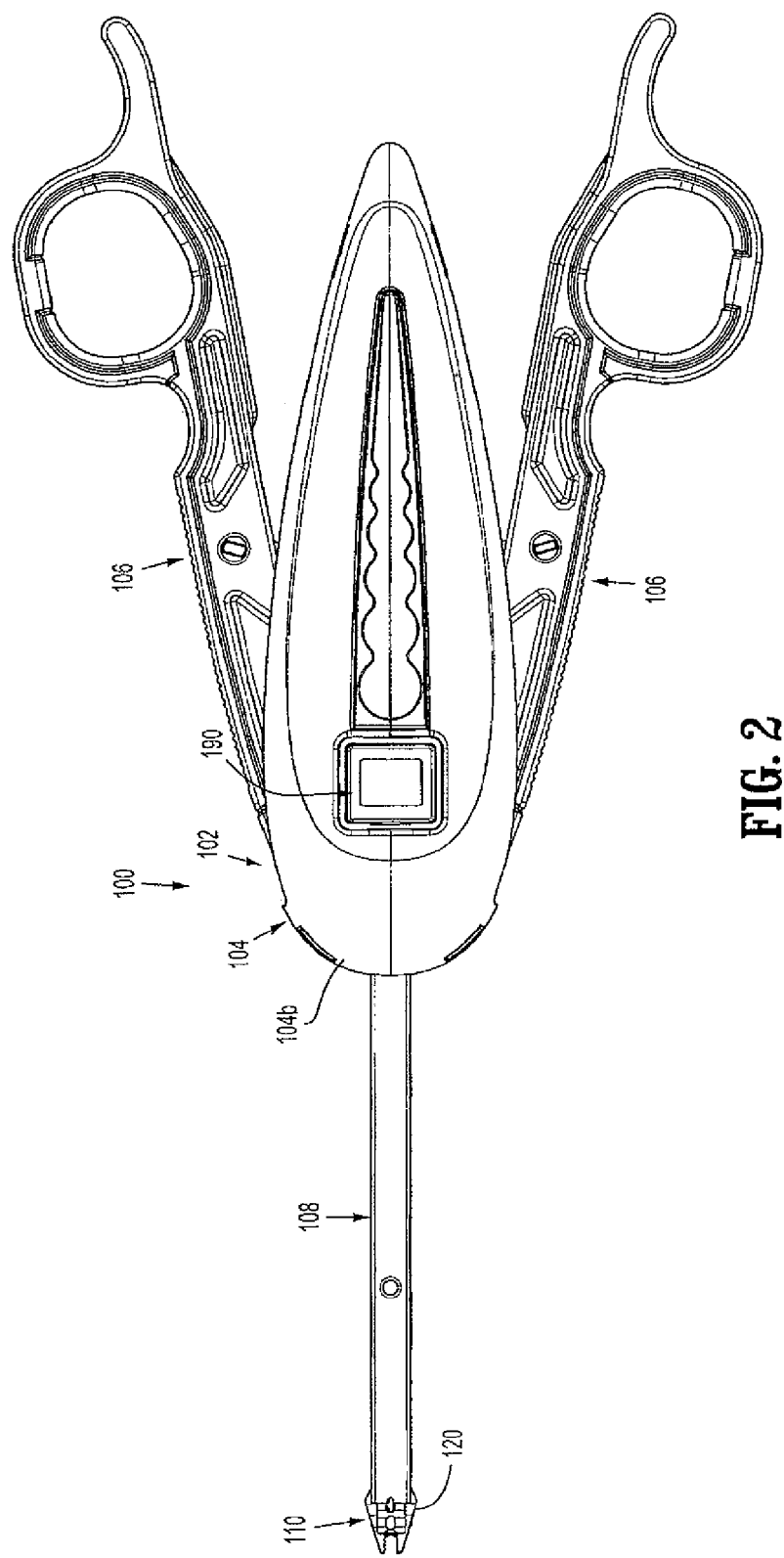
FIG. 2 is a top, plan view of the surgical clip applier of FIG. 1.
Figure 3:
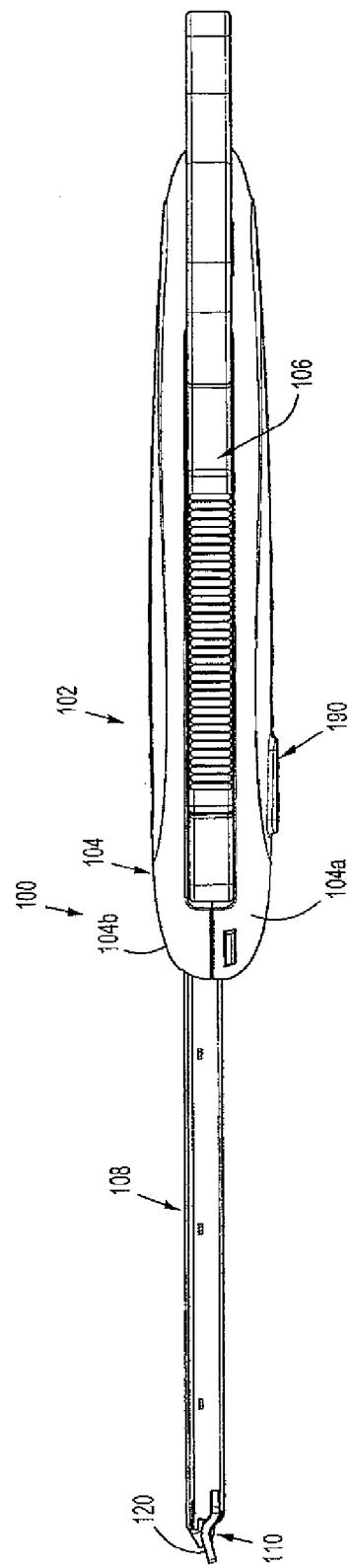
FIG. 3 is a side, elevational view of the surgical clip applier of FIGS. 1 and 2.

As seen in FIGS. 1A and 1C, clip applier 100 includes a shipping wedge 200 supported on housing 104 and interposed between handles 106. Shipping wedge 200 functions to maintain handles 106 spaced apart or un-squeezed during a shipment and/or storage of clip applier 100. Shipping wedge 200 is connected to tab 192a of counter mechanism 190, such that in order for an end user to use clip applier 100, the end user must remove shipping wedge 200 thereby also removing tab 192a to activate counter mechanism 190.

As seen in FIGS. 1A and 1C, shipping wedge 200 includes a body portion 202 in the form of a collar, defining a passage 204 configured and dimensioned for receipt of a portion of housing 104 therein. Shipping wedge 200 includes uprights 206 extending outwardly from opposed sides of body portion 202 and being configured to receive handles 106 therein. Shipping wedge 200 further includes tabs 208 extending inwardly from opposed sides of uprights 206. Tabs 208 of shipping wedge 200 are configured and dimensioned to engage with handles 106 when shipping wedge 200 is properly secured to clip applier 100.

Figure 23:
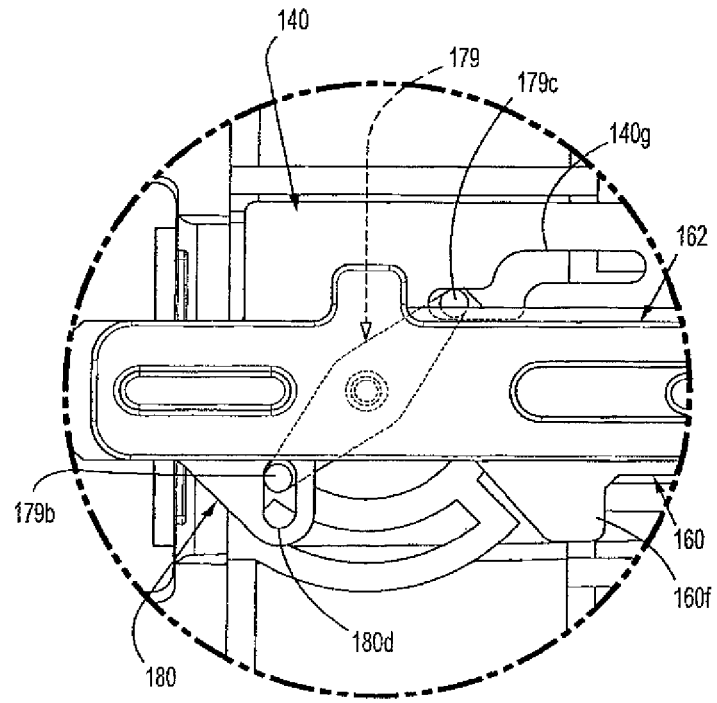
FIG. 23 is an enlarged view of the indicated area of detail of FIG. 22.
Figure 24:
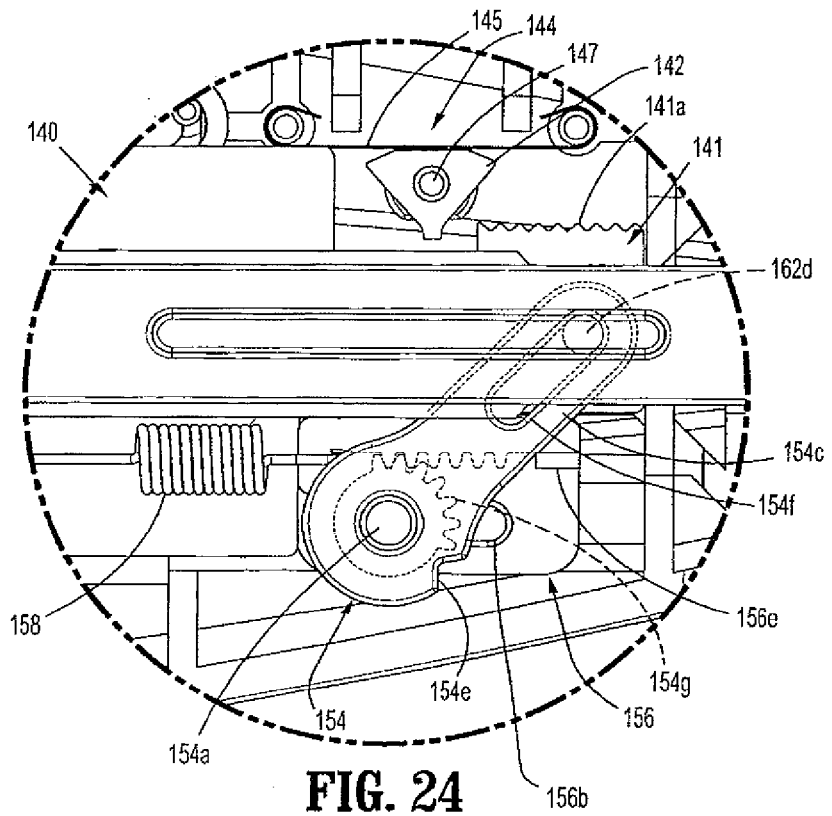
FIG. 24 is an enlarged view of the indicated area of detail of FIG. 22.

With reference to FIGS. 22-53, the operation of the Covidien SURGICLIP™ clip applier 100 is provided. Prior to any initial squeezing of handles 106 of clip applier 100, as seen in FIGS. 22-24, drive pin 124 is located at a proximal-most position, pawl 142 is located distal of rack 140d of drive channel 140, second finger 179c of pivot arm 179 is located at a distal-most position in the distal portion of window 140g of drive channel 140 such that wedge plate 180 is located at a distal-most position, and no clips "C" are positioned within jaws 120. Since drive pin 124 is at a proximal-most position, pusher bar 160, stabilizer 162, and drive channel 140 are also at a proximal-most position.

With drive channel 140 and pusher bar 160 located at a proximal-most position, accelerator rack 156 is located at a proximal-most position, and second resilient finger 148b of indicator 148 is disposed proximal of edge 149. Also, prior to an initial squeezing of handles 106 of clip applier 100, with wedge plate 180 located at a distal-most position, distal end 180a thereof is interposed between jaws 120.

Also prior to the initial squeeze, no clips "C" are present within jaws 120. A clip "C" is first loaded into jaws 120 during the initial squeezing of handles 106. As seen in FIGS. 25-33, during an initial squeezing of handles 106, distal ends 122a of link members 122 are caused to be moved distally relative to housing 104. As distal ends 122a of link members 122 are moved distally, drive pin 124 is caused to be moved distally thereby transmitting distal axial movement to drive channel 140.

As drive channel 140 is moved distally, biasing member 158 is moved distally therewith. As biasing member 158 is moved distally, biasing member 158 drags accelerator rack 156 in a distal direction. As accelerator rack 156 is dragged in a distal direction, accelerator rack 156 causes bell crank gear 154 to rotate about pivot pin 154a and transmit distal axial movement to nub 162d of stabilizer 162 which, in turn, transmits distal axial movement to pusher bar 160. As drive channel 140 is moved distally biasing member 146 is stretched or extended.

Figure 25:
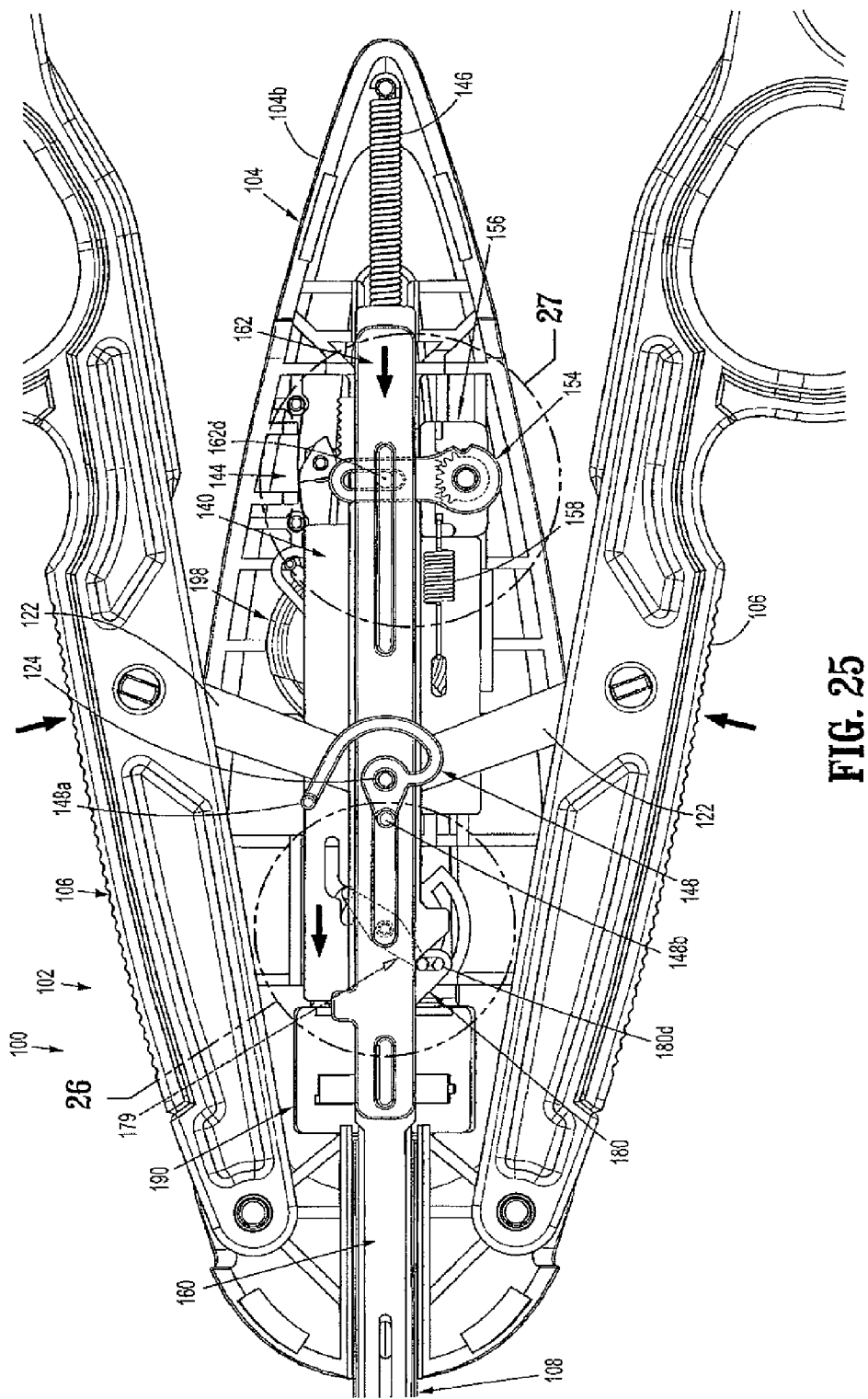
FIG. 25 is a top, plan view of the surgical clip applier of FIGS. 1-4, with the upper housing half removed therefrom and shown during an initial actuation thereof.
Figure 26:
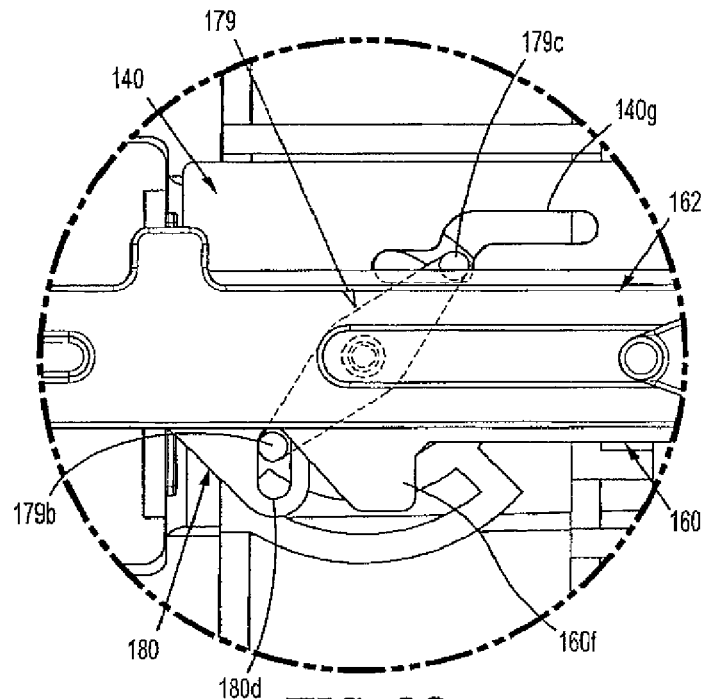
FIG. 26 is an enlarged view of the indicated area of detail of FIG. 25.
Figure 32:
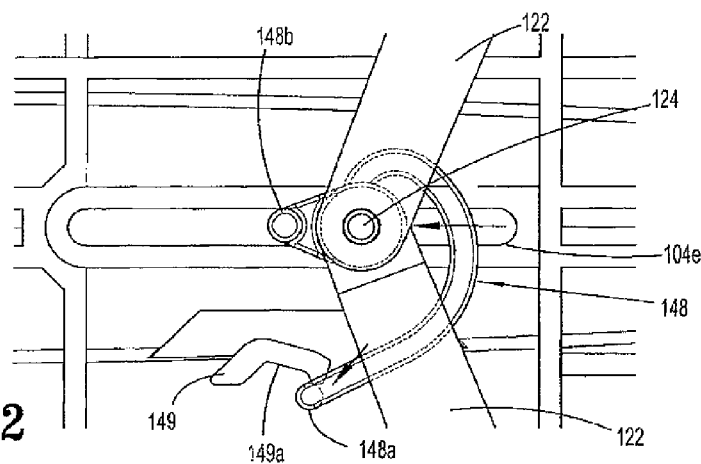
FIGS. 32 and 33 are enlarged view illustrating the operation of an audible/tactile indicator during the respective initial and further actuation of the surgical clip applier of FIGS. 1-4.
Figure 33:
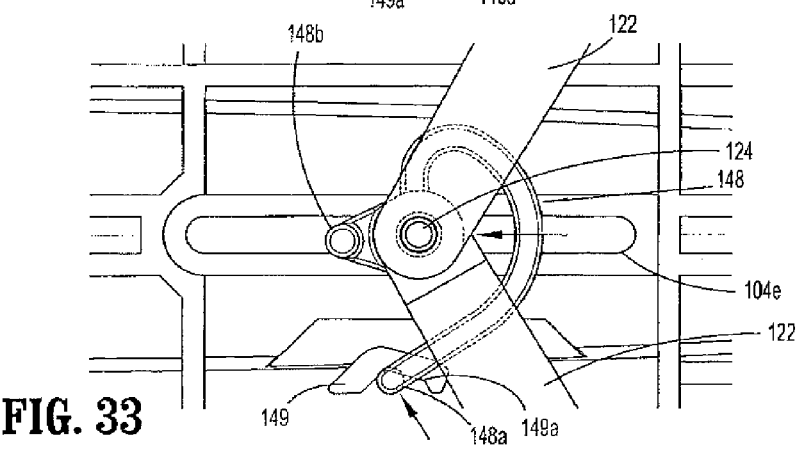
Figure 34:
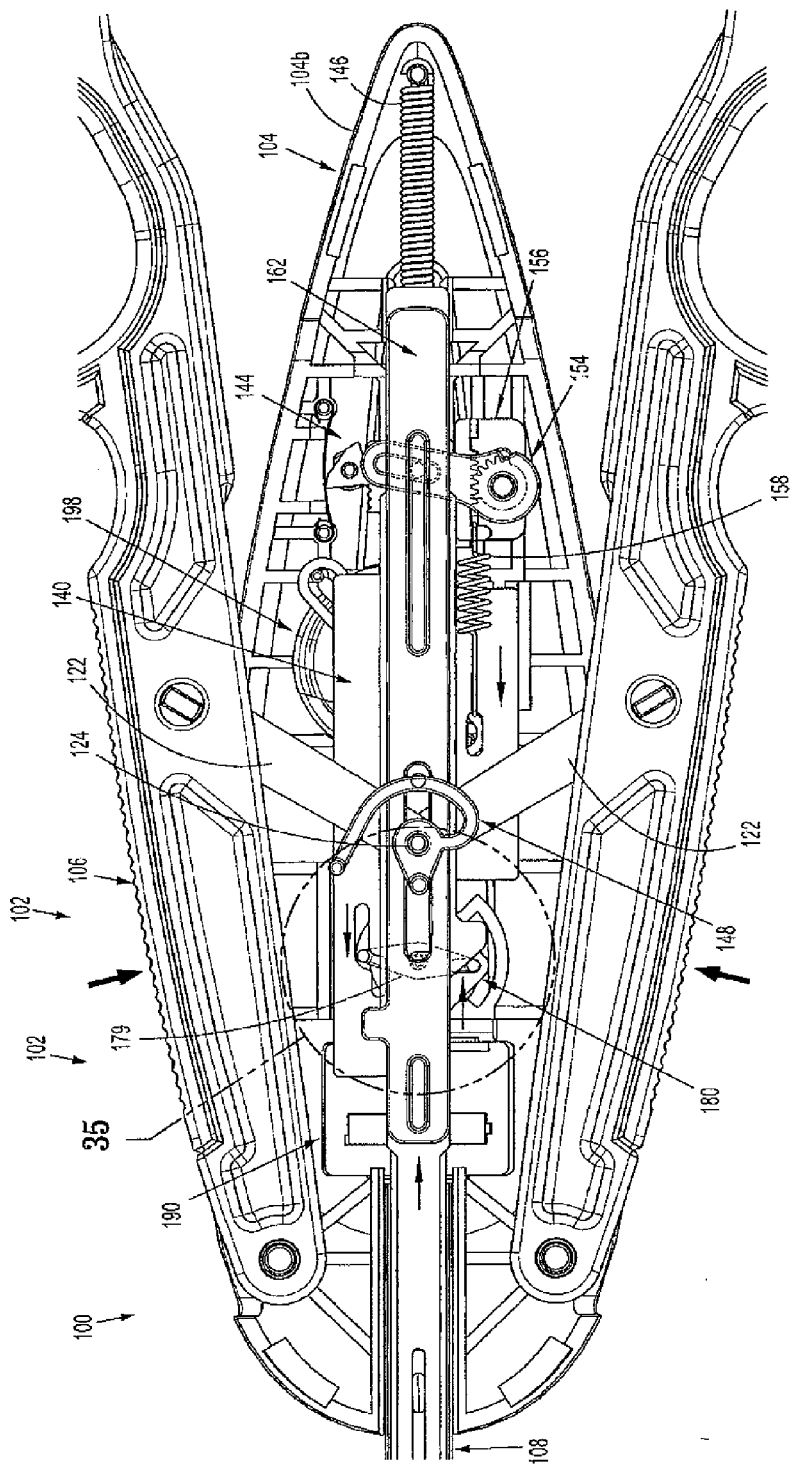
FIG. 34 is a top, plan view of the surgical clip applier of FIGS. 1-4, with the upper housing half removed therefrom and shown during a final actuation of the surgical clip applier.
Figure 35:
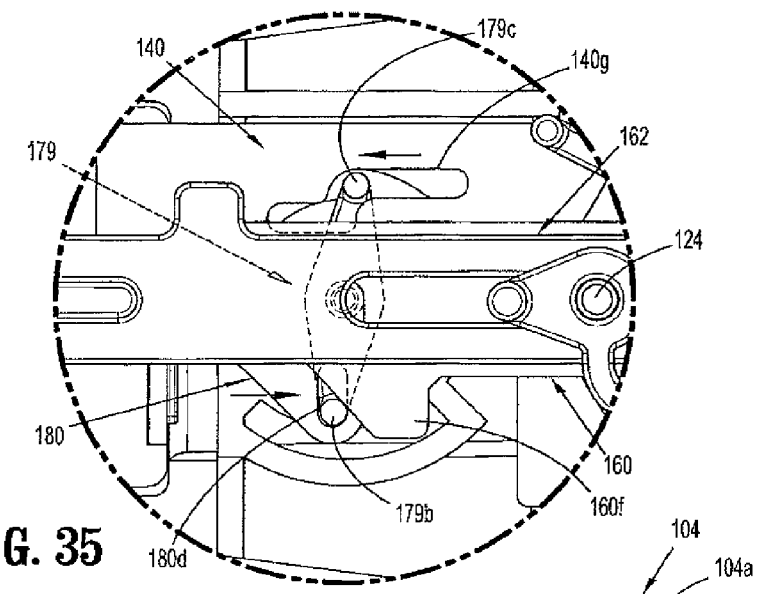
FIG. 35 is an enlarged view of the indicated area of detail of FIG. 34.

As seen in FIGS. 25, 32 and 33, during the initial squeeze of handles 106, indicator 148 is moved distally along with the distal movement of drive channel 140. In use, indicator 148 functions to create an audible click and/or a tactile vibration, thereby indicating to the user that handles 106 of surgical clip applier 100 have gone through at least a portion of a stroke. In particular, as seen in FIGS. 32 and 33, as handles 106 are actuated, first resilient arm 148a of audible/tactile indicator 148 rides over and/or along a ledge 149 formed in at least one of upper and lower housing halves 104a, 104b and is flexed thereby. As arm 148a of audible/tactile indicator 148 reaches the proximal end of ledge 149, resilient arm 148a snaps over the proximal end of ledge 149 and comes into contact with a surface 149a of ledge 149, thereby creating a first audible sound and a tactile vibration as resilient arm 148a comes into contact with surface 149a of ledge 149. The first indication of audible/tactile indicator 148 indicates to the user that a clip "C" has been appropriately loaded.

Figure 28:
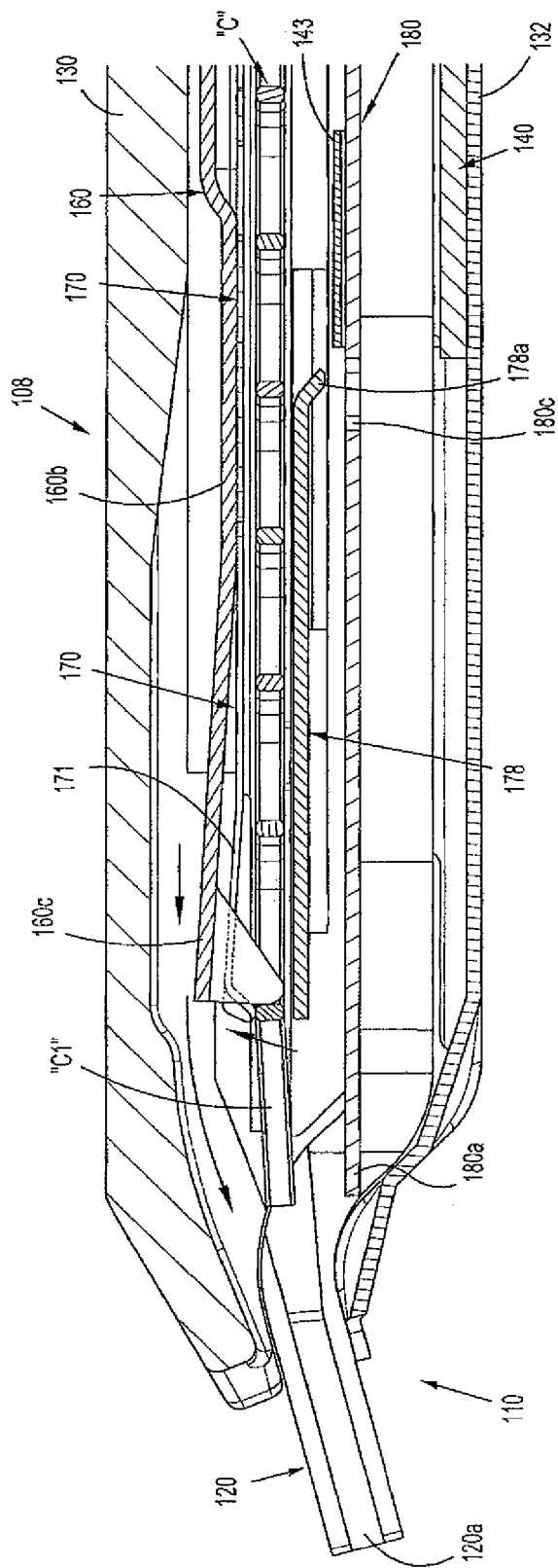
FIG. 28 is an enlarged, longitudinal cross-sectional view of the distal end of the channel assembly during the initial actuation of the surgical clip applier.
Figure 29:
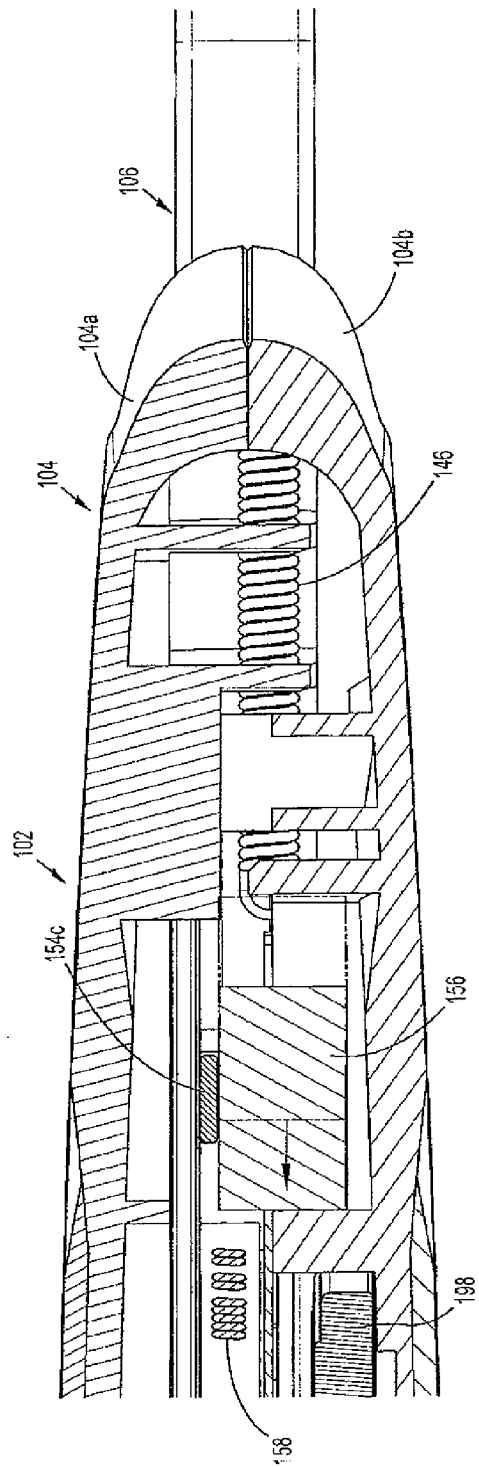
FIG. 29 is a cross-sectional view as taken through 29-29 of FIG. 27.
Figure 30:
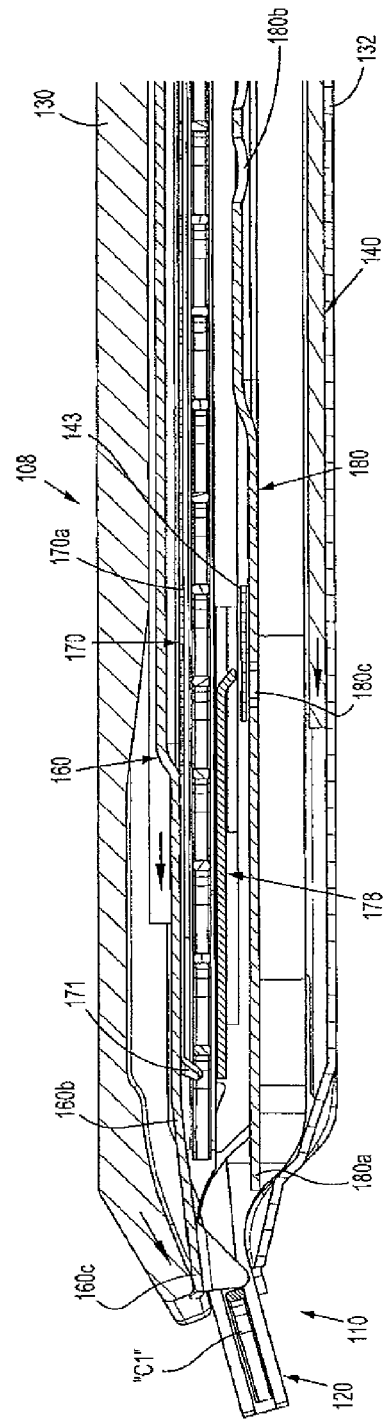
FIG. 30 is an enlarged, longitudinal cross-sectional view of the distal end of the channel assembly during a further initial actuation of the surgical clip applier.

As seen in FIGS. 28 and 30, also during the initial squeeze of handles 106, as pusher bar 160 is moved in a distal direction, pusher 160c thereof engages a backspan of a distal-most clip "C1" and begins to move or urge distal-most clip "C1" distally out of clip carrier 170 and into jaws 120. As distal-most clip "C1" is moved distally, tangs 171 of clip carrier 170 are deflected or cammed out of engagement with distal-most clip "C1" and return to their un-deflected or un-cammed state to capture a subsequent clip of the stack of clips "C". During the initial squeeze of handles 106, pusher bar 160 is advanced an amount sufficient to place distal-most clip "C1" in channels 120a of jaws 120.

Figure 27:
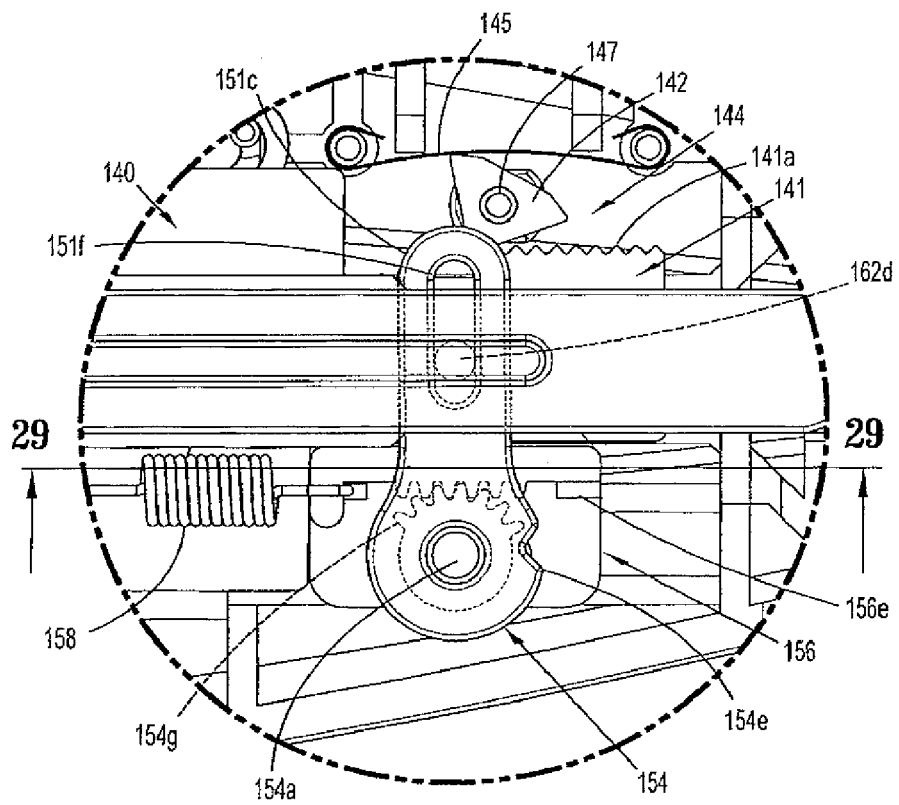
FIG. 27 is an enlarged view of the indicated area of detail of FIG. 27.
Figure 31:
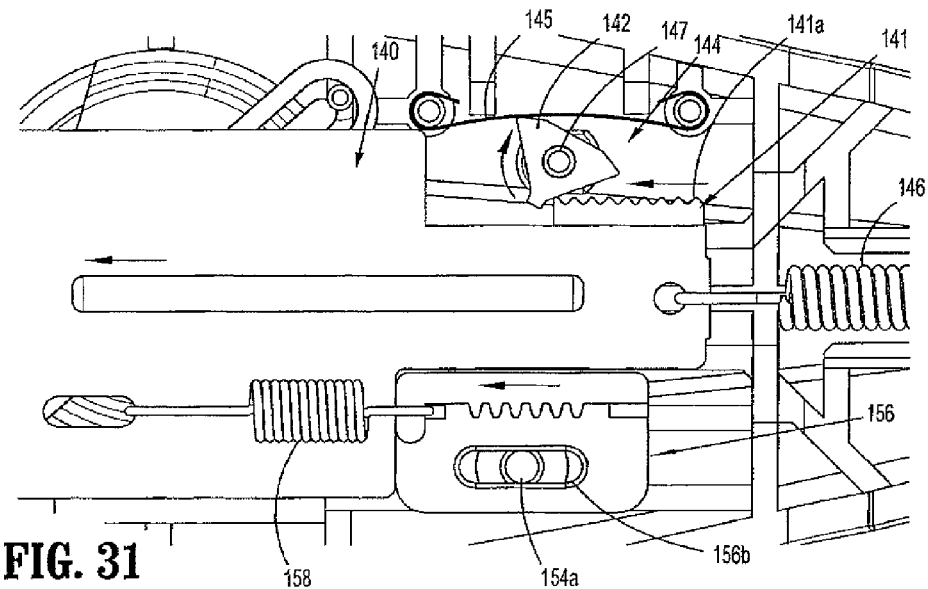
FIG. 31 is an enlarged view of illustrating the operation of a ratchet assembly and accelerator rack of the surgical clip applier of FIGS. 1-4.

As seen in FIGS. 27 and 31, also during the initial squeeze of handles 106, as drive channel 140 is moved in a distal direction, rack member 141 of ratchet mechanism 144 is moved distally causing teeth 141a thereof to move into engagement with and over or across a tooth of pawl 142. Once rack member 141 of ratchet mechanism 144 is moved into engagement with pawl 142, drive channel 140 can not return to a home or proximal-most position until rack member 141 has cleared pawl 142.

During the initial squeeze of handles 106, as seen in FIGS. 25-33, drive channel 140 is moved distally until finger 179c of pivot arm 179 is engaged by the transverse portion of slot 140g of drive channel 140 (i.e., the dwell). Once the transverse portion of slot 140g is in abutment with finger 179c of pivot arm 179 (i.e., after the dwell has been exhausted), further distal movement of drive channel 140 causes finger 179c to move and rotate pivot arm 179. Rotation of pivot arm 179 causes movement of finger 179b thereof which, in turn, causes wedge plate 180 to be pulled in a proximal direction, thereby withdrawing distal end 180a thereof from between jaws 120 and allowing for jaws 120 to eventually be closed or approximated, and pushes on fin 160f of pusher bar 160 to urge pusher bar 160 in a proximal direction such that distal end pusher member 160c thereof is also moved from between jaws 120 thus allowing for jaws 120 to eventually be closed or approximated.

Once the required rotation of pivot arm 179 is achieved, pivot arm 179 stops rotating as finger 179c of pivot arm 179 rides through the proximal portion of slot 140g of drive channel 140. Finger 179c of pivot au 179 remains in the proximal portion of slot 140g of drive channel 140 until the stroke of drive channel 140 is completed.

Figure 38:
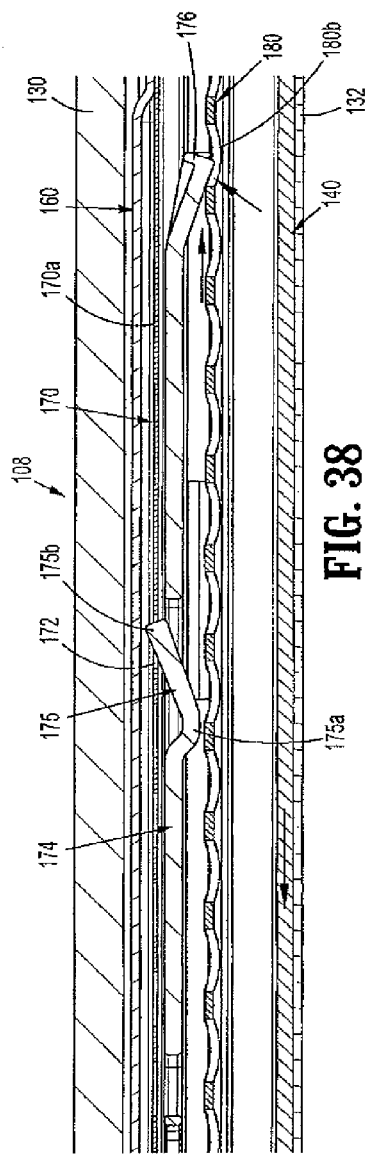
FIG. 38 is an enlarged, cross-sectional view of the channel assembly illustrating the clip follower during the final actuation of the surgical clip applier of FIGS. 1-4.
Figure 39:
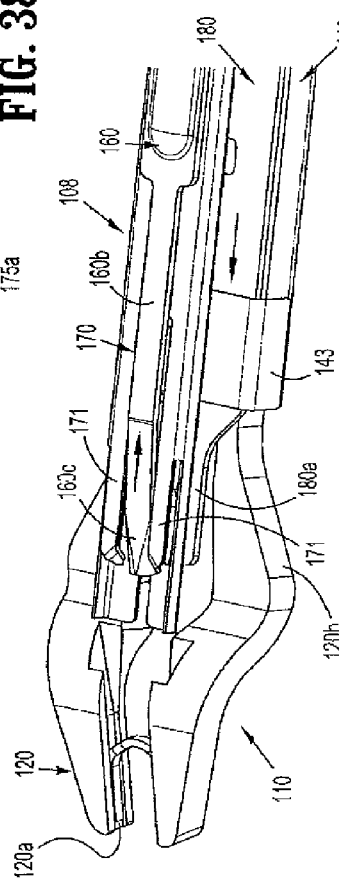
FIGS. 39 and 40 are enlarged perspective view, illustrating the distal end of the channel assembly during the final actuation of the surgical clip applier of FIGS. 1-4.
Figure 40:
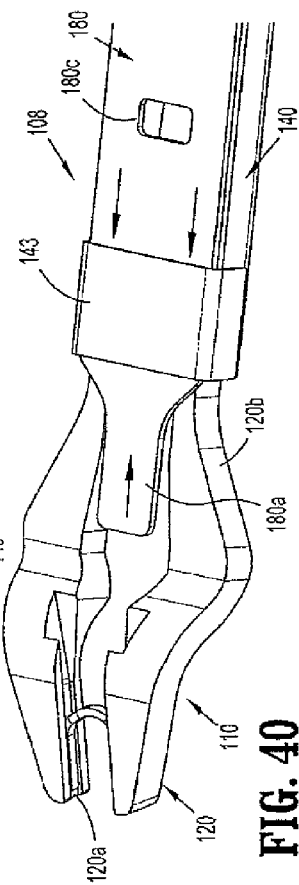
Figure 41:
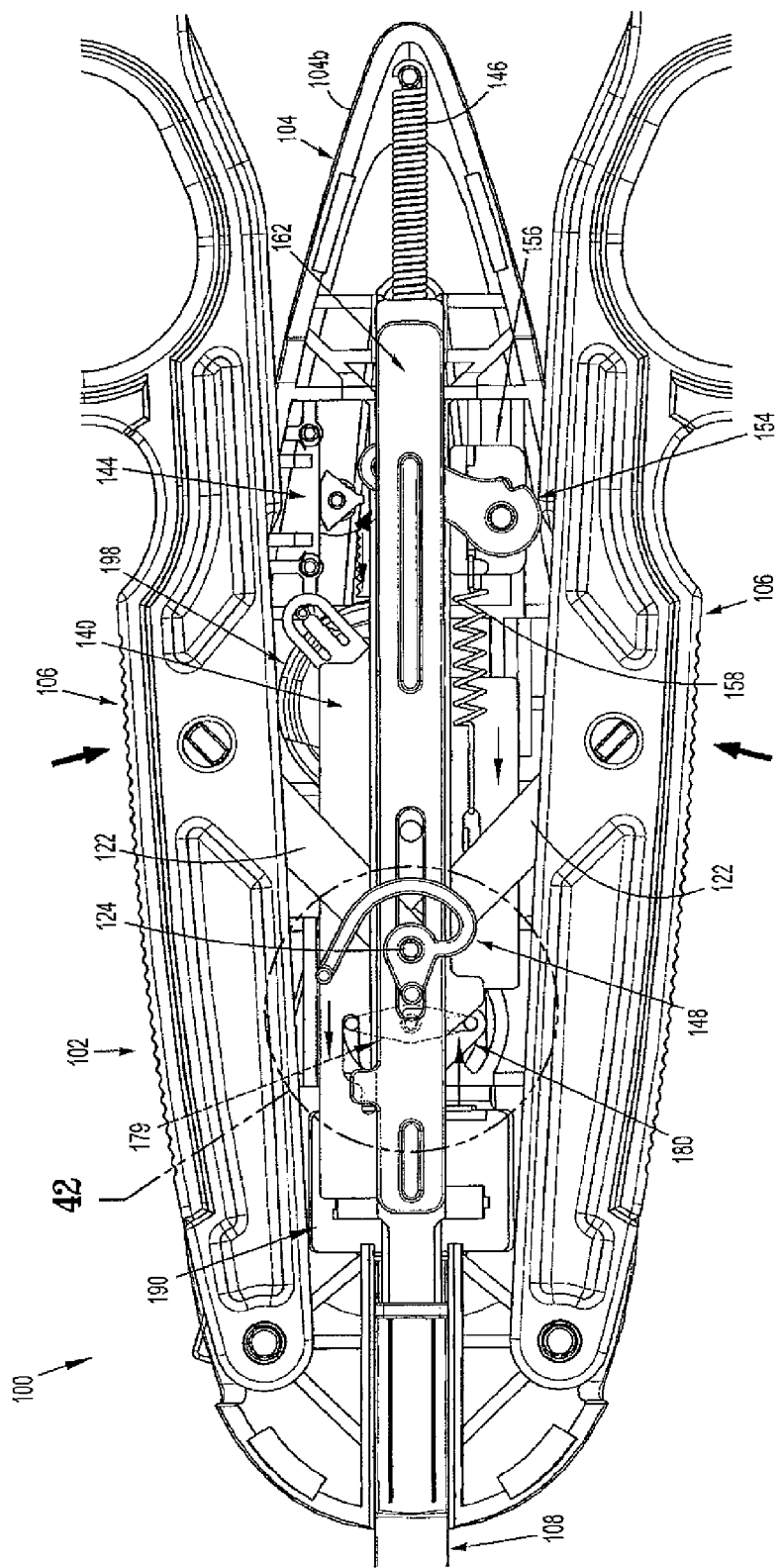
FIG. 41 is a top, plan view of the surgical clip applier of FIGS. 1-4, with the upper housing half removed therefrom and shown at a final condition after an actuation of the surgical clip applier.
Figure 42:
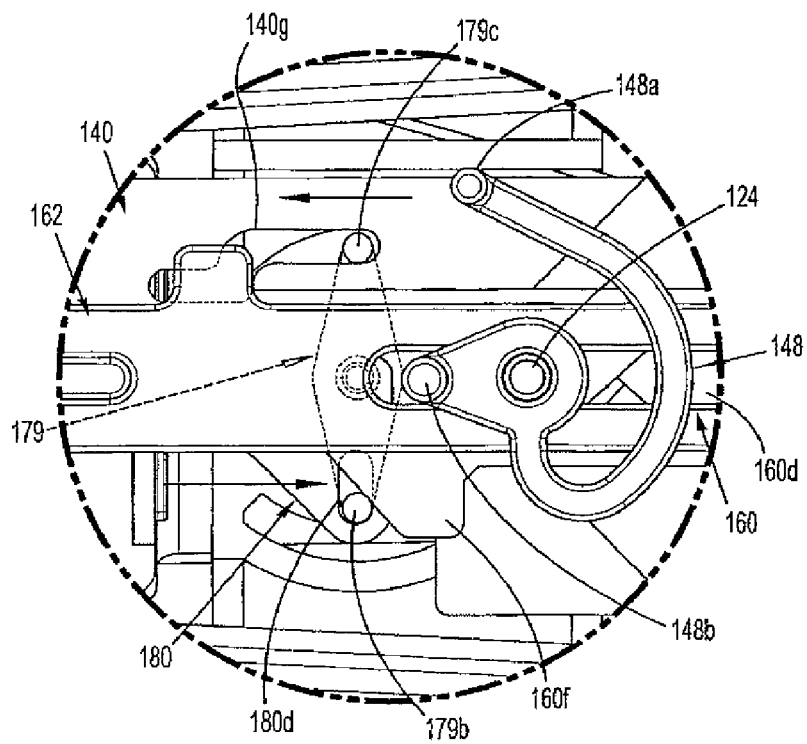
FIG. 42 is an enlarged view of the indicated area of detail of FIG. 41.

As seen in FIG. 38, as wedge plate 180 is moved in a proximal direction, wedge plate 180 is moved proximally relative to clip follower 174 thereby moving windows 180b thereof proximally relative to proximal tab 176 of clip follower 174.

As seen in FIGS. 28 and 30, during the initial squeeze of handles 106, pusher bar 160 is moved distally with drive channel 140, as described above, until accelerator rack 156 abuts against a rib in lower body 104b of housing 104, at which time distal advancement of accelerator rack 156 is stopped. With accelerator rack 156 prevented from further distal advancement, as seen in FIG. 32, as drive channel 140 is further advanced distally, drive channel 140 pulls or flexes resilient finger 148a of indicator 148 over a proximal end of ledge 149. In this manner, a first indication (i.e., audible and/or tactile) is created indicating to a user that a surgical clip "C" has been appropriately loaded. Also, with accelerator rack 156 prevented from further distal advancement, bell crank 154 is prevented from rotating and thus pusher bar 160 is prevented from further distal advancement.

Referring now to FIGS. 34-40, during a further squeezing of handles 106, distal-ends 122a of link members 122 are caused to be moved further distally relative to housing 104. As distal ends 122a of link members 122 are moved further distally, drive pin 124 is caused to be moved further distally thereby transmitting distal axial movement to drive channel 140.

As seen in FIGS. 34-40, as drive channel 140 is moved further distally, pusher bar 160 is prevented from further distal advancement by accelerator rack 156 abutting against the rib formed in the lower body 104b of housing 104. With accelerator rack 156 stopped from distal advancement, further rotation of bell crank gear 154 is stopped, which in turn stops distal advancement of stabilizer 160 and, in turn, stops distal advancement of pusher bar 160.

Figure 44:
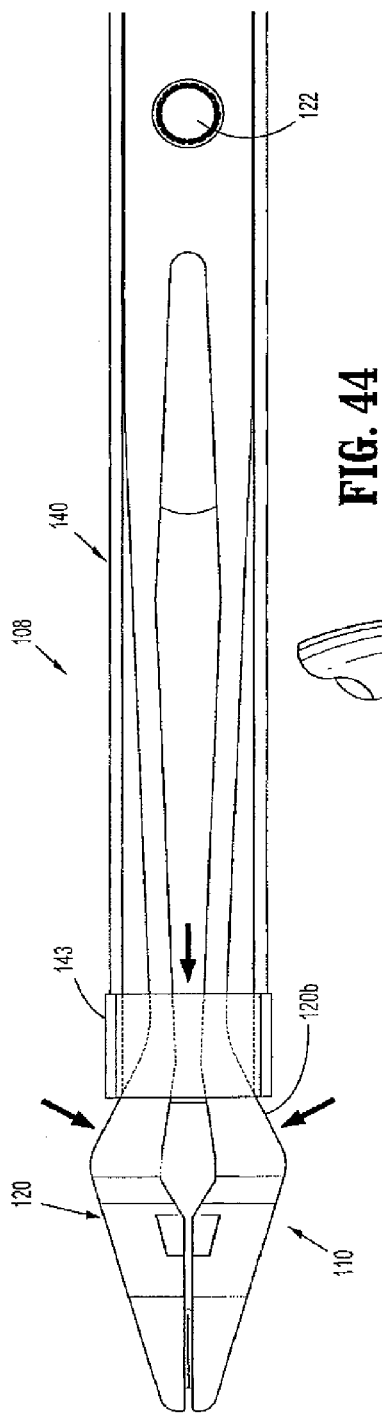
FIG. 44 is a top, plan view of the jaw assembly illustrating the position of the jaw assembly following an actuation of the surgical clip applier of FIGS. 1-4.

Additionally, as seen in FIG. 44, with distal end 180a of wedge plate 180 removed from between jaws 120, as drive channel 140 is moved further distally, a distal edge of drive channel 140 and/or drive channel strap 143 engages against camming surfaces 120b of jaws 120 thus causing jaws 120 to approximate toward one another and to form surgical clip "C1" interposed therebetween. Since drive channel strap 143 is fixed to drive channel 140 and moves therewith, drive channel strap 143 functions to cap drive channel 140 so as to maintain jaws 120 within drive channel 140 during the approximation of jaws 120 and to maintain wedge plate 180 within drive channel 140 during operation of clip applier 100.

Figure 45:
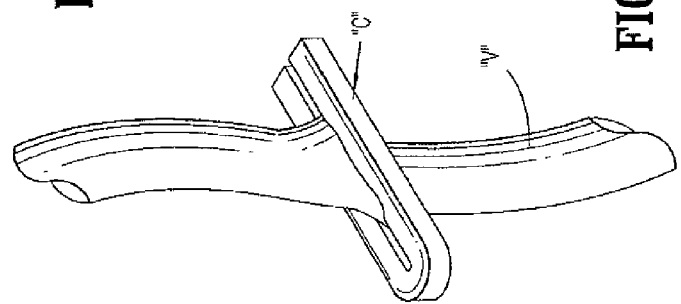
FIG. 45 is a perspective view of a body vessel including a clip of the surgical clip applier, shown applied thereto.
Figure 46:
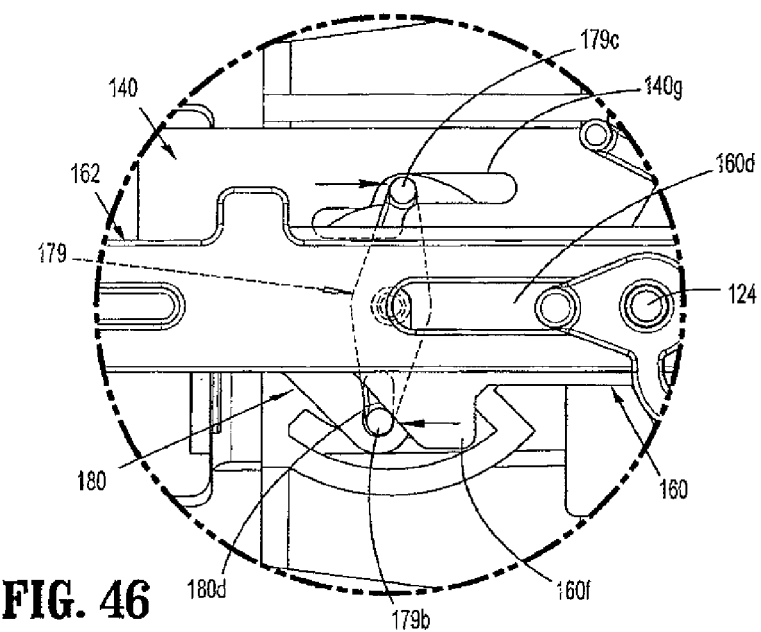
FIG. 46 is an enlarged view of the indicated areas of detail of FIGS. 34 and 41, illustrating the operation of the pivot arm during an opening or release of the surgical clip applier following a complete actuation thereof.
Figure 47:
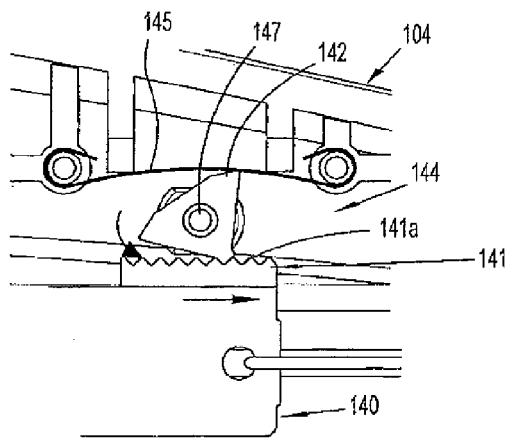
FIG. 47 is an enlarged view of the ratchet mechanism shown during the opening or release of the surgical clip applier of FIGS. 1-4.

As seen in FIG. 45, surgical clip "C1" may be formed or crimped onto a vessel "V" or any other biological tissue.

Drive channel 140 is permitted to move distally relative to pusher bar 160 due to the translation of bosses 148b of indicator 148 through slot 160d of pusher bar 160.

Figure 37:
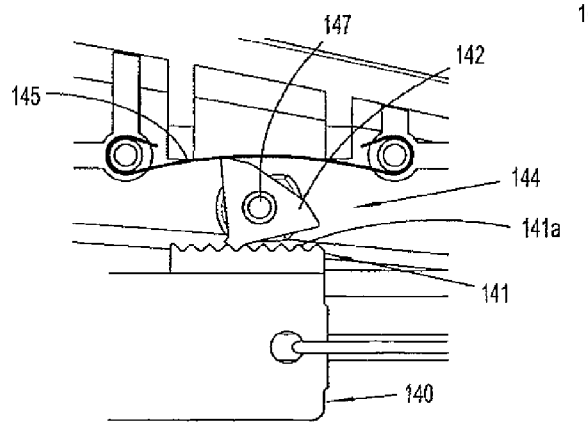
FIG. 37 is an enlarged view of a ratchet mechanism shown during the final actuation of the surgical clip applier of FIGS. 1-4.

Also, as drive channel 140 is fully advanced distally, as seen in FIG. 37, rack member 141 of ratchet mechanism 144 is moved distally to a location beyond pawl 142 such that the teeth 141a of rack member 141 are moved distally of the tooth of pawl 142 thereby disengaging rack member 141 and pawl 142 from one another. In this manner, drive channel 140 is permitted or free to return to a home or proximal-most position.

As seen in FIGS. 32 and 33, as drive channel 140 is moved distally, resilient arm 148a of audible/tactile indicator 148 snaps over the distal end of ledge 149 and comes into contact with a surface 149a of ledge 149, thereby creating an audible sound and/or a tactile vibration. Such audible sound and/or tactile vibration coincide with the loading of surgical clip "C".

Figure 43:
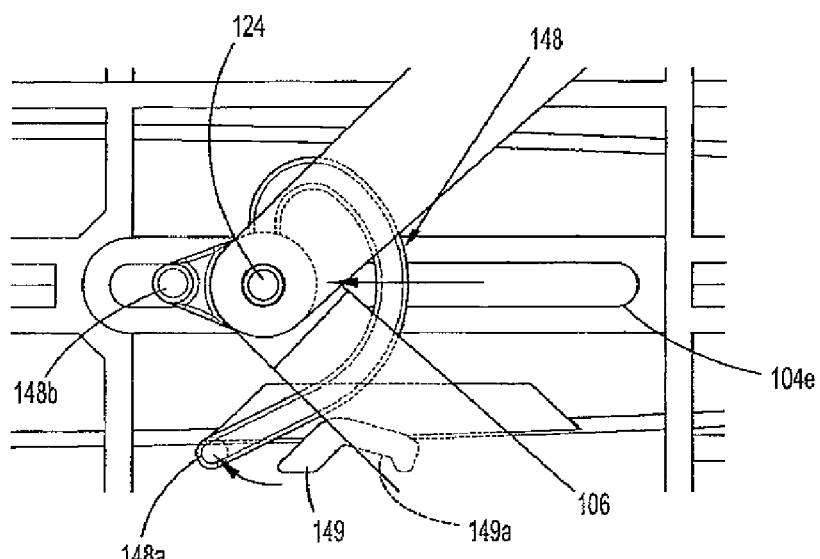
FIG. 43 is an enlarged view illustrating the position of the audible/tactile indicator following an actuation of the surgical clip applier of FIGS. 1-4.

As seen in FIG. 43, as drive channel 140 is further moved distally, resilient arm 148a of audible/tactile indicator 148 snaps over the distal end of ledge 149 thereby creating a further audible sound and/or a tactile vibration. Such audible sound and/or tactile vibration coincide with the complete formation of surgical clip "C".

With continued reference to FIG. 35-40, during the further squeezing of handles 106, with tab 192a removed from counter mechanism 190, as drive channel 140 is advanced distally, nub 140e thereof engages contact 194a of processor 194 thereby completing a circuit and causing processor 194 to perform a function, as described above.

Referring now to FIGS. 41-45, clip applier 100 is illustrated following a complete stroke or squeezing of handles 106 and during an opening of handles 106. In this condition, drive channel 140 is at a distal position, pusher bar 160 is at a distal position, wedge plate 180 is at a proximal position, accelerator 156 is spaced a distance from drive channel 140, each biasing member 146 and 158 are stretched, and pawl 142 is located proximal of rack 140d.

As seen in FIGS. 46-52, during an opening or release of handles 106, distal ends 122a of link members 122 are caused to be moved proximally relative to housing 104. As distal ends 122a of link members 122 are moved proximally, drive pin 124 is caused to be moved proximally thereby transmitting proximal axial movement to drive channel 140 and, in turn, pusher bar 160. The proximal movement of drive channel 140 is facilitated by the constriction of biasing members 146. Alternatively, the release of handles 106 results in biasing member 146 withdrawing drive channel 140 in a proximal direction.

As drive channel 140 is moved proximally, the distal edge of drive channel 140 and/or drive channel strap 143 disengages from against camming surfaces 120b of jaws 120 thus freeing jaws 120 for separation from one another for reinsertion of distal end 180a of wedge plate 180 therebetween, and to receive another surgical clip "C" therebetween. In particular, as drive channel 140 is moved proximally, the transverse portion of slot 140g acts on finger 179c to cause pivot arm 179 to rotate and cause finger 179b of pivot arm 179 to urge wedge plate 180 distally. As wedge plate 180 is moved in a distal direction, as seen in FIGS. 51 and 52, distal end 180a of wedge plate 180 is reinserted or reintroduced into jaws 120, thereby spreading jaws 120 apart.

Figures 49, 50:
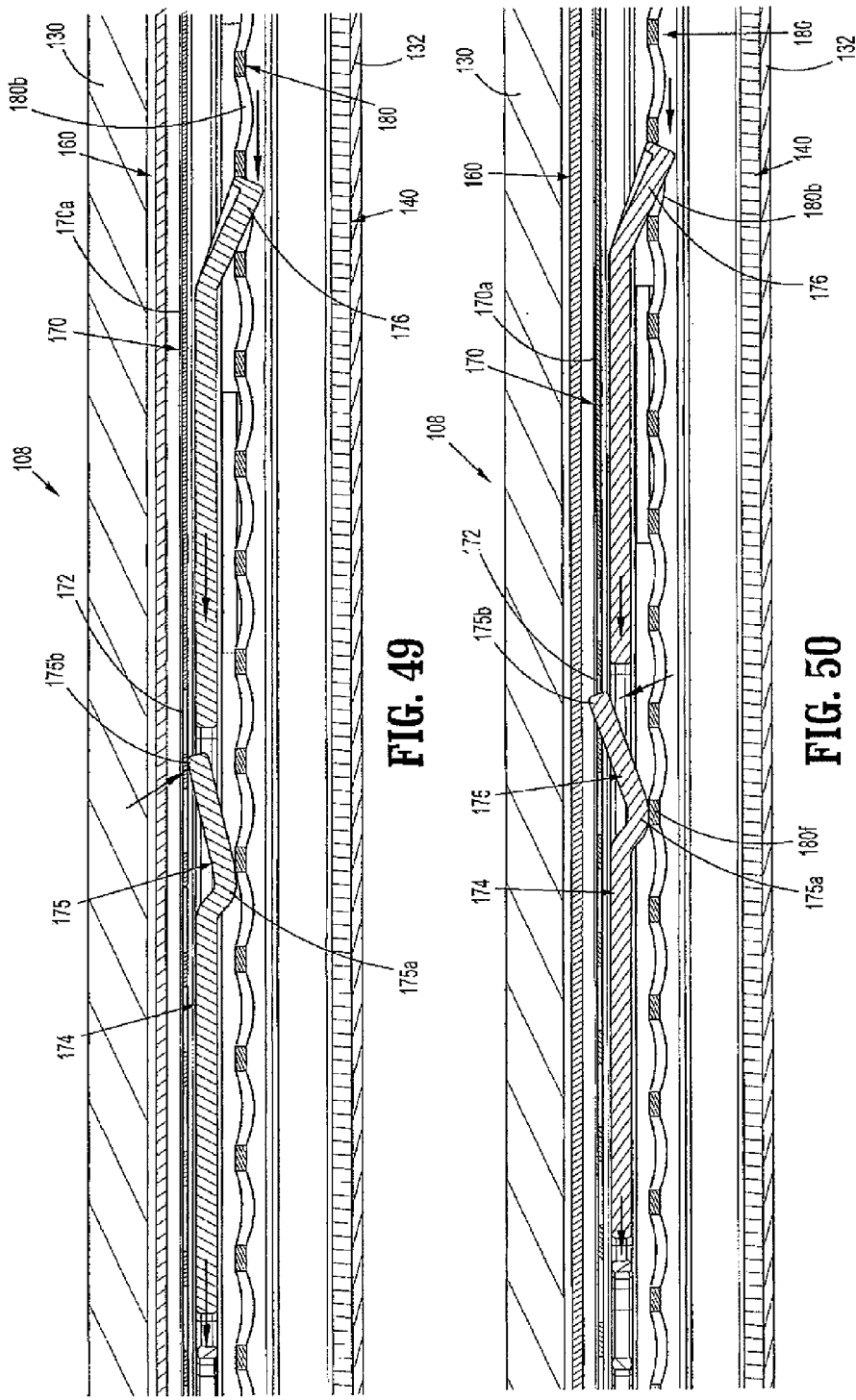
FIGS. 49 and 50 are longitudinal, cross-sectional views of the channel assembly illustrating the movement of the clip follower during the opening or release of the surgical clip applier of FIGS. 1-4.

As seen in FIGS. 49 and 50, as wedge plate 180 is moved distally, proximal tab 176 of clip follower 174 engages in a window 180b of wedge plate 180 and is thus urged distally a given distance. As clip follower 174 is urged distally, stack of clips "C" is also urged distally. As seen in FIG. 50, when wedge plate 180 reaches a distal-most position, clip channel 170 abuts, engages, urges or otherwise cams against proximal portion 175b of distal tab 175 until web 180f of wedge plate 180 rests substantially beneath distal portion 175a of distal tab 175. In so doing, proximal portion 175b of distal tab 175 is moved to extend into an incrementally more distal window 172 of clip channel 170.

Figure 51:
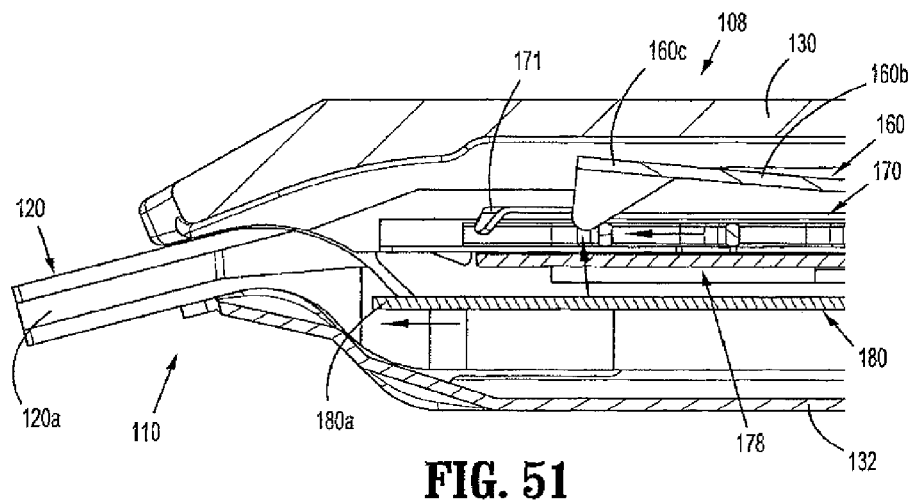
FIGS. 51 and 52 are longitudinal, cross-sectional views of the distal end of the channel assembly illustrating the movement of the pusher bar and wedge plate during the opening or release of the surgical clip applier of FIGS. 1-4.
Figure 52:
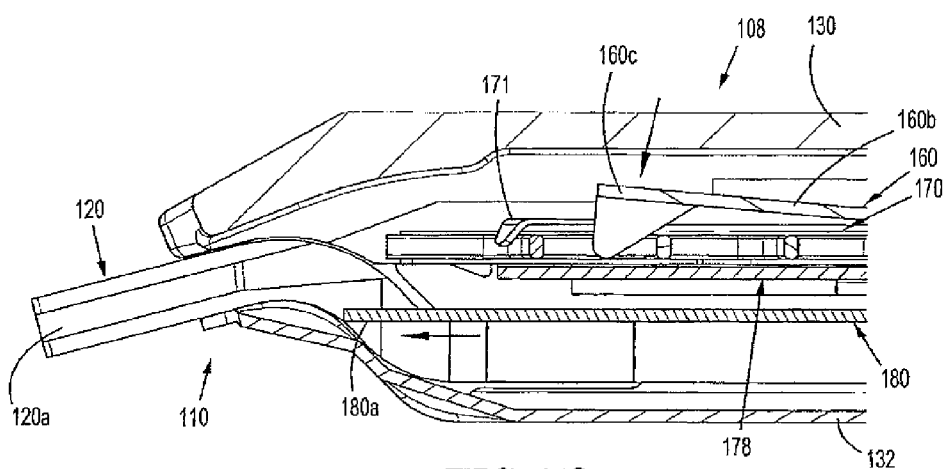

As seen in FIGS. 51 and 52, as clip follower 174 is urged forward, moving the stack of clips "C" forward, a distal-most clip "C1" moves distal of pusher 160c by camming beneath pusher 160c of pusher bar 160 until distal-most clip "C1" is caught by tangs 171 of clip applier 170.

Figure 48:
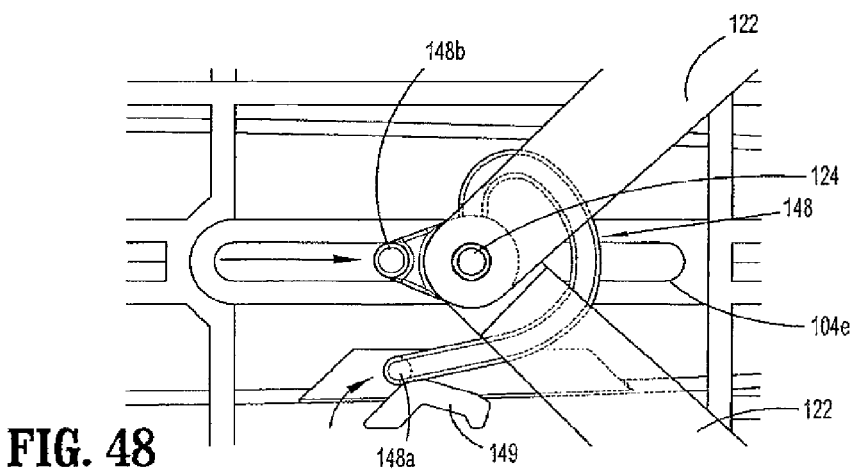
FIG. 48 is an enlarged view illustrating the operation of the audible/tactile indicator during the opening or release of the surgical clip applier of FIGS. 1-4.

Turning momentarily to FIG. 48, as drive channel 140 is moved in a proximal direction, arm 148a of audible/tactile indicator 148 snaps back over ledge 149 and re-sets itself for the next firing stroke or squeeze of handles 106.

As drive channel 140 is moved further in a proximal direction, drive channel 140 engages against accelerator rack 156 causing accelerator rack 156 to move in a proximal direction. Movement of accelerator rack 156 in a proximal direction results in rotation of bell crank gear 154 about pivot pin 152a to thereby move pusher bar 160 in a proximal direction. Additionally, as drive channel 140 is moved in a proximal direction, nub 140e thereof disengages contact 194a of processor 194.

Figure 53:
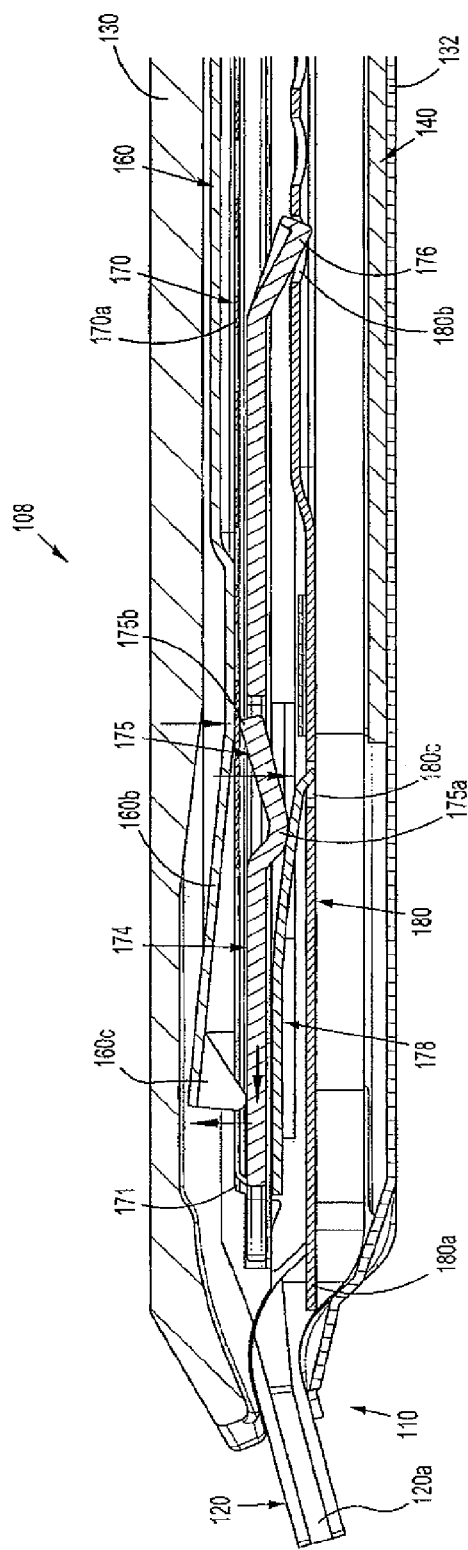
FIG. 53 is a longitudinal, cross-sectional view of the distal end of the channel assembly illustrating the surgical clip applier of FIGS. 1-4 in a locked-out condition following firing of the last surgical clip therefrom.
Figure 54:
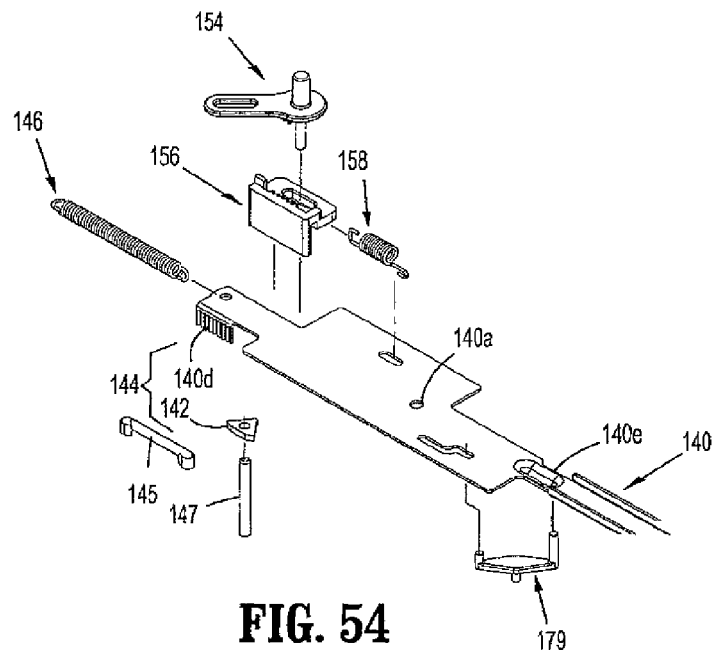
FIG. 54 is a perspective view of a drive channel including an integral ratchet rack according to an alternate embodiment of the present disclosure.
Figure 55:
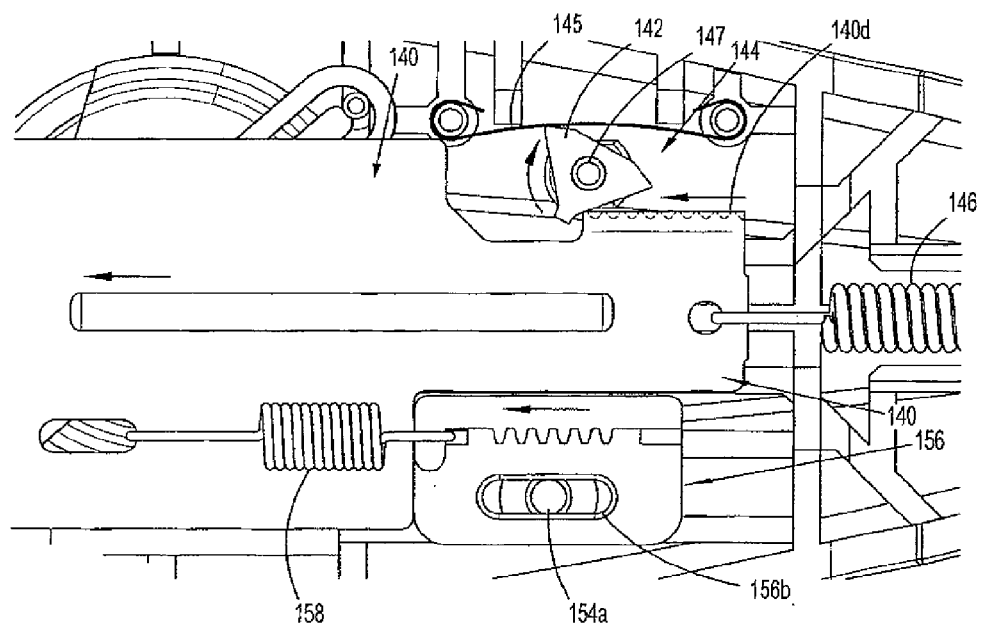
FIGS. 55-57 are enlarged schematic illustrations of the operation of a ratchet mechanism of the surgical clip applier including the drive channel of FIG. 54.
Figure 56:
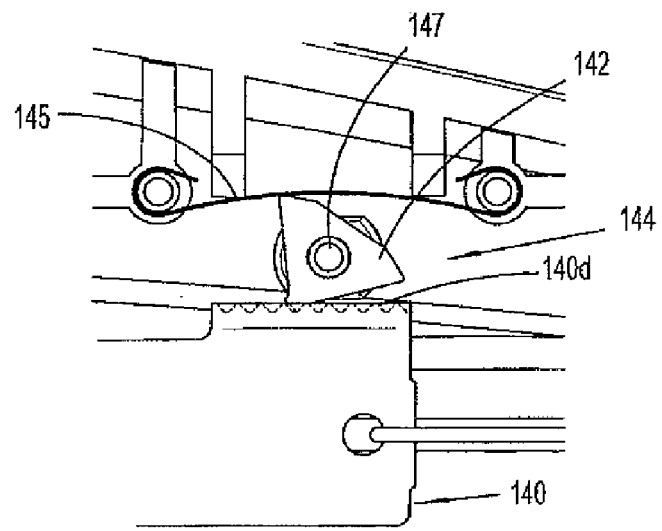
Figure 57:
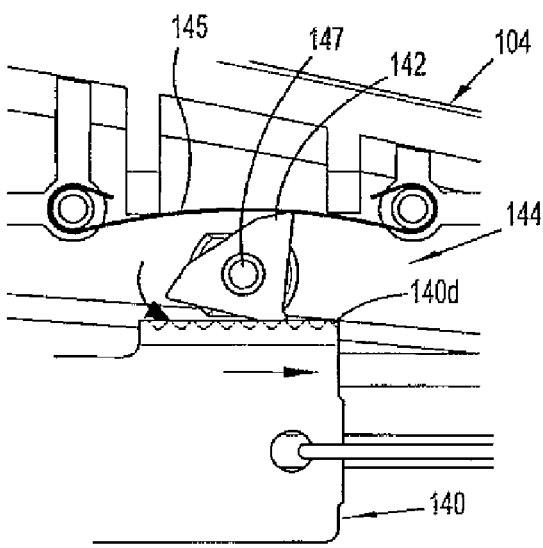
Figure 58:
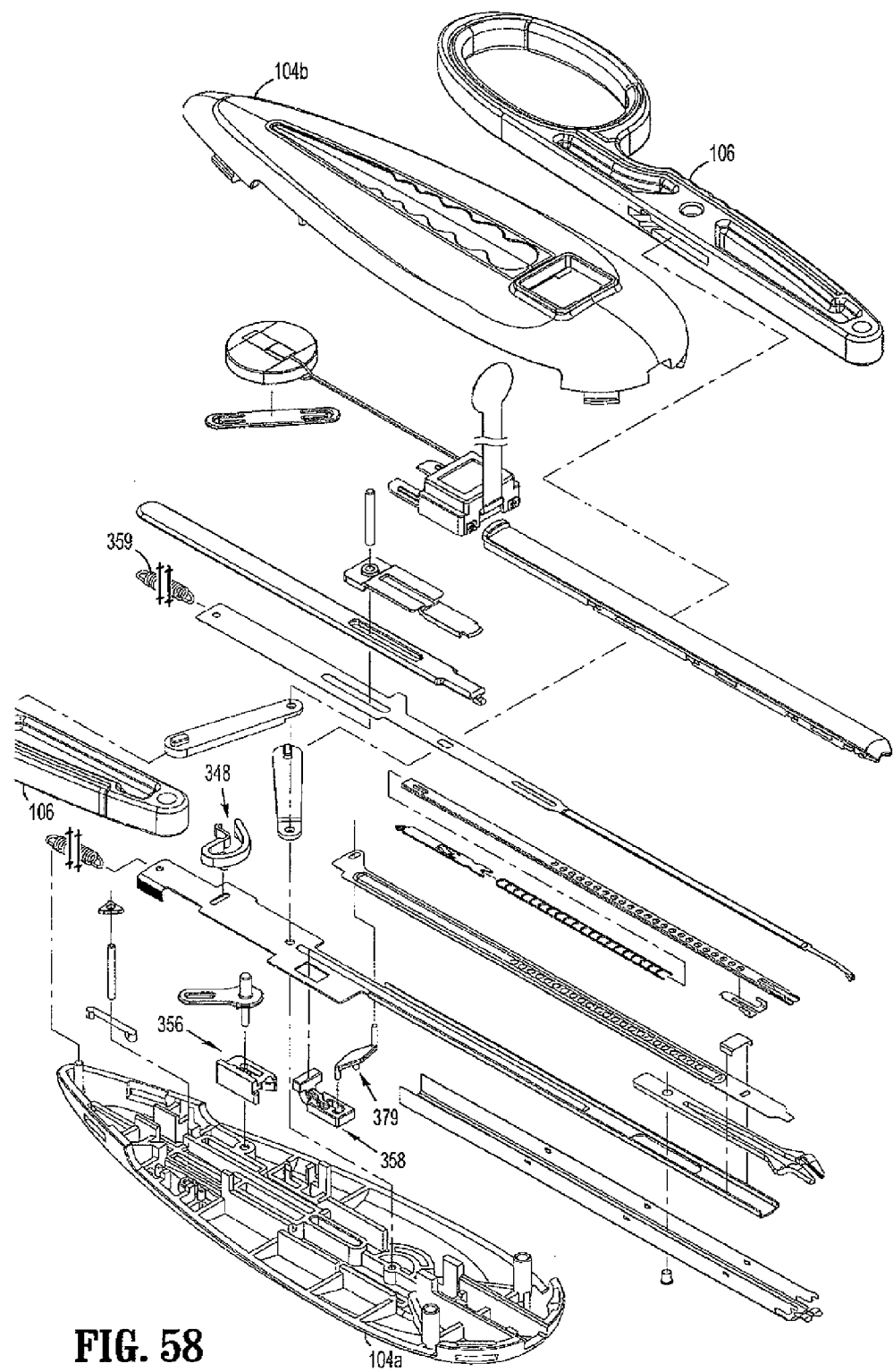
FIG. 58 is an exploded perspective view of a surgical clip applier according to another embodiment of the present disclosure.
Figure 59:
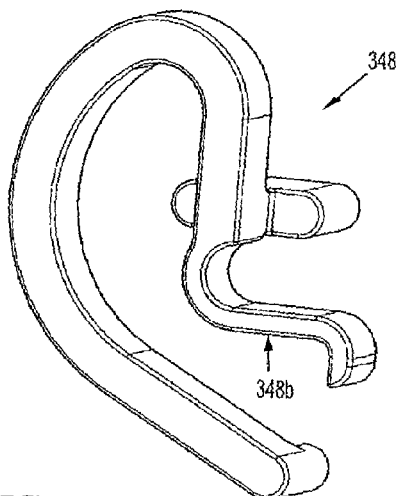
FIG. 59 is a perspective view of an audible/tactile indicator of the surgical clip applier of FIG. 58.
Figure 60:
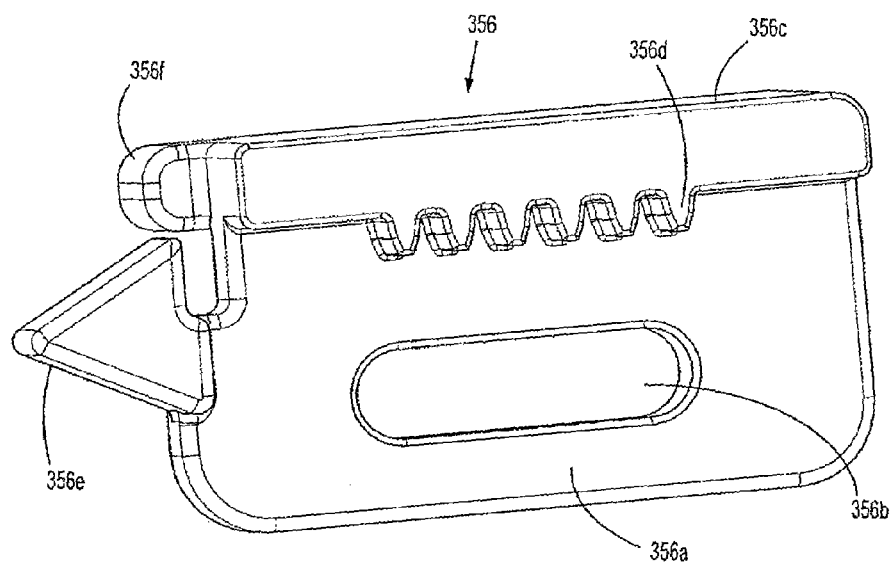
FIG. 60 is a perspective view of an accelerator rack of the surgical clip applier of FIG. 58.
Figure 61:
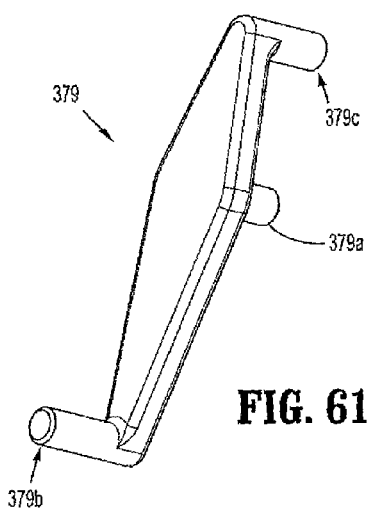
FIG. 61 is a perspective view of a pinot arm of the surgical clip applier of FIG. 58.
Figure 62:
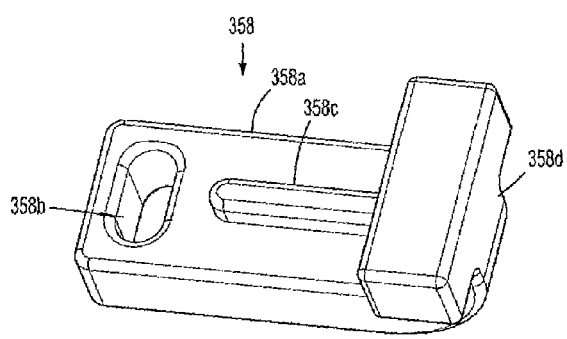
FIG. 62 is a perspective view of a first arm link for the surgical clip applier of FIG. 58.
Figure 63:
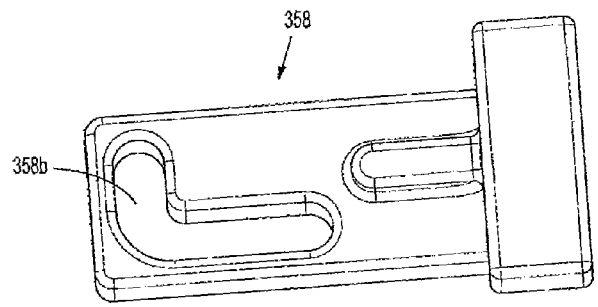
FIG. 63 is a perspective view of a second arm link for the surgical clip applier of FIG. 58.

Turning now to FIG. 53, a distal end of clip applier 100 is illustrated following a complete stroke or squeezing of handles 106 and after a final clip has been expelled therefrom. Following firing of the last clip, as seen in FIG. 53, proximal tab 176 of clip follower is disposed within a distal-most aperture or window of apertures 180b of wedge plate 180. In this manner, as wedge plate 180 is moved distally following a firing of a clip, in the manner described above, clip follower 174 is also moved distally. Accordingly, as clip follower 174 is moved distally, distal tab 175 thereof is moved distal of a distal-most window of windows 172 of clip carrier 170. In this manner, proximal portion 175b of distal tab 175 engages against an inner surface of a top wall of clip carrier 170 and is cammed or urged downwardly.

As proximal portion 175b of distal tab 175 is cammed or urged downwardly, distal portion 175a of distal tab 175 engages against an upper surface of tab 178a of lockout 178 and cams or urges tab 178a of lockout 178 downwardly, across a path of strap 143, supported on drive channel 140, and into distal window 180c of wedge plate 180. In this manner, if drive channel 140 is advanced distally, in the manner described above, strap 143 will abut against tab 178a of lockout 178 and prevent or block strap 143 and, in turn, drive channel 140 from moving distally. At this stage, pawl 142 is located in a dwell, distal of rack 140d, and handles 106 are arranged in a fully opened position and are thus not capable of being opened any further. In this configuration, clip applier is locked out and can no longer be used.

Depending on the size of the surgical clip, the size of components of clip applier 100 will have to be scaled accordingly. The majority of the components of the various sized clip appliers will be substantially identical to one another. Components size relating to the width of the clips, such as the jaws 120 and the wedge plate 180, or components size relating to the length of the clip, such as the pusher bar 160, the bell crank gear 154 and the pivot arm 179, are adjusted accordingly. In this manner, each clip applier, of varying size, will be assembled in substantially the same manner and the inner mechanism thereof will operate in substantially the same manner.

For example, clip applier 100 may be provided in a relatively small and large scale, wherein each of the sizes of clip appliers stores and fires a relatively small, medium or large surgical clip. Based on the relative dimensions of the surgical clips, the corresponding clip appliers, and their corresponding components, must be scaled appropriately. However, in accordance with the present disclosure, each of the various sized clip appliers comprise the same component and may be assembled in the same sequence as one another. In this manner, a technician assembling the clip appliers will only have to learn the sequence and/or steps required for the assembly of one of the sizes of clip appliers and, in turn, be able to assemble the other sizes of clip appliers equally, without having to learn a new sequence or step of assembly.

Accordingly, the assembly method and/or steps for a relatively small, medium or large clip applier are substantially identical to one another.

At least the following components or parts vary in shape based on the relative size or scale of the clip applier, namely, the length of the arms of pivot arm 179, the length of the slot in which accelerator rack 156 translates; and the degree of rotation of bell crank gear 154.

Many other remaining components or parts are identical or have minor variations in feature size or scale. However, if desired, the shapes of the following parts may be modified in order to achieve the same result, namely, the length of slot 154f of bell crank gear 154, and/or the length of slot 156b formed in base wall 156a of accelerator rack 156.

It is contemplated that for a relatively small scaled clip applier, that a given rotation of approximately 45°, for a relatively small scaled bell crank gear 154, will result in approximately a 0.345 inch axial displacement of a relatively small scaled pusher bar 160 in order to load a relatively small sized clip into jaws 120. Similarly, it is contemplated that for a relatively medium scaled clip applier, that a given rotation of approximately 70°, for a relatively medium scaled bell crank gear 154, will result in approximately a 0.485 inch axial displacement of a relatively medium scaled pusher bar 160 in order to load a relatively medium sized clip into jaws 120. Likewise, it is contemplated that for a relatively large scaled clip applier, that a given rotation of approximately 90°, for a relatively large scaled bell crank gear 154, will result in approximately a 0.710 inch axial displacement of a relatively large scaled pusher bar 160 in order to load a relatively large sized clip into jaws 120.

In an alternate embodiment, as seen in FIGS. 54-57, it is contemplated that a proximal end of drive channel 140 may include or define a ratchet rack 140d integral therewith that is configured and adapted for engagement with ratchet pawl 142. Use and operation of ratchet mechanism 244 is substantially identical to ratchet mechanism 144 and thus will not be discussed in great detail herein.

In a further embodiment, as seen in FIG. 4 above, clip applier 100 may be provided with a strap 196 configured to secure energy source 198 to housing 104.

In an embodiment, it is also contemplated that as drive channel 140 is moved distally, and as resilient aim 148a of audible/tactile indicator 148 snaps over the distal edge of ledge 149, resilient arm 148a may strike or contact a surface formed in housing 104 thereby amplifying the further or second audible sound and/or tactile vibration.

Turning now to FIGS. 58-69, a surgical clip applier, in accordance with an alternate embodiment of the present disclosure, is generally designated as 300. Surgical clip applier 300 is substantially identical to surgical clip applier 100 and thus will only be discussed in detail herein to the extent necessary to identify differences in construction and operation thereof.

As seen in FIGS. 58, 60 and 64-66, clip applier 300 includes motion multiplier system having a bell crank gear 154, and an accelerator rack 356 slidably supported in housing 104. Accelerator rack 356 includes a base wall 356a defining an elongate, longitudinally extending slot 356b formed therein, for slidable receipt of pivot pin 154a of bell crank gear 154. Accelerator rack 356 includes a side wall 356c projecting in opposite directions from a side edge of base wall 356a, and a gear rack 356d formed in side wall 356c and in registration or alignment with slot 356b of base wall 356a. Gear rack 356d is configured for engagement with gear teeth 154g of spur gear 154d of bell crank gear 154. Accelerator rack 356 further includes a camming member 356e projecting from a distal edge of base wall 356a, and a nub 356f projecting from distal edge of side wall 356c.

The length of slot 356b of base wall 356a of accelerator rack 356 will vary depending on the size of clip applier 300. For relatively smaller clip appliers (e.g., clip appliers which apply relatively smaller clips), the length of slot 356b of accelerator rack 356 will be relatively shorter, and for relatively larger clip appliers (e.g., clip appliers which apply relatively larger clips), the length of slot 356b of accelerator rack 356 will be relatively longer.

In use, as will be discussed in great detail below, as accelerator rack 356 is moved or translated axially, gear rack 356d of accelerator rack 356 engages with gear teeth 154g of spur gear 154d of bell crank gear 154 to cause bell crank gear 154 to rotate or pivot about pivot pin 154a.

As seen in FIGS. 58, 61 and 67-69, clip applier 300 includes a motion reversing mechanism having a wedge plate pivot arm 379 pivotally supported in lower housing half 104b of housing 104 for transmitting translation of wedge plate 180 to translation of drive channel 140. Pivot arm 379 includes a pivot boss 379a configured for pivotable connection to housing 104, a first stem or finger 379b provided at one end of pivot arm 379 and extending in a direction opposite to pivot boss 379a, and second stem or finger 379c provided at a second end of pivot arm 379 and extending in a same direction as pivot boss 379a. First stem or finger 379b is configured and adapted for engagement in proximal-most slot 180d of wedge plate 180. Second stem or finger 379c is configured for engagement in a slot 358b formed in arm link 358 (FIG. 62) which is connected in a window 140h defined in a drive channel 140.

In use, as will be discussed in greater detail below, as drive channel 140 is moved distally, after a dwell period, arm link 358 urges second stem or finger 379c of pivot arm 379 to move in a first or distal direction thereby moving first stem or finger 379b in a second or proximal direction and causing wedge plate 180 to move in the second direction, and vice-versa. As wedge plate 180 is moved in a distal direction, as will be discussed hereinbelow, wedge plate 180 cams against an inner surface of jaws 120 to thereby maintain jaws 120 spaced apart from one another.

Clip applier 300 further includes a biasing member 384, in the form of a tension spring, operatively secured to and between a proximal end of wedge plate 180 and housing 104, tending to maintain wedge plate 180 in an advanced or distal-most position. Biasing member 384 functions to advance or facilitate advancement of wedge plate 180 following formation of a clip "C" positioned between jaws 120.

As seen in FIGS. 58, 59 and 64-66, clip applier 300 further includes an audible/tactile indicator 348 supported on drive channel 140. Indicator 348 includes a first resilient finger 348a and second resilient finger 348b. In use, as will be described in greater detail below, as clip applier 300 is actuated and drive channel 140 is reciprocated, first resilient finger 348a of indicator 348 interacts with corresponding complementary structure provided in clip applier 300 to create an audible and/or a tactile feedback to the user and second resilient finger 348b of indicator 348 interacts with caroming member 356e of accelerator rack 356 to adjust the stroke of clip applier 300 for varying sizes of clip applier 300.

As seen in FIGS. 58, 62 and 67-69, clip applier 300 further includes an arm link 358 slidably disposed in housing 104 and operatively connected to drive channel 140 for translation therewith. Arm link 358 includes a body portion 358a defining a slot 358b therein, a guide wall 358c projecting from an upper surface of body portion 358a, and a stem 358d extending in an upward direction from a proximal edge of body portion 358a. Slot 358b of arm link 358 is configured to slidably receive second stem or finger 379c of pivot arm 379. Guide wall 358c of arm link 358 is dimensioned to ride against a surface of drive channel 140. Stem 358d of arm link 358 is dimensioned for slidable receipt in window 140h formed in drive channel 140. Window 140h of drive channel 140 is dimensioned to define a period of dwell between when drive channel 140 is moved distally and when arm link 358 actuates pivot aim 379.

Figure 64:
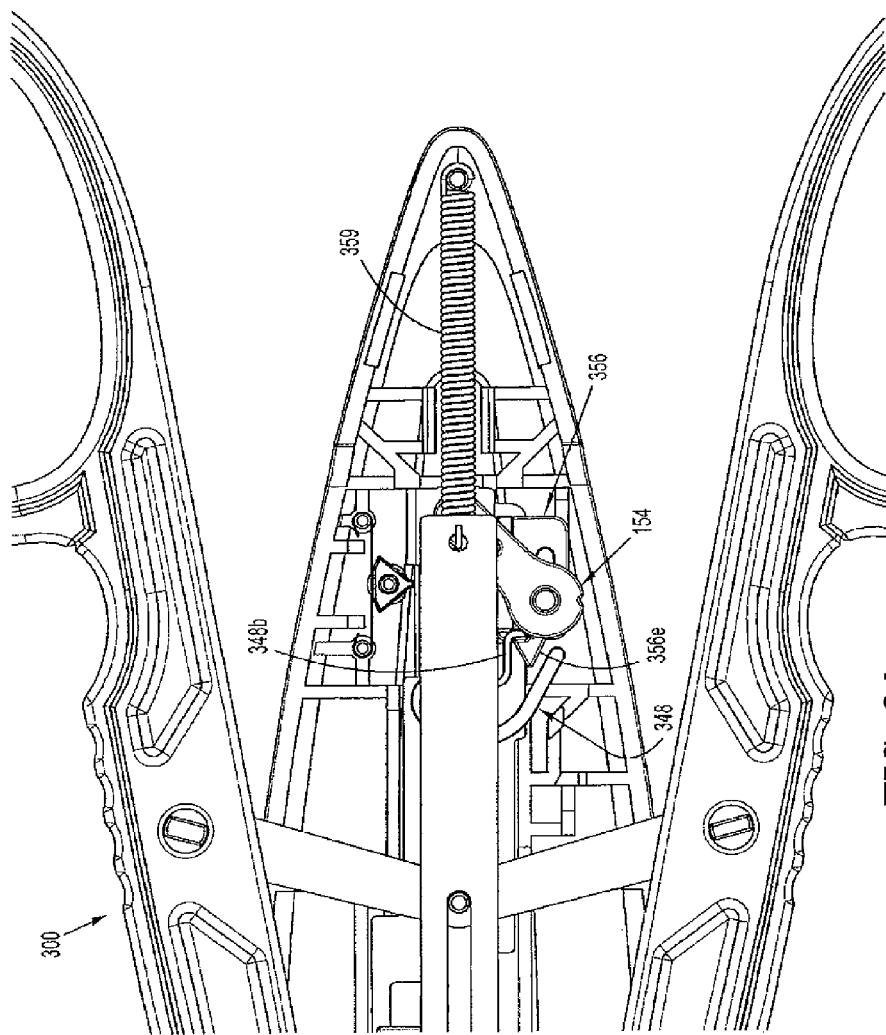
FIGS. 64-66 are perspective views of the sequential operation of the audible/tactile indicator and accelerator rack of the surgical clip applier of FIG. 58, during a complete squeezing of the handles thereof.
Figure 65:
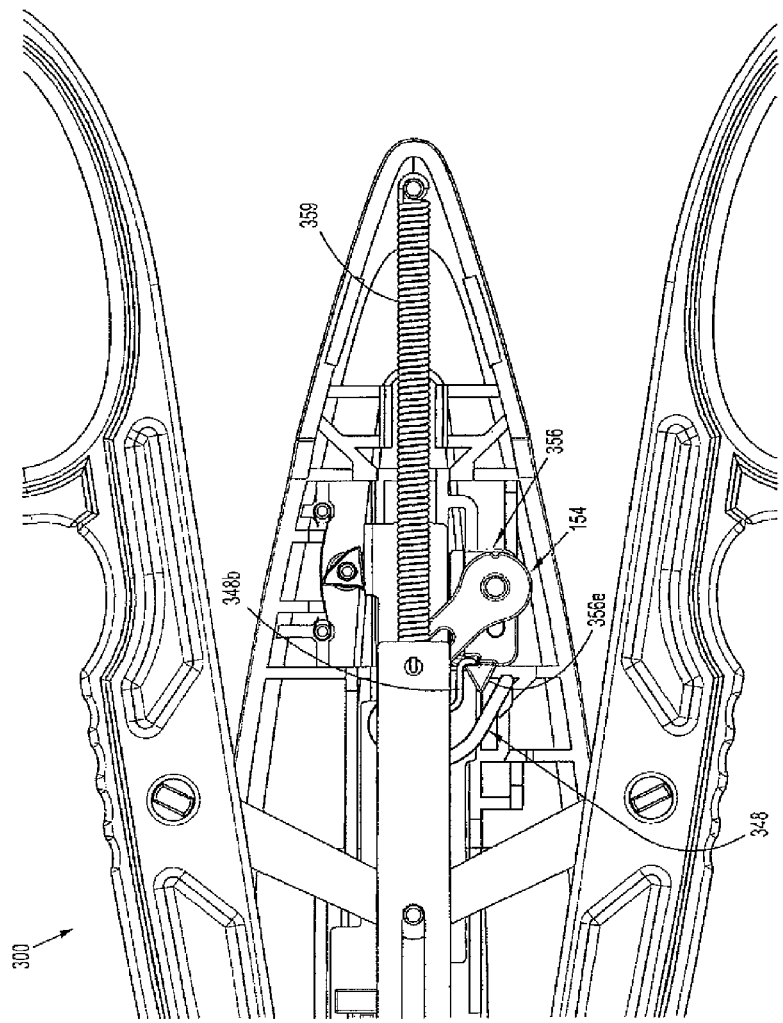
Figure 66:
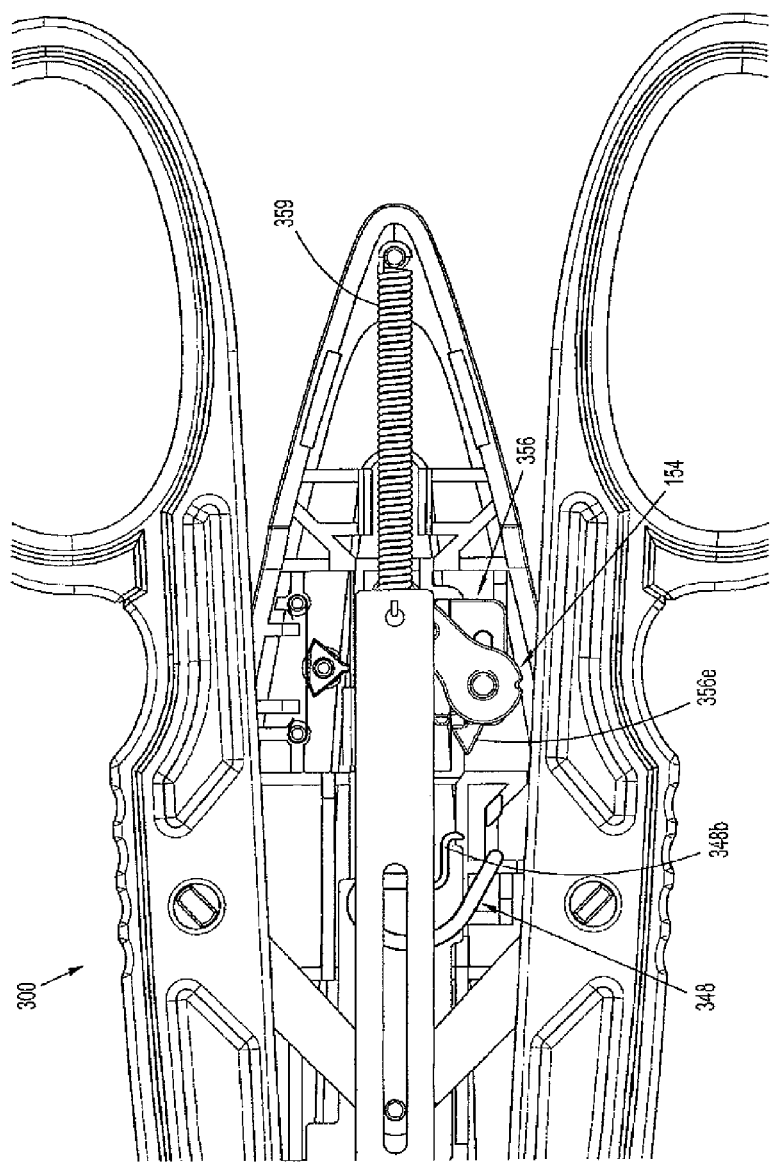
Figure 67:
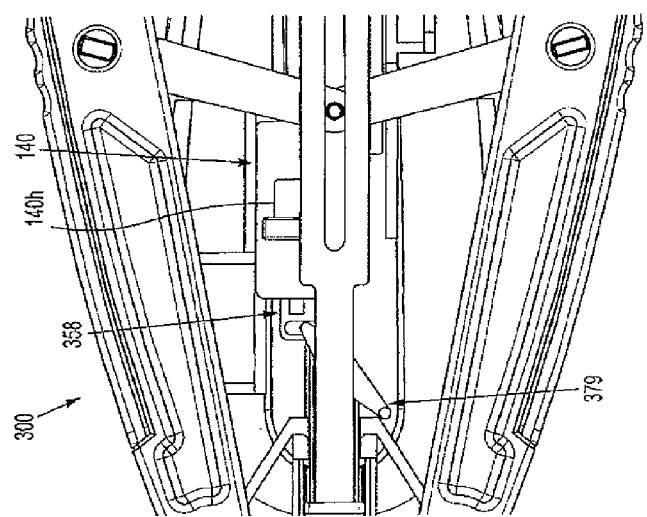

With reference to FIGS. 64-69, the differences in the operation of surgical clip applier 300, as compared to surgical clip applier 100, are described. Prior to any initial squeezing of handles 106 of clip applier 300, as seen in FIGS. 64 and 67, drive pin 124 is located at a proximal-most position, pawl 142 is located distal of rack 140d of drive channel 140, arm link 358 is located at a proximal-most position relative to housing 104 and a distal-most position in window 140h of drive channel 140, and no clips "C" are positioned within jaws 106. Since drive pin 124 is at a proximal-most position, pusher bar 160, stabilizer 162, and drive channel 140 are also at a proximal-most position. With pusher bar 160 located at a proximal-most position, accelerator rack 356 is located at a proximal-most position, and second resilient finger 348b of indicator 348 is disposed proximal of camming member 356e of accelerator rack 356. Also, prior to an initial squeezing of handles 106 of clip applier 300, wedge plate 180 is located at a distal-most position such that distal end 180a of wedge plate 180 is interposed between jaws 120.

Figure 68:
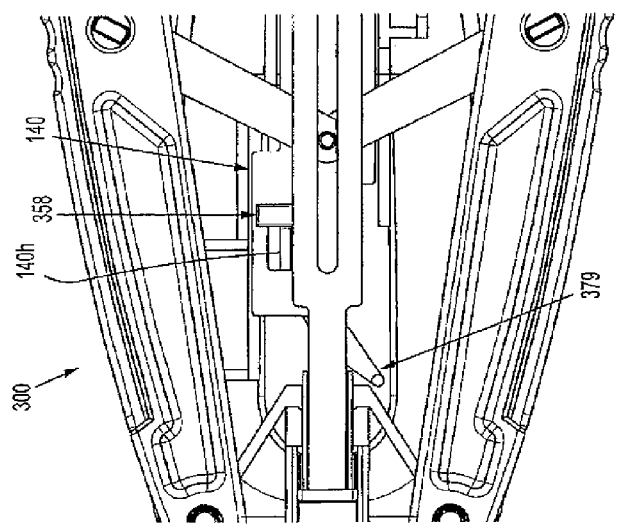
FIGS. 67-69 are perspective views of the sequential operation of the pivot arm and the arm link of the surgical clip applier of FIG. 58, during a complete squeezing of the handles thereof.

As drive channel 140 is moved distally, as seen in FIGS. 65 and 68, indicator 348 is moved distally therewith. As indicator 348 is moved distally, second resilient finger 348b thereof drags accelerator rack 356 in a distal direction. As accelerator rack 356 is dragged in a distal direction, accelerator rack 356 causes bell crank gear 154 to rotate about pivot pin 154a and transmit distal axial movement to nub 162c of stabilizer 162 which, in turn, transmits distal axial movement to pusher bar 160. As drive channel 140 is moved distally biasing member 146 is stretched or extended.

Figure 69:
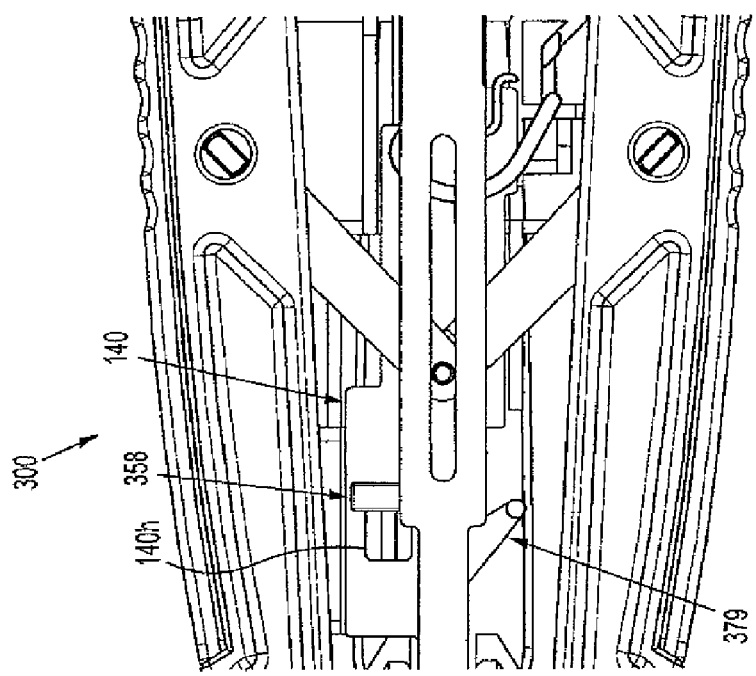

During the initial squeeze of handles 106, as seen in FIGS. 67 and 68, drive channel 140 is moved distally until stem 358d of arm link 358 is engaged by an end wall of window 140h of drive channel 140 (i.e., the dwell). Once the end wall of window 140h is in abutment with stem 358d of arm link 358 (i.e., after the dwell has been exhausted), further distal movement of drive channel 140, as seen in FIG. 69, results in distal movement of arm link 358. As arm link 358 is moved distally, the transverse portion of slot 358b of arm link 358 will cause pivot arm 379 to rotate which, in turn, causes wedge plate 380 to move in a proximal direction, thereby withdrawing distal end 180a thereof from between jaws 120 and allowing for jaws 120 to eventually be closed or approximated. Once the required rotation of pivot arm 379 is achieved, pivot arm 379 stops rotating as finger 379c of pivot arm 379 rides through longitudinal portion of L-shaped slot 358b of arm link 358. Finger 379c of pivot arm 379 remains in longitudinal portion of L-shaped slot 358b of arm link 358 until the stroke of drive channel 140 is completed.

As seen in FIGS. 64 and 65, during the initial squeeze of handles 106, pusher bar 160 is moved distally with drive channel 140, as described above, until nub 356f of accelerator rack 356 abuts against a ledge formed in housing 104, at which time distal advancement of accelerator rack 356 is stopped. With accelerator rack 356 prevented from further distal advancement, as seen in FIG. 66, as drive channel 140 is further advanced distally, drive channel 140 pulls or flexes second resilient finger 348b of indicator 348 from behind camming member 356e of accelerator rack 356 allowing pusher bar 160 to move in a proximal direction to a home position. Pusher bar 160 is retracted to its home position by a return spring 359 having a first end that is secured to pusher bar 160 and a second end that is secured to the housing.

Following a complete stroke or squeezing of handles 106 and during an opening of handles 106, drive channel 140 is moved in a proximal direction. In operation, as drive channel 140 is moved proximally, a front end wall of window 140h of drive channel 140 acts on stem 358d of arm link 358 to drawn arm link 358 in a proximal direction. As arm link 358 is moved proximally, arm link 358 causes pivot arm 379 to rotate which, in turn, causes wedge plate 180 to move in a distal direction. As wedge plate 180 is moved in a distal direction, distal end 180a of wedge plate 180 is reinserted or reintroduced into jaws 120, thereby spreading jaws 120 apart.

As drive channel 140 is moved further in a proximal direction, second resilient finger 348b of indicator 348 engages against camming member 356e of accelerator rack 356 causing accelerator rack 356 to move in a proximal direction. Movement of accelerator rack 356 in a proximal direction results in rotation of bell crank gear 152 about pivot pin 152a to thereby move pusher bar 160 and stabilizer 162 in a proximal direction. As drive channel 140 is further moved in a proximal direction, second resilient finger 348b of indicator 348 cams, flexes or snaps behind camming member 356e for re-engagement with accelerator rack 356.

Turning now to FIGS. 70-88, a surgical clip applier, in accordance with an alternate embodiment of the present disclosure, is generally designated as 400. Surgical clip applier 400 is substantially identical to surgical clip applier 100 and thus will only be discussed in detail herein to the extent necessary to identify differences in construction and operation thereof.

As seen in FIGS. 70, 71 and 75-77, clip applier 400 includes motion multiplier system having a gear member 454 rotatably supported in housing 404 of handle assembly 402. Gear member 454 includes a body plate 454a defining an axis of rotation, a gear 454b supported on body plate 454a and concentric with the axis of rotation, and a gear segment 454c formed at an outer edge of body plate 454a.

As seen in FIGS. 70, 72 and 75-77, clip applier 400 further includes a drive channel gear rack 442 supported on or otherwise connected to drive channel 440. Drive channel gear rack 442 defines a plurality of gear teeth 442a formed in a side edge thereof. Drive channel gear rack 442 is configured and dimensioned such that gear teeth 442a thereof are engageable with gear 454b of gear member 454. In use, as drive channel 440 is translated, drive channel gear rack 442 is translated therewith or vice-versa.

As seen in FIGS. 70, 73 and 75-77, the motion multiplier system of clip applier 400 also includes a pusher bar gear rack 462 supported on or otherwise connected to pusher bar 460. Pusher bar gear rack 462 defines a plurality of teeth 462a formed in a side edge thereof, and a stem 462b extending proximally therefrom. Pusher bar rack 462 is configured and dimensioned such that gear teeth 462a thereof are engageable with gear segment 454c of gear member 454. In use, as pusher bar 460 is translated, pusher bar gear rack 462 is translated therewith or vice-versa.

Figure 70:
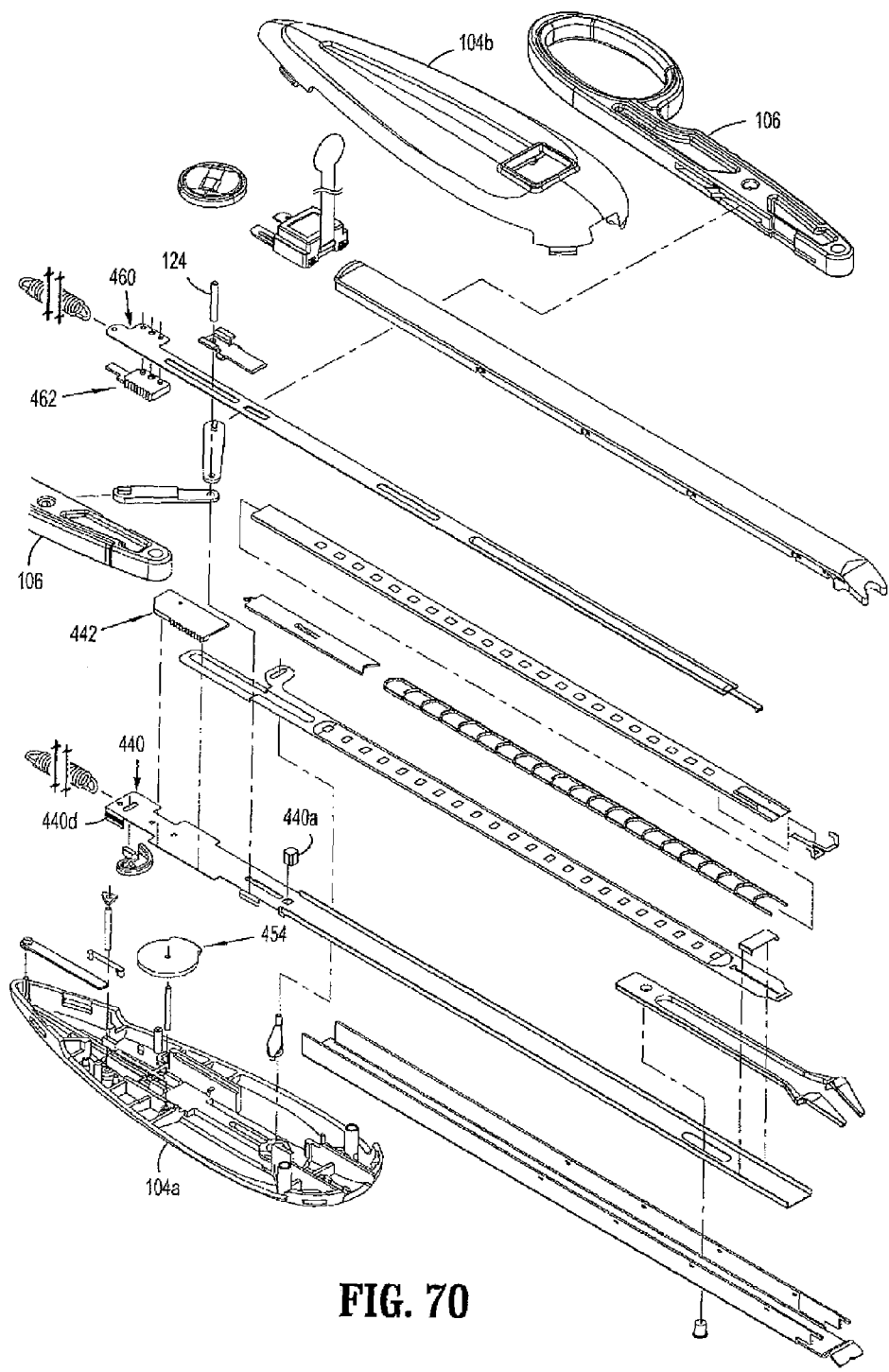
FIG. 70 is an exploded perspective view of a surgical clip applier according to another embodiment of the present disclosure.
Figure 71:
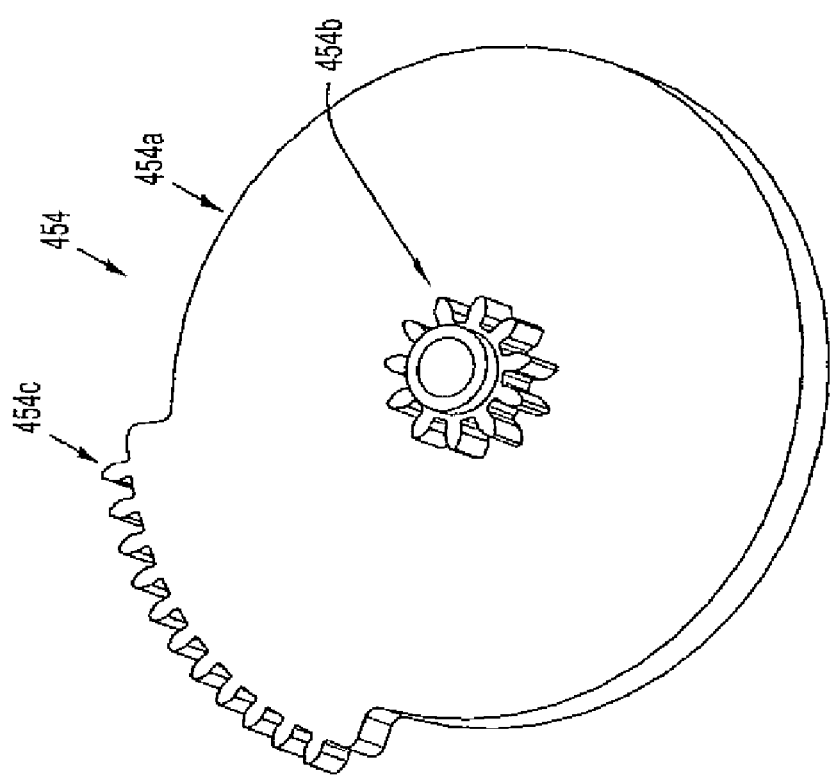
FIG. 71 is an enlarged perspective view of a gear member of the surgical clip applier of FIG. 70.
Figure 72:
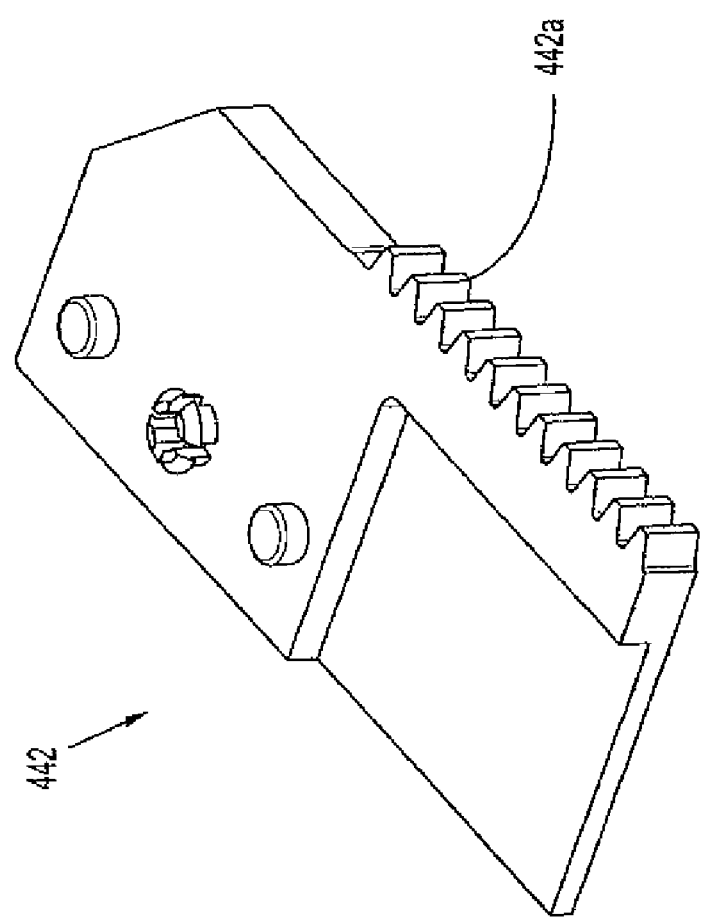
FIG. 72 is an enlarged perspective view of a drive channel gear rack of the surgical clip applier of FIG. 70.
Figure 73:
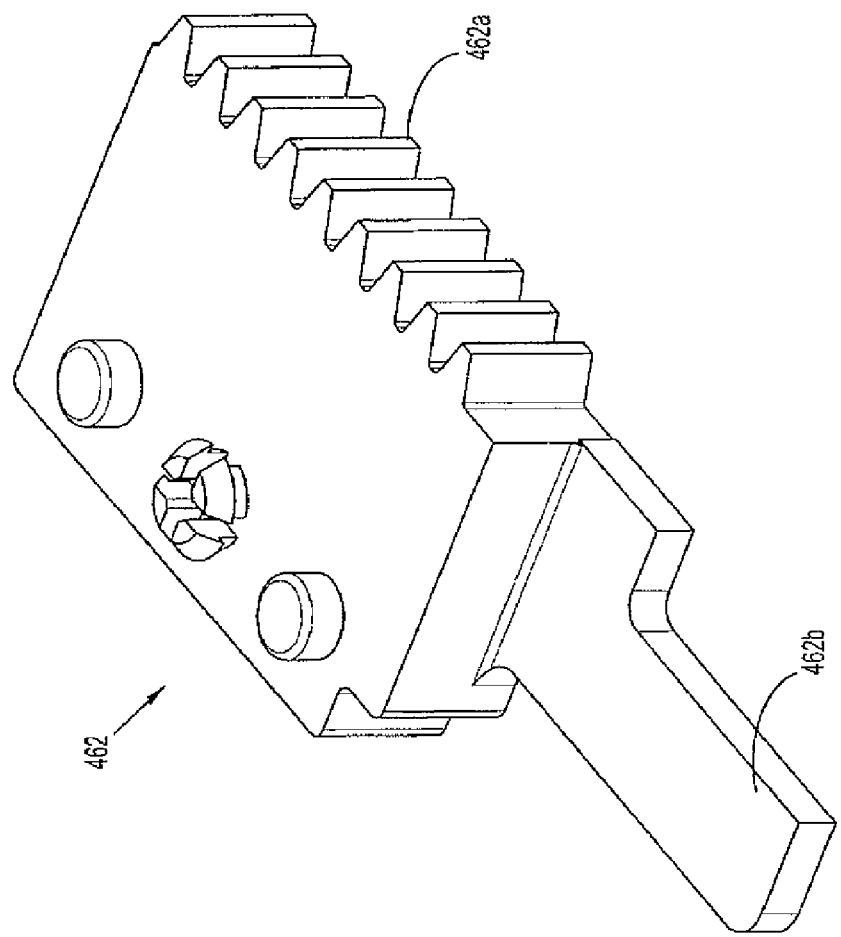
FIG. 73 is an enlarged perspective view of a pusher gear rack of the surgical clip applier of FIG. 70.
Figure 74:
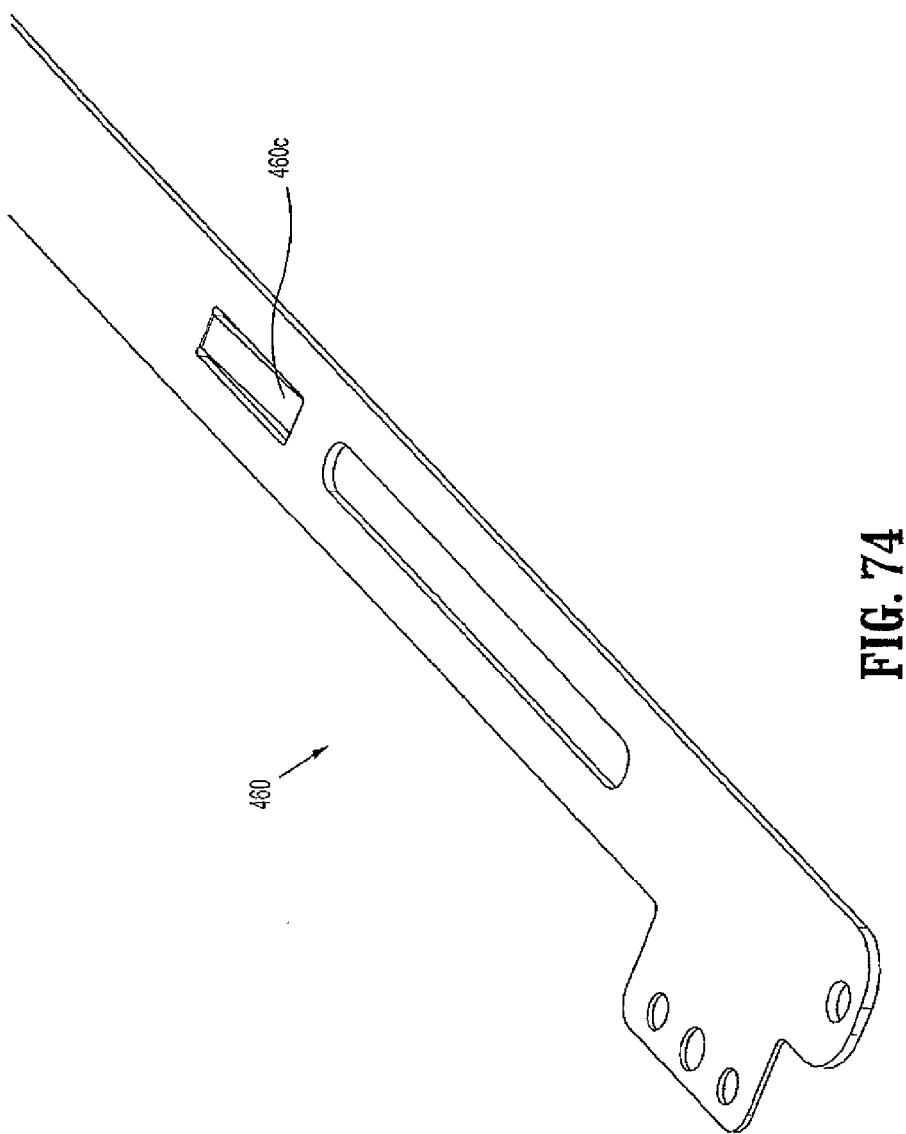
FIG. 74 is an enlarged perspective view of a proximal end of a pusher bar of the surgical clip applier of FIG. 70.
Figure 75:
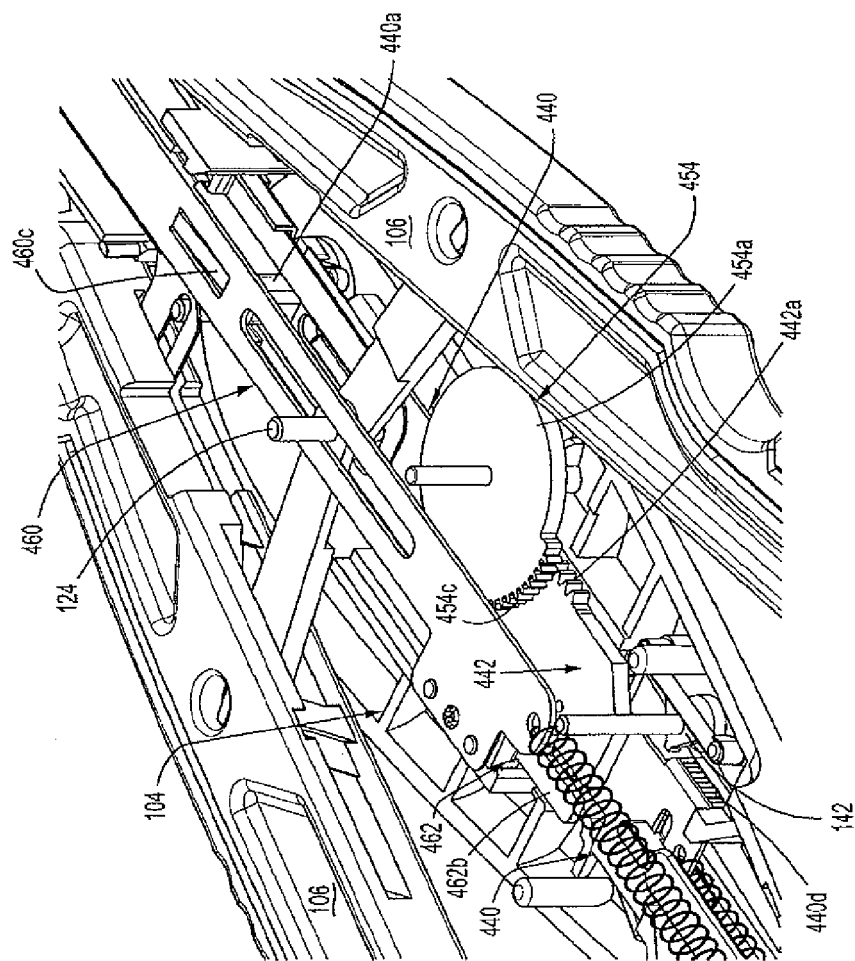
FIG. 75 is a perspective view of a handle assembly of the surgical clip applier of FIG. 70, illustrated with a housing half-section removed therefrom and shown in an initial un-squeezed condition.

As seen in FIGS. 70, 74 and 75, clip applier 400 includes a pusher bar 460 having a resilient finger 460c projecting from a surface thereof. When handle assembly 404 is in an un-squeezed condition, as seen in FIG. 75, resilient finger 460c of pusher bar 460 is disposed distally of a drive block 440a (FIGS. 75-77) extending from drive channel 440. Also, in the initial un-squeezed condition, no clips "C" are positioned within jaws 106.

Figure 76:
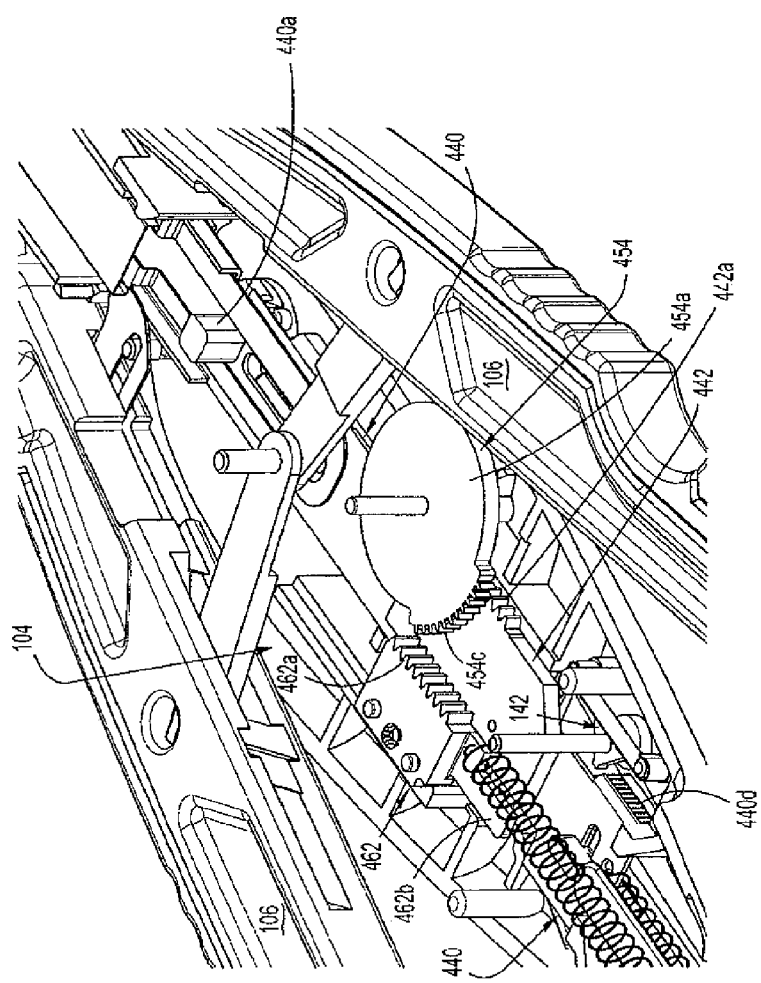
FIG. 76 is a perspective view of the handle assembly of FIG. 75 shown with the pusher bar also removed therefrom.
Figure 77:
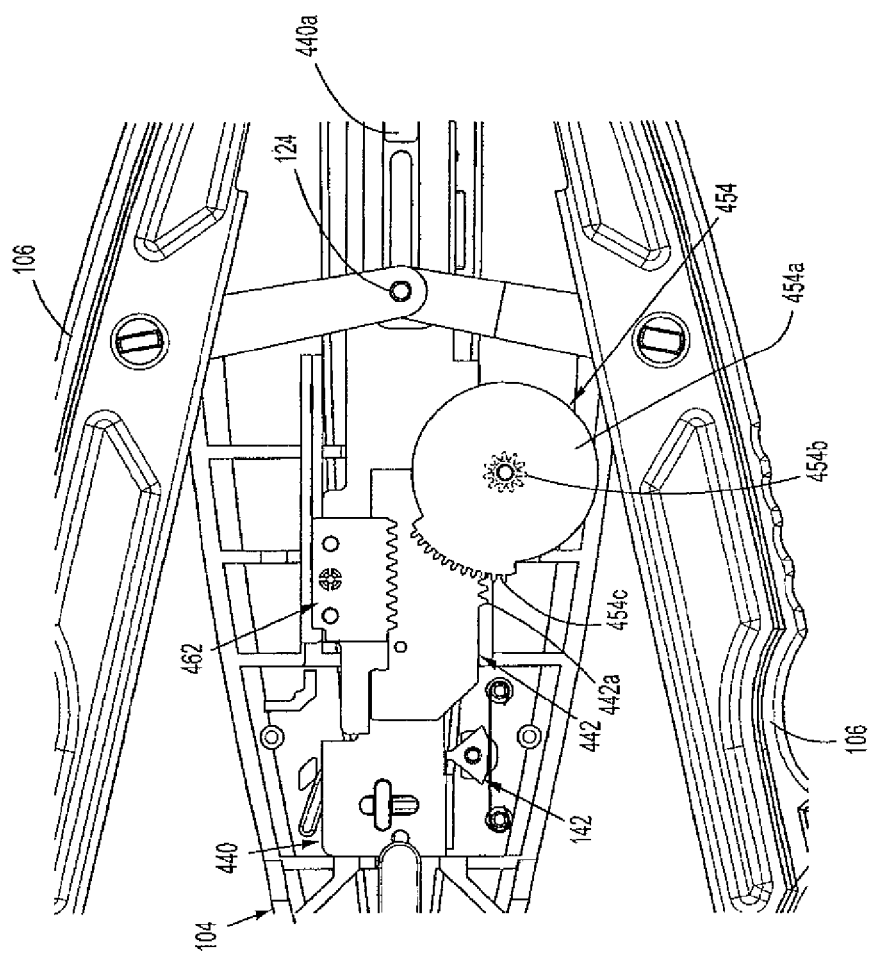
FIG. 77 is a plan view of the handle assembly of FIG. 76.

With reference to FIGS. 75-86, the differences in the operation of surgical clip applier 400, as compared to surgical clip applier 100, are described. Prior to any initial squeezing of handles 106 of clip applier 400, as seen in FIGS. 75-77, drive pin 124 is located at a proximal-most position, pawl 142 is located distal of rack 140d of drive channel 440, each of drive channel gear rack 442 and pusher gear rack 462 are located at a proximal-most position relative to housing 104 and gear member 454 is un-rotated. Since drive pin 124 is at a proximal-most position, drive bar 440 and pusher bar 460 are each also located at a proximal-most position. Also, prior to an initial squeezing of handles 106 of clip applier 400, drive block 440a of drive channel 440 is disposed proximally of resilient finger 460c pusher bar 460.

Figure 78:
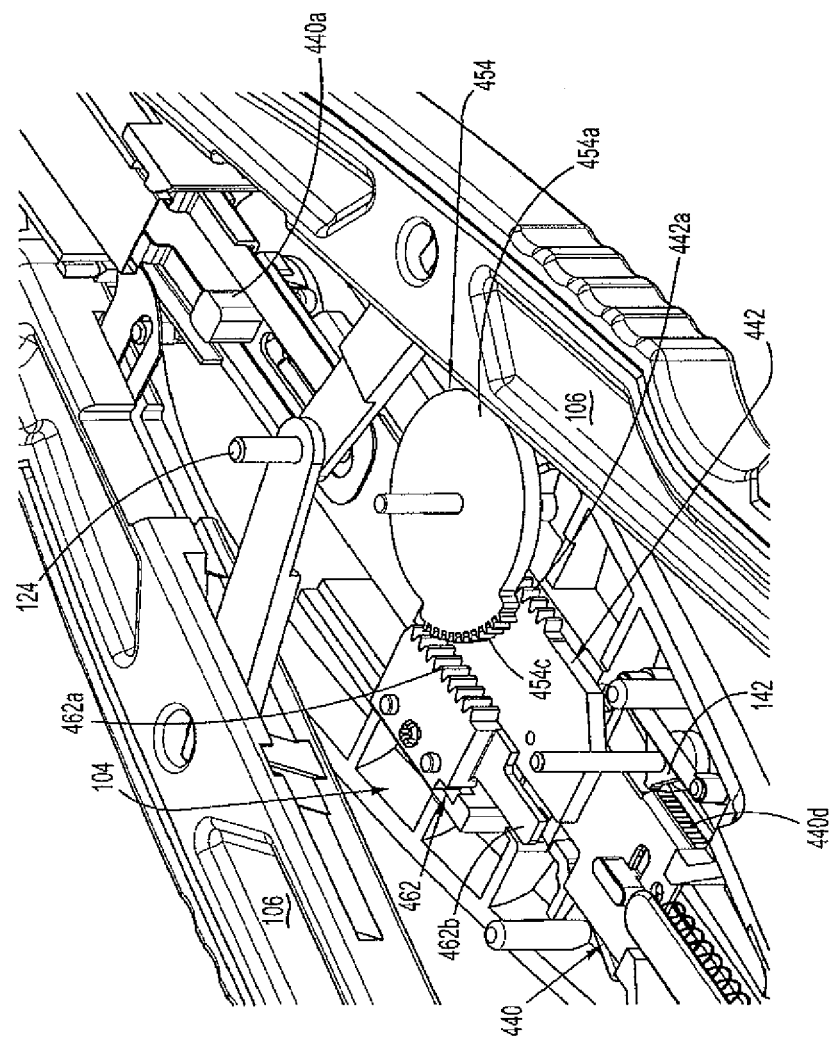
FIG. 78 is a perspective view of the handle assembly as illustrated in FIG. 75, shown during an initial squeezing of the triggers.
Figure 79:
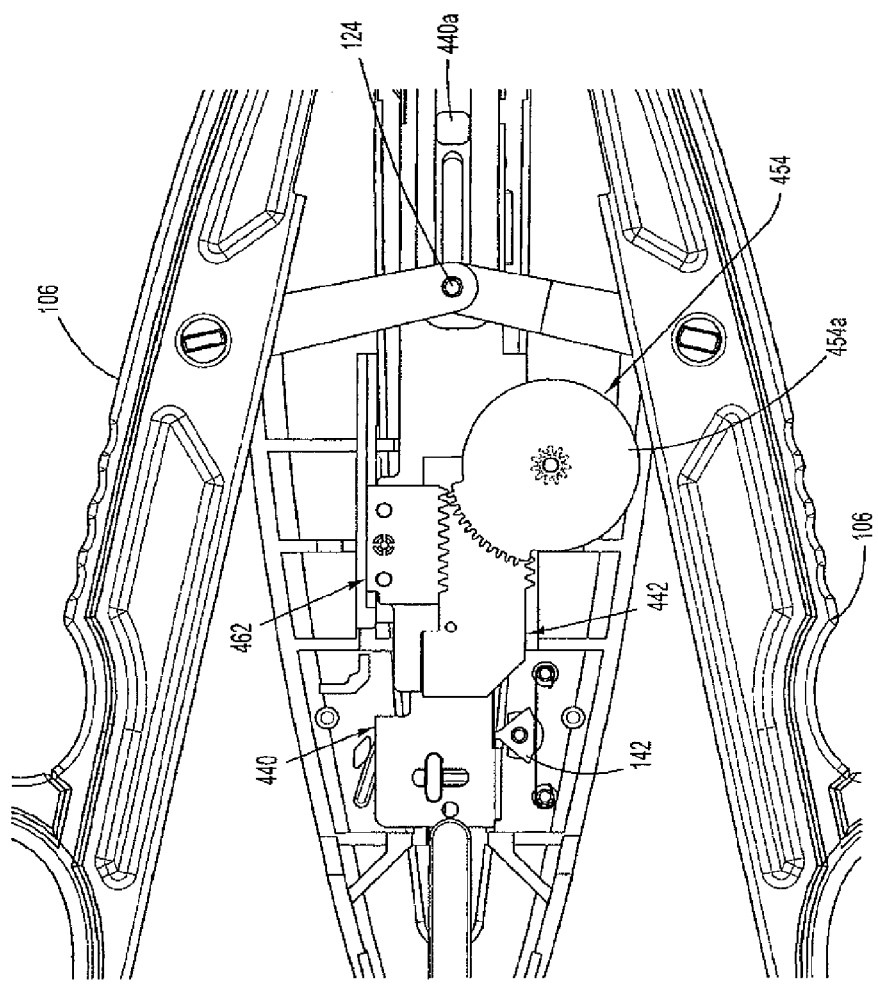
FIG. 79 is a plan view of the handle assembly of FIG. 78.

As drive channel 440 is moved distally, as seen in FIGS. 78 and 79, drive channel 440 is moved distally. As such, drive block 440a of drive channel 440 engages resilient finger 460c of pusher bar 460 thereby causing pusher bar 460 to be advanced distally as well. As drive channel 440 and pusher bar 460 are moved distally, pusher bar 460 moves pusher gear rack 462 until teeth 462a of pusher gear rack 462 engages gear segment 454c of gear member 454.

Figure 80:
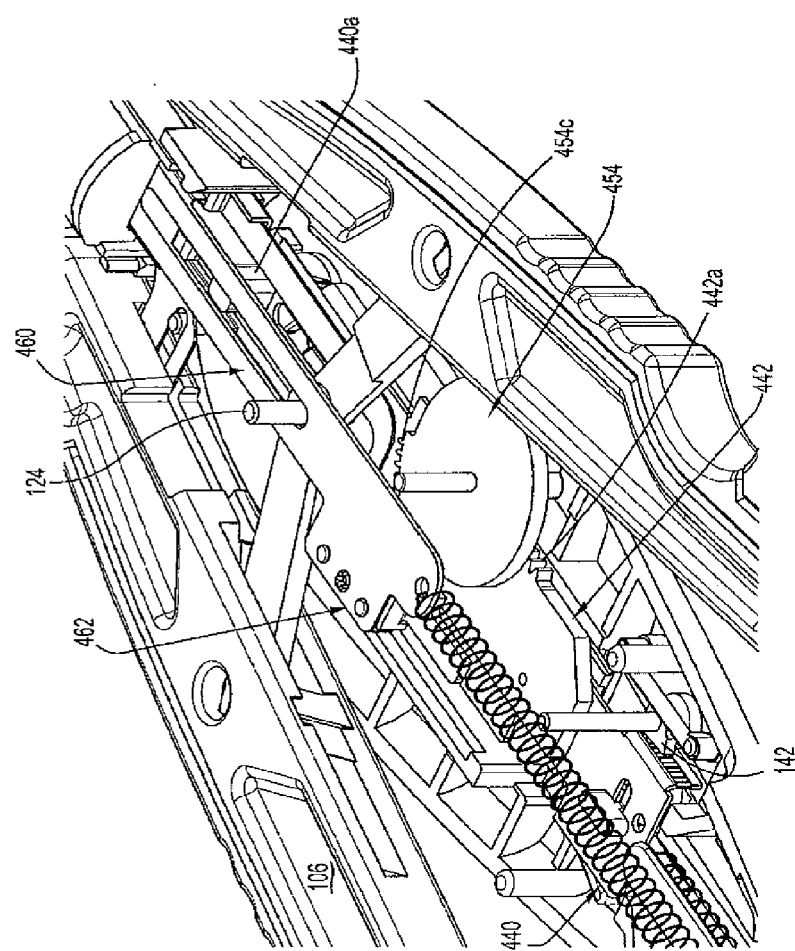
FIG. 80 is a perspective view of the handle assembly of the surgical clip applier of FIG. 70, illustrated with a housing half-section removed therefrom and shown during a further squeezing of the triggers.
Figure 81:
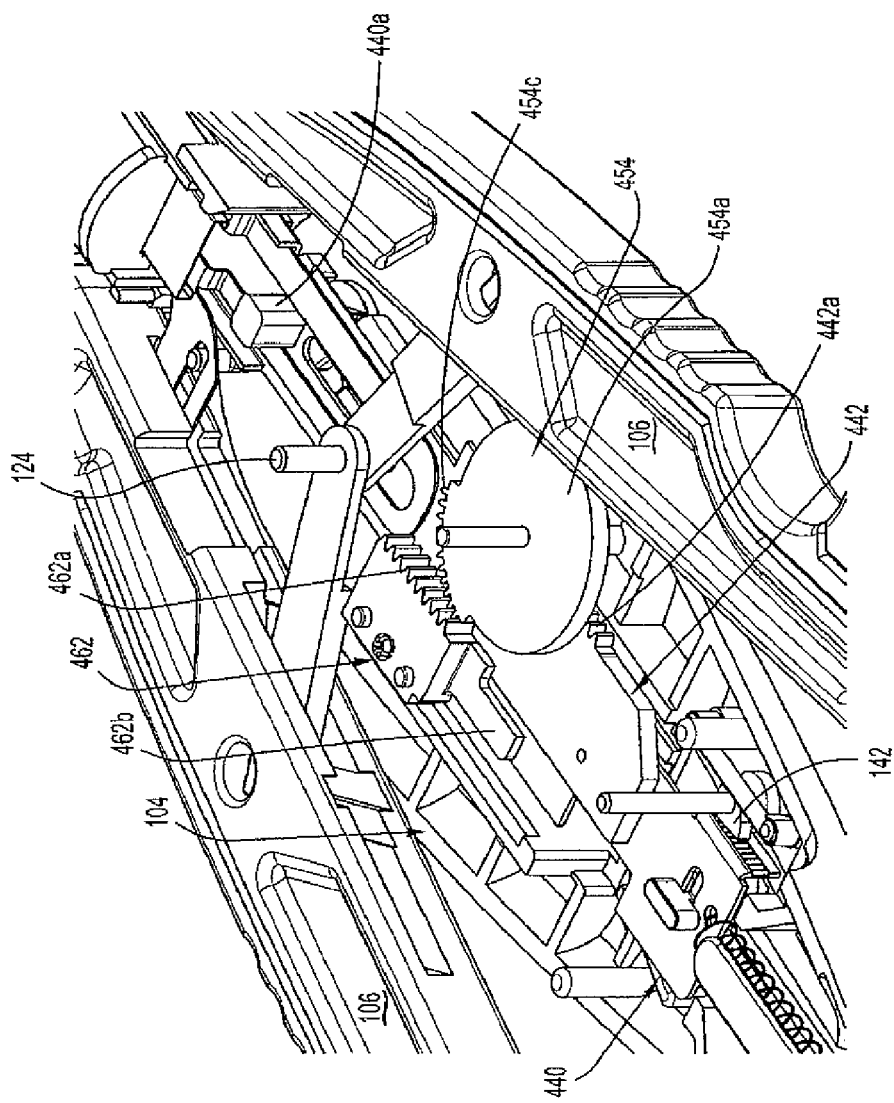
FIG. 81 is a perspective view of the handle assembly of FIG. 80 shown with the pusher bar also removed therefrom.
Figure 82:
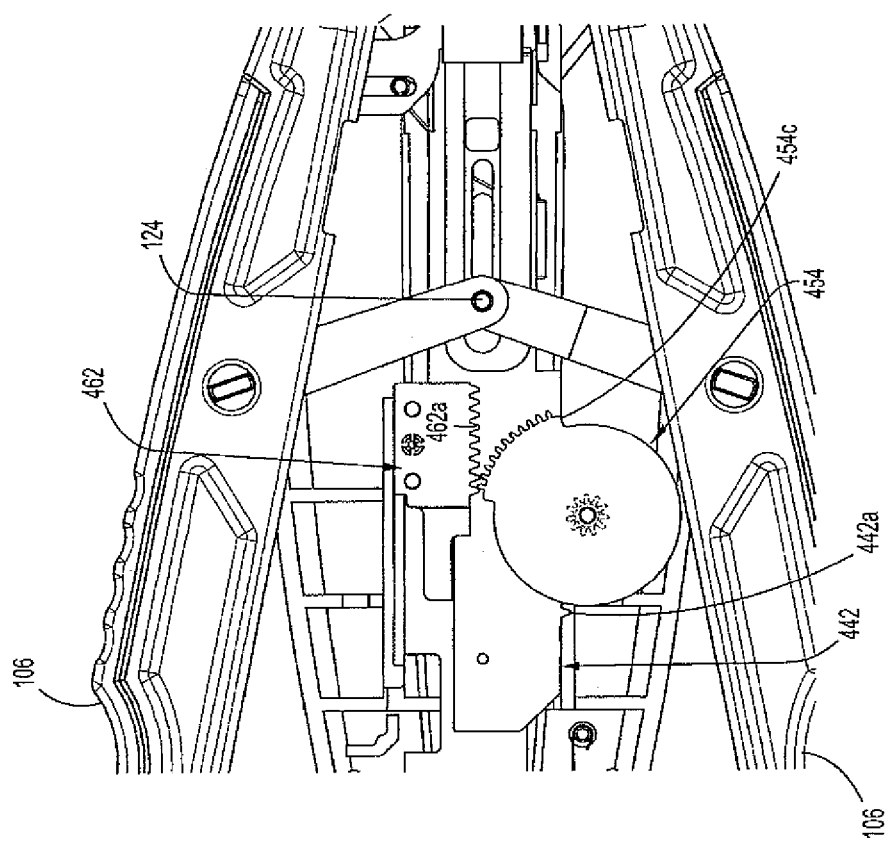
FIG. 82 is a plan view of the handle assembly of FIG. 81.

Turning now to FIGS. 80-82, as handle 106 are further actuated, thus moving drive channel 440 further distally, pusher bar 460 is moved distally an amount sufficient for pusher gear rack 462 to be moved distal and free of gear segment 454c of gear member 454. Also, at this point in time teeth 442a of drive channel gear rack 442 engage with gear 454b of gear member 454, thus preventing gear member 454 from returning to a home position.

At this stage, a clip (not shown) has been fully delivered into the jaws by pusher bar 460. Additionally, at this stage pawl 142 has been engaged by rack 140d of drive channel 440. As such, drive channel 440 may not return to a home position until drive channel 440 has completed its distal stroke.

Figure 83:
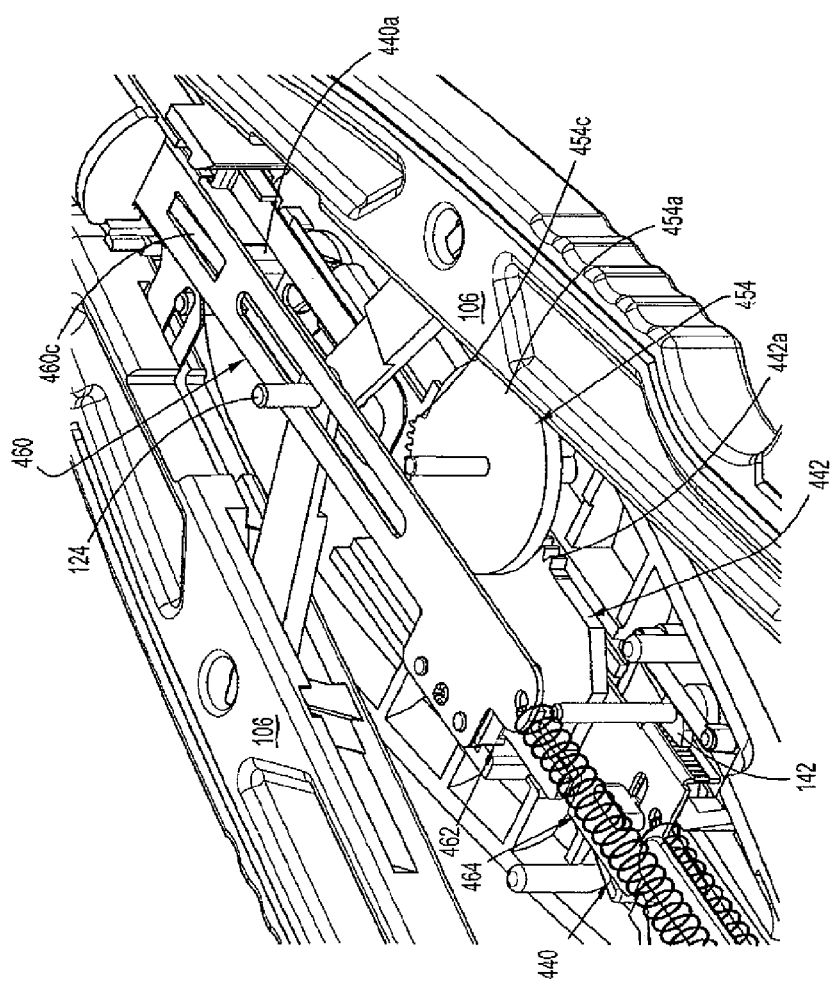
FIG. 83 is a perspective view of the handle assembly of the surgical clip applier of FIG. 70, illustrated with the housing half-section removed therefrom and shown during still a further squeezing of the triggers.
Figure 84:
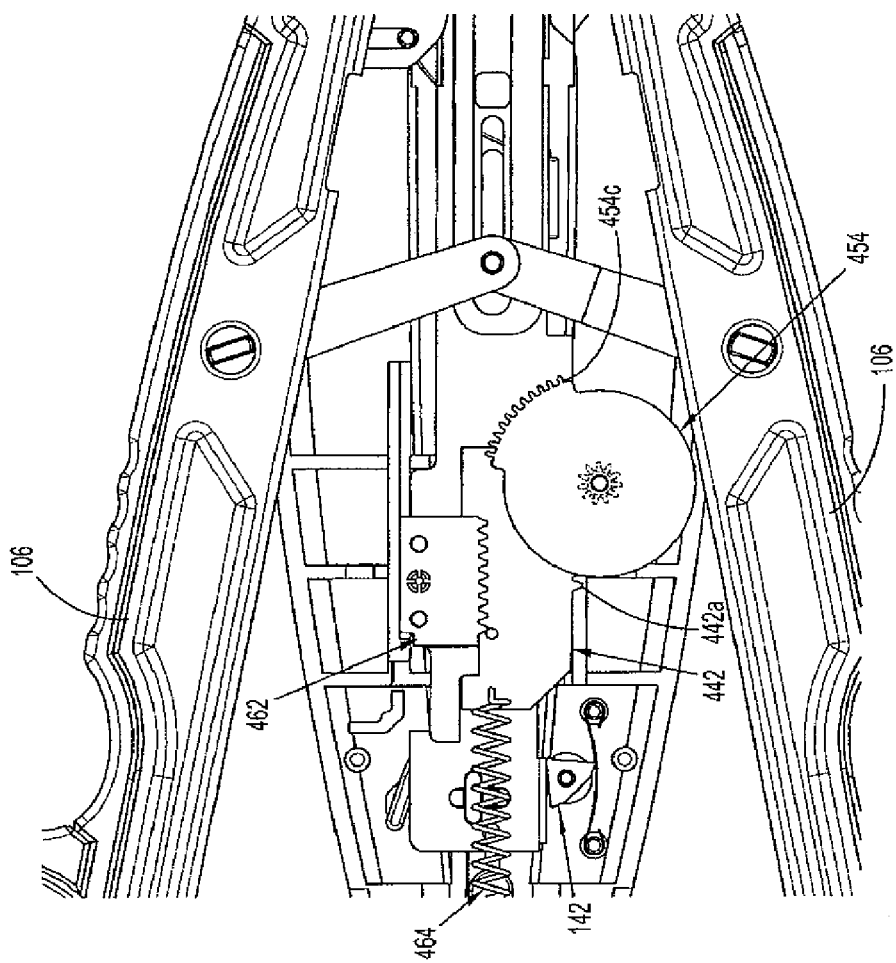
FIG. 84 is a plan view of the handle assembly of FIG. 83.

As seen in FIGS. 83 and 84, as drive channel 440 is further moved distally, drive block 440a of drive channel 440 snaps beyond resilient finger 460c of pusher bar 460 thereby allowing extension spring 464 to withdraw pusher bar 460 to a home position.

Figure 85:
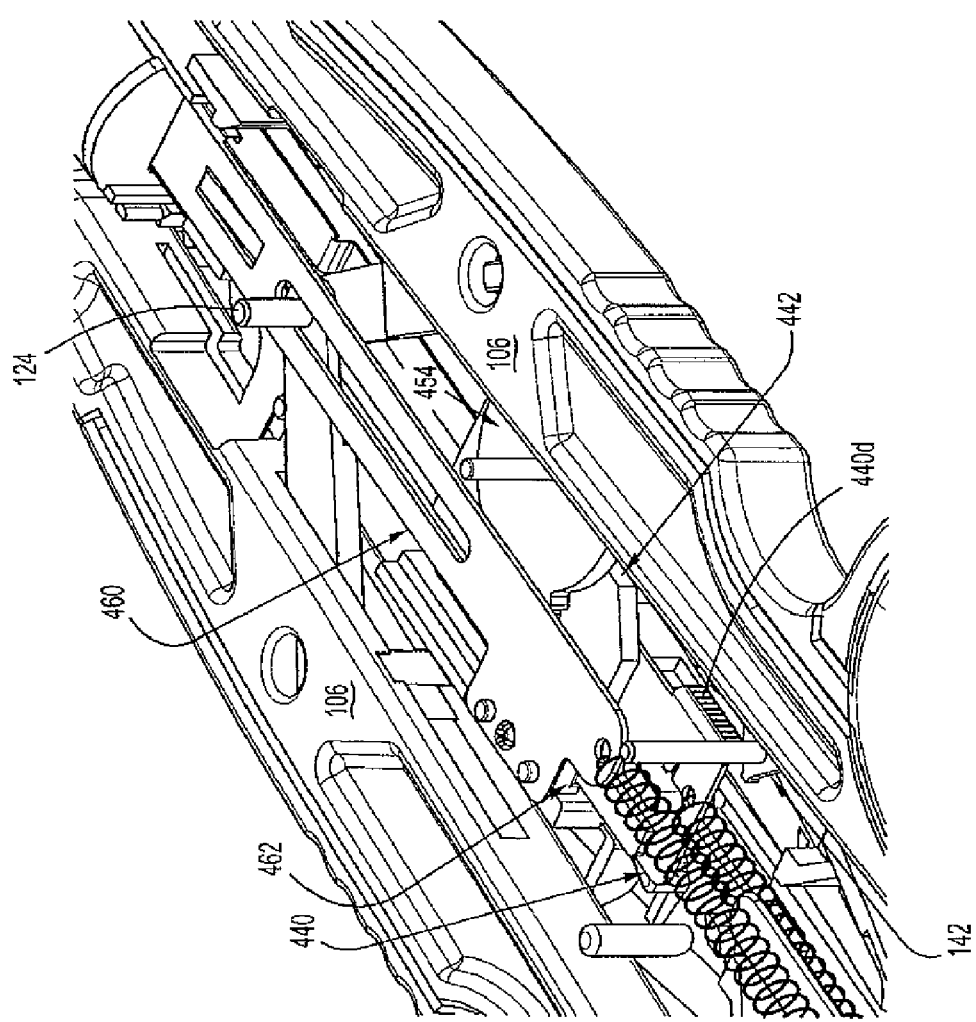
FIG. 85 is a perspective view of the handle assembly of the surgical clip applier of FIG. 70, illustrated with the housing half-section removed therefrom and shown during still a final squeezing of the triggers.
Figure 86:
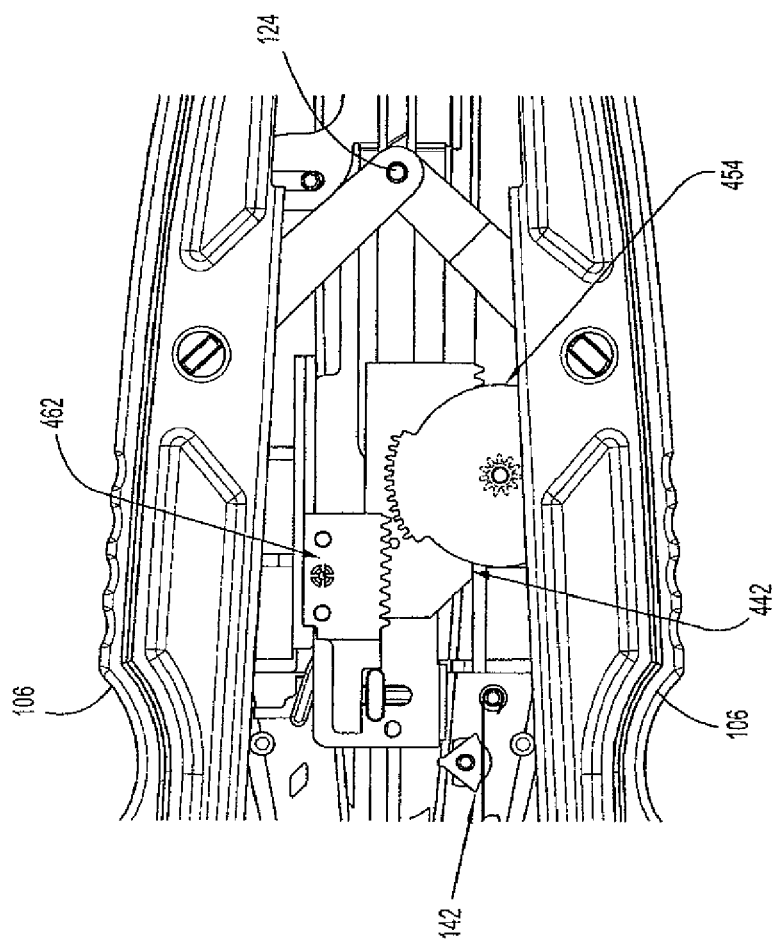
FIG. 86 is a plan view of the handle assembly of FIG. 85.

As seen in FIGS. 85 and 86, while pusher bar 460 remains static in the home position, drive channel 440 may continue to move distally to fully actuate clip applier 400 and form the surgical clip disposed within the jaws. At this stage, rack 140d of drive channel 440 has moved distally beyond pawl 142 thus allowing for drive channel 440 to return to the home position.

Assembly of each of the various sized clip appliers 100-400 is accomplished in substantially the same sequence of steps irrespective of the relative size of the clip applier. In this manner, as stated above, a technician assembling the clip appliers will only have to learn the sequence and/or steps required for the assembly of one of the sizes of clip appliers and, in turn, be able to assemble the other sizes of clip appliers equally, without having to learn a new sequence or step of assembly.

Figure 87:
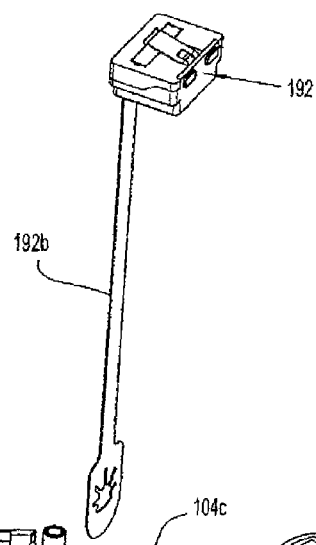
FIGS. 87-110 illustrate a method of assembling the surgical clip applier of FIGS. 1-57.
Figure 88:
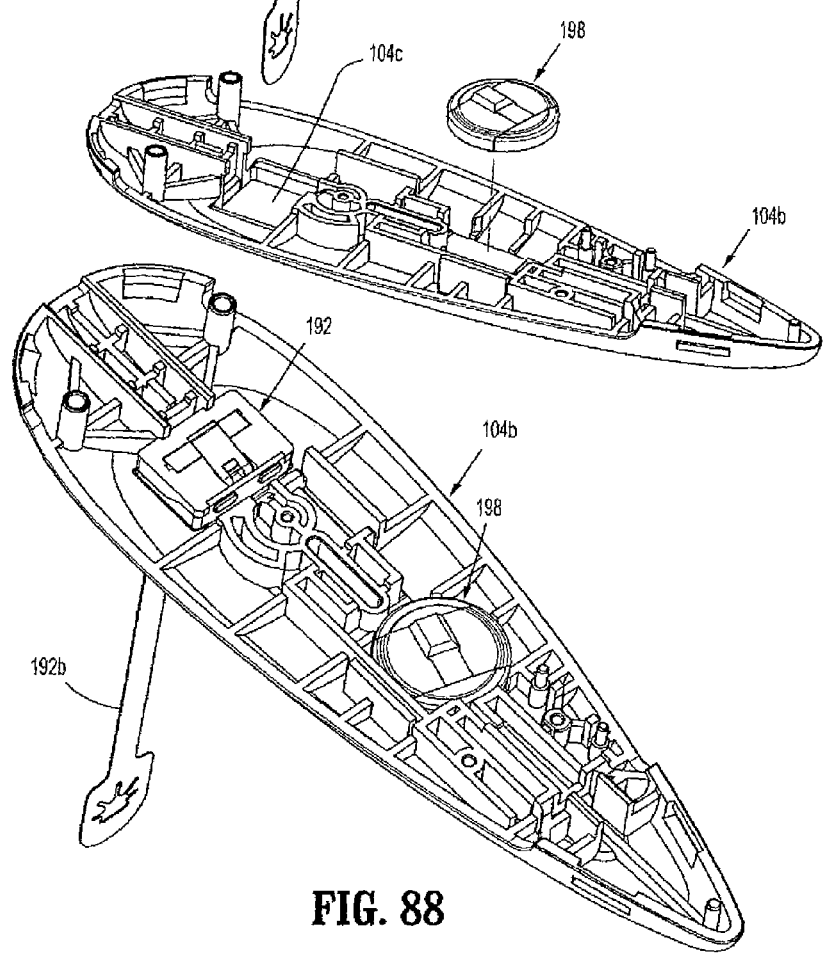
Figure 89:
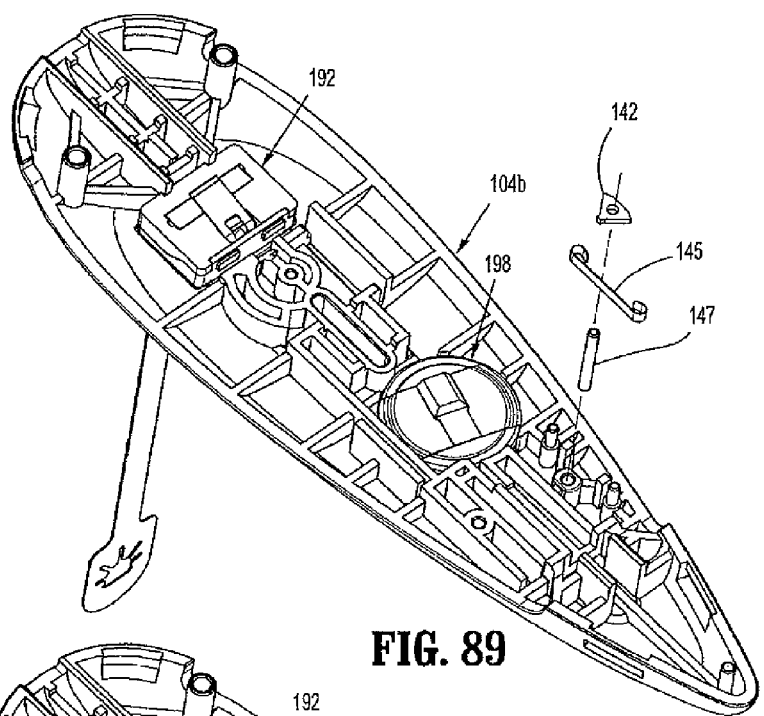
Figure 90:
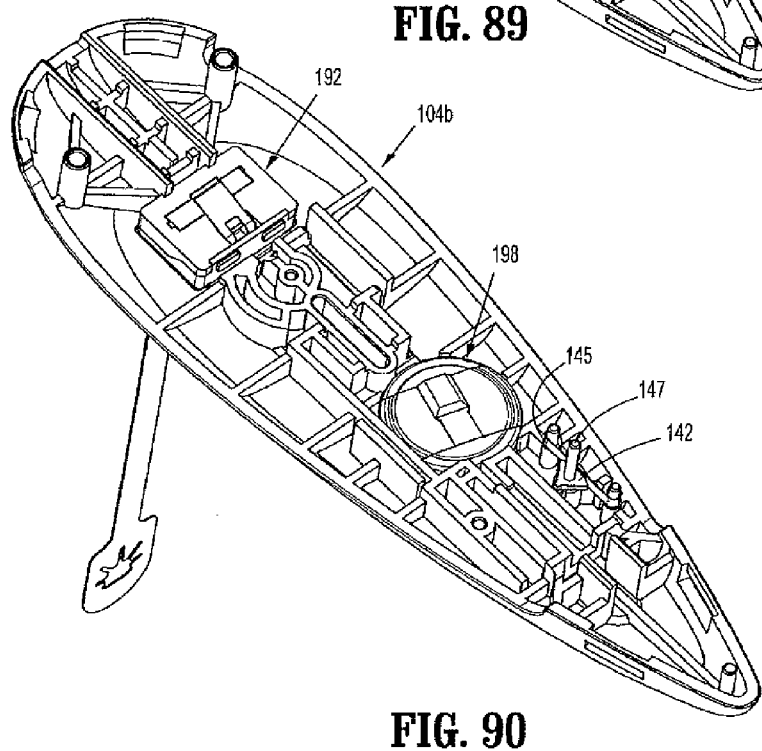

Turning now to FIGS. 87-110, an exemplary method of assembling a relatively small, medium and/or large clip applier 100 is illustrated. As seen in FIGS. 87 and 88, during assembly, a lower housing half 104b is provided and a battery or energy source 198 is seated within lower housing half 104b. Additionally, a processor 192, including a tab 192b, is seated within window 104c of lower housing half 104b such that tab 192b extends outwardly of lower housing half 104b. Either prior to or following placement of processor 192 and battery 198 in lower housing half 104b, pawl spring 145 and pawl pin 147 are secured or inserted into lower housing half 104b, and pawl 142 is inserted over pawl pin 147 and moved into engagement with pawl spring 145.

Figure 91:
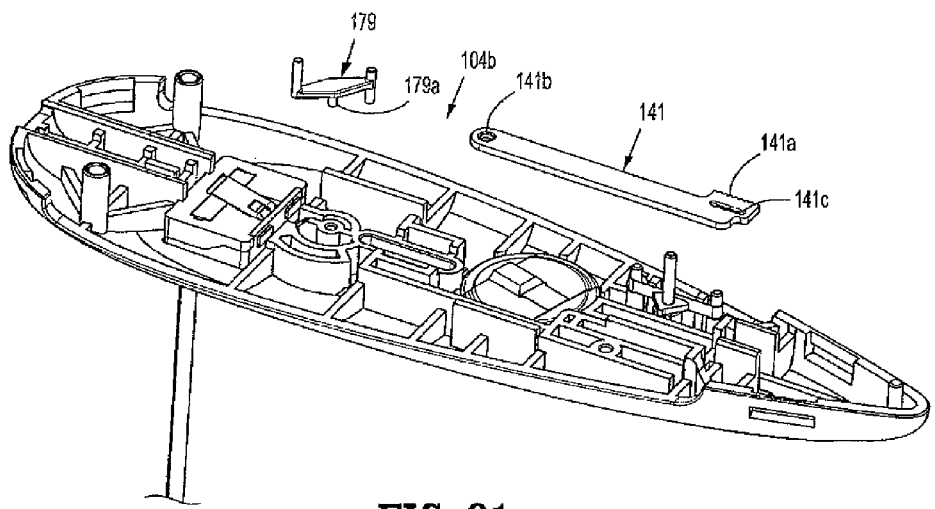
Figure 92:
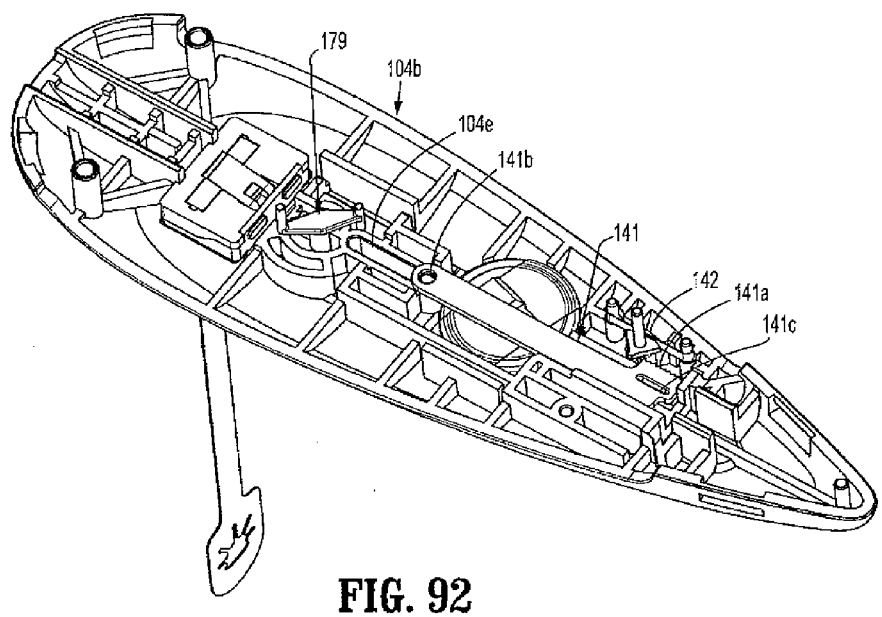

As seen in FIGS. 91 and 92, a correspondingly sized pivot arm 179 (e.g., a pivot arm 179 corresponding in size to a length and/or width of the surgical clips) is pivotally attached or seated into lower housing half 104b via pivot boss 179a. Additionally, as seen in FIGS. 91 and 92, rack member 141 is slidably positioned within lower housing half 104b such that teeth 141a of rack member 141 are operatively associated with the teeth of pawl 142. Additionally, a distal opening 141b of rack member 141 overlies elongate channel 104e defined in lower housing half 104b, and a projection 141c of rack member 141 is slidably positioned within a complementary slot defined by lower housing half 104b.

Figure 93:
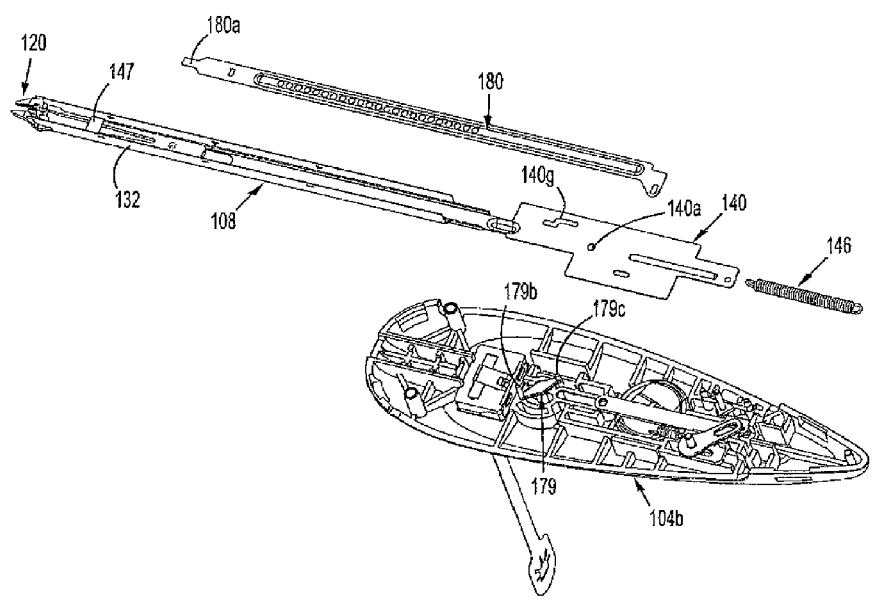
Figure 94:
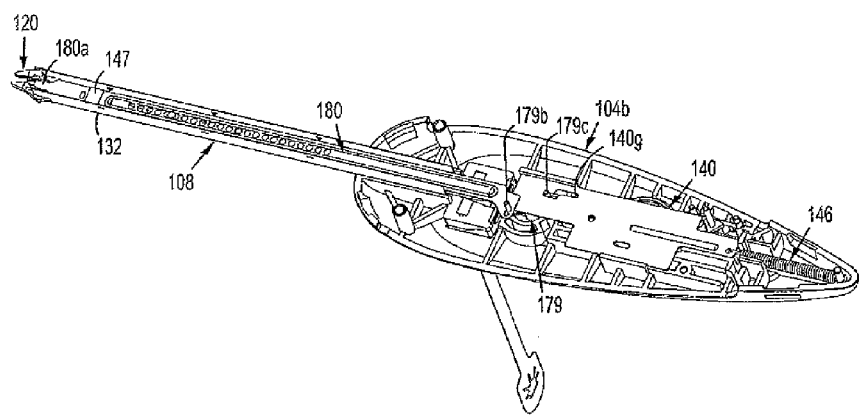

Turning now to FIGS. 93 and 94, a channel assembly 108 is connected to lower housing half 104b. Channel assembly 108 includes a lower channel 132, a drive channel 140 slidably disposed within lower channel 132, jaws 120 fixedly connected to lower channel 132, and channel strap 143 secured near a distal end of drive channel 140. When channel assembly 108 is connected to lower housing half 104b, drive pin recess 140a is aligned with opening 141b of rack member 141. Also, second finger 179c of pivot arm 179 is slidably disposed within window 140g of drive channel 140.

As seen in FIGS. 93 and 94, a correspondingly sized wedge plate 180 (e.g., a wedge plate 180 corresponding in size to a length and/or width of the surgical clips) is slidably positioned over drive channel 140 such that a distal end 180a of wedge plate 180 is interposed between channel strap 143 and jaws 120, and a proximal end of wedge plate 180 is connected to first finger 179b of pivot arm 179.

Additionally, as seen in FIGS. 93 and 94, biasing member 146 is provided and has a first end connected to drive channel 140 and a second end secured to lower housing half 104b.

Figure 95:
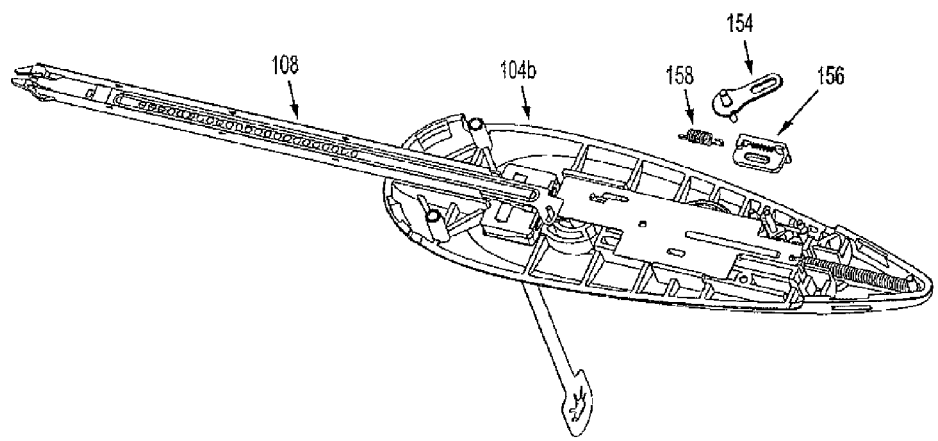
Figure 96:
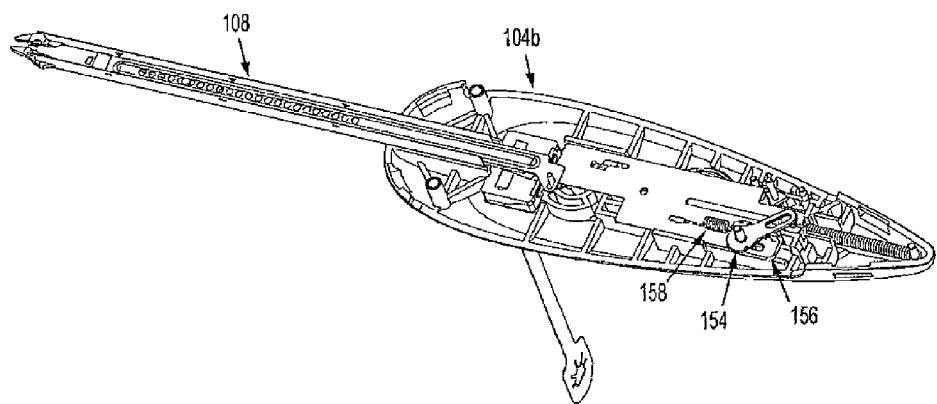

Turning now to FIGS. 95 and 96, an accelerator rack 156 is slidably positioned within lower housing half 104b, and a correspondingly sized bell crank gear 154 (e.g., a bell crank gear 154 corresponding in size to a length and/or width of the surgical clips) pivotally connected to lower housing half 104b via pivot pin 154a, wherein the pivot pin 154a extends through accelerator rack 156. When properly positioned spur gear 154d of bell crank gear 154 engages gear rack 156d of accelerator rack 156. (see FIGS. 4A-4C). A biasing member 158 is provided and interconnected between drive channel 140 and accelerator rack 156.

Figure 97:
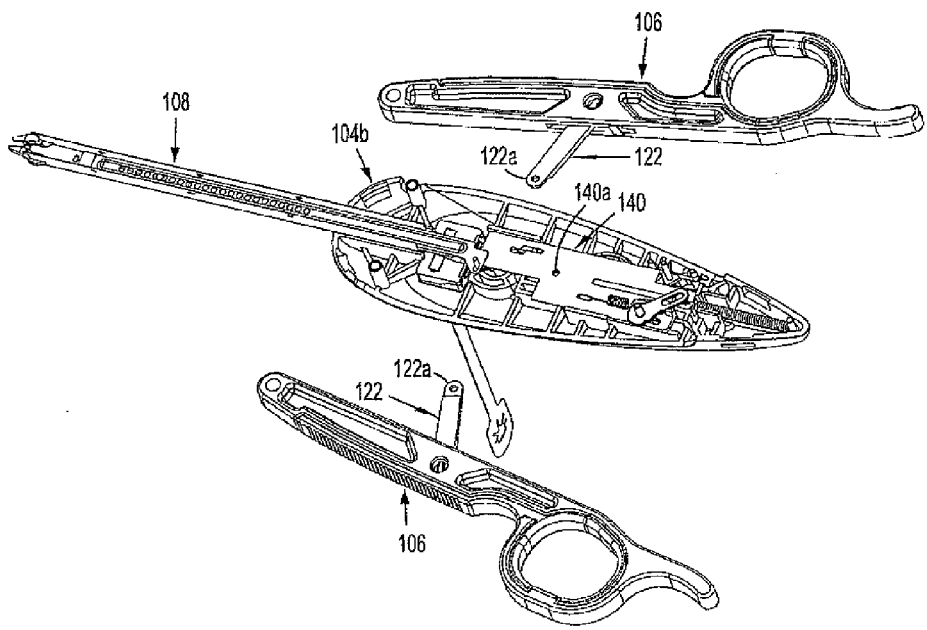
Figure 98:
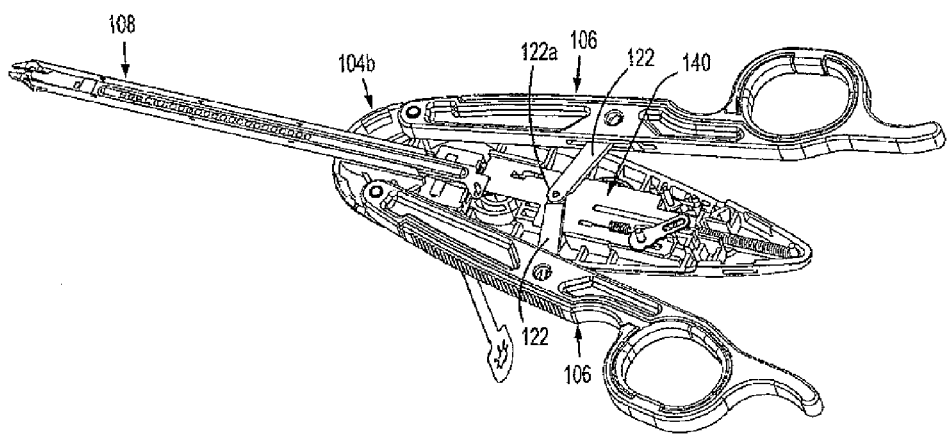

Next, as seen in FIGS. 97 and 98, a pair of handles 106 is connected to lower housing half 104b. In particular, a distal aperture 106a of each handle 106 is pivotally disposed on a respective pivot post 104d of lower housing half 104b. Also, link members 122 are provided which are pivotally connected to a respective handle 106 and extend therefrom such that a distal end 122a thereof overlies pivot point 140a of drive channel 140.

Figure 99:
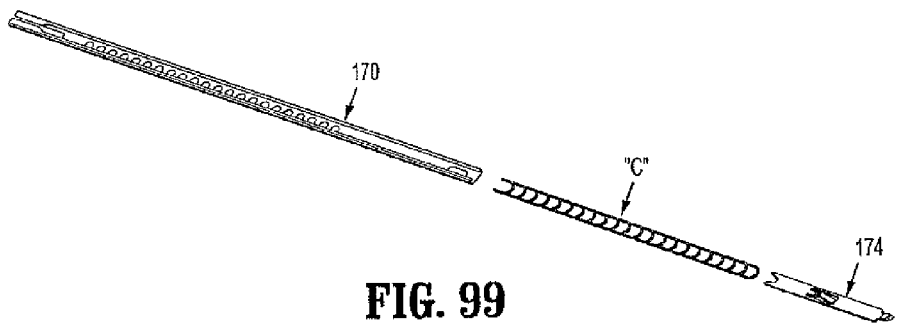
Figure 100:
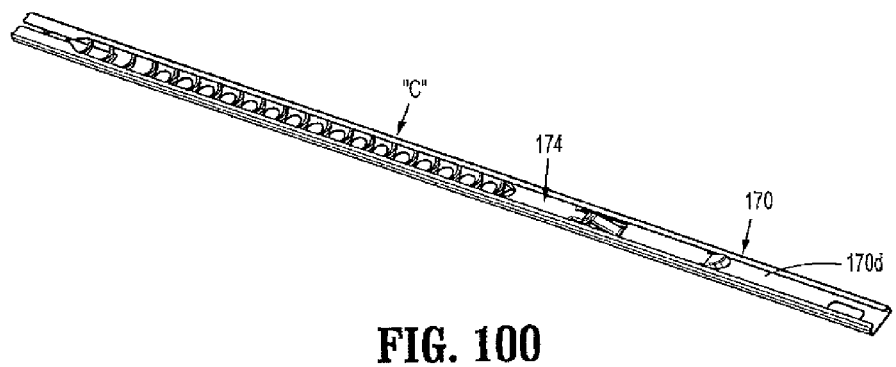

Turning now to FIGS. 99 and 100, either prior to, during or following the preceding steps, a stack of clips "C" is inserted into a channel 170d of a clip carrier 170. Also, a clip follower 174 is placed within channel 170d of clip carrier 170 at a location proximal of the stack of clips "C." In an embodiment, twenty-two clips "C" may be loaded into clip carrier 170. Depending on the size clips "C" (e.g., width and/or length) to be loaded in the clip carrier 170, a correspondingly sized clip carrier 170 and clip follower 174 is provided or selected.

Figure 101:
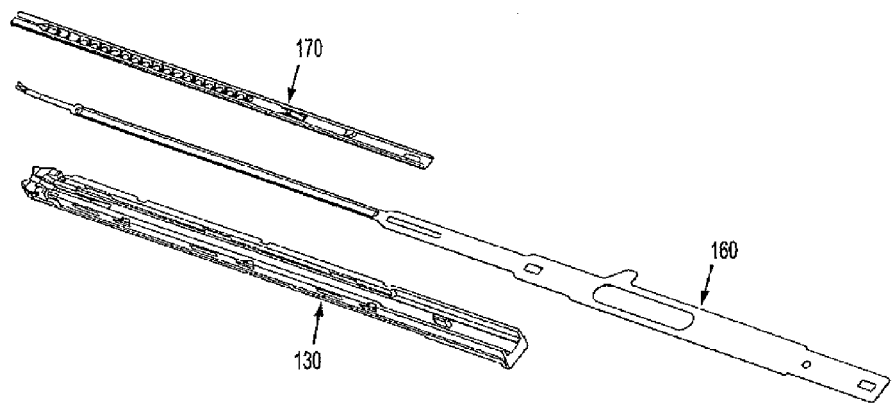
Figure 102:
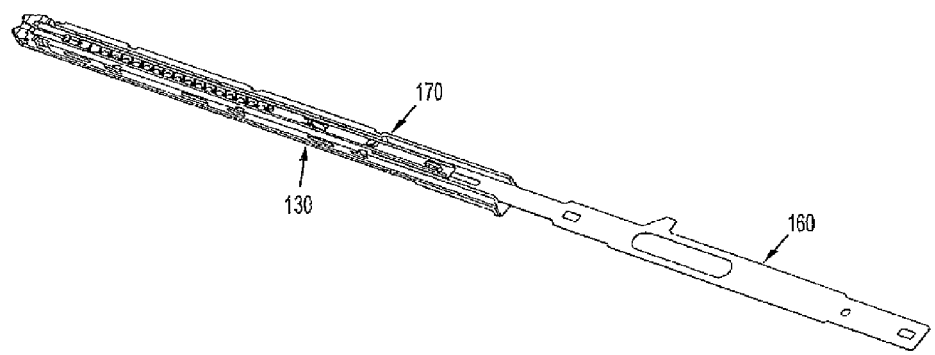

As seen in FIGS. 101 and 102, a correspondingly sized pusher bar 160 (e.g., a pusher bar 160 corresponding in size to a length and/or width of the surgical clips) is slidably disposed in cartridge cover 130, and the loaded clip carrier 170 is fixedly placed within cartridge cover 130 so as to cover a distal end of pusher bar 160.

Figure 103:
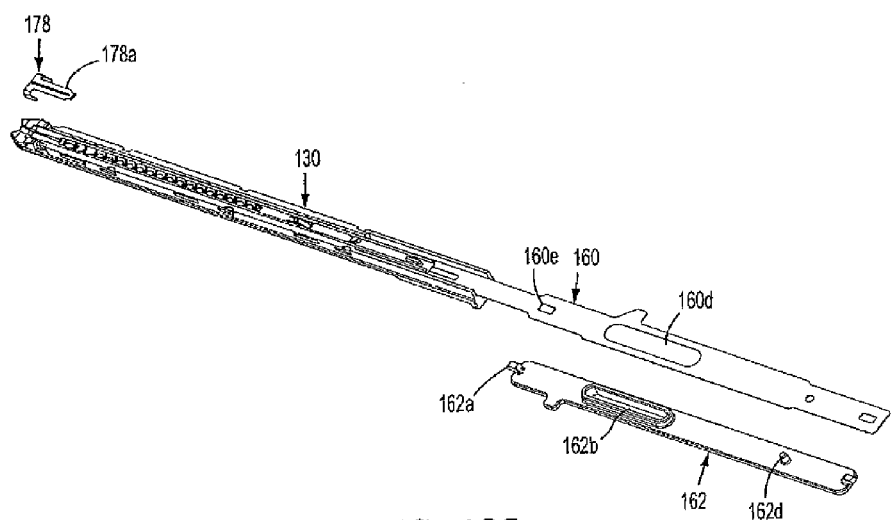
Figure 104:
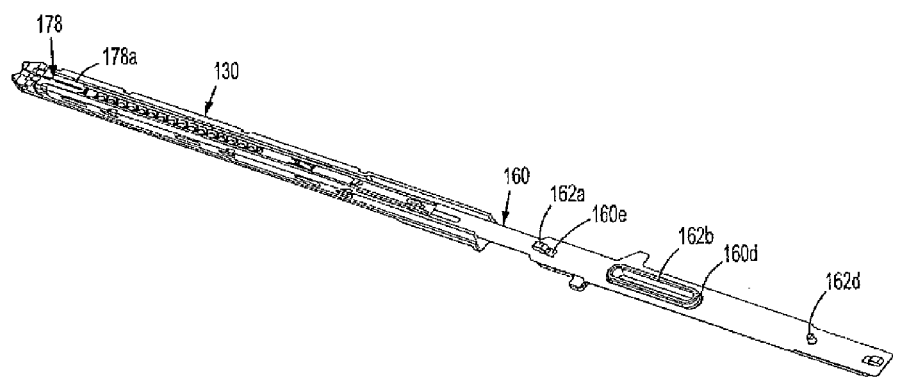

Turning now to FIGS. 103 and 104, a lockout 178 is secured near a distal end of cartridge cover 130. In particular, a tab 178a of lockout 178 is oriented to extend in a proximal direction. Also as seen in FIGS. 103 and 104, a stabilizer 162 is connected to a proximal end of pusher bar 160. In particular, a distal tab 162a of stabilizer 162 is inserted into a distal window 160e of pusher bar 160, and an elongate window 162b of stabilizer 162 is aligned with a proximal window 160d of pusher bar 160. As seen in FIGS. 103 and 104, nub 162d of stabilizer 162 extends through pusher bar 160.

Figure 105:
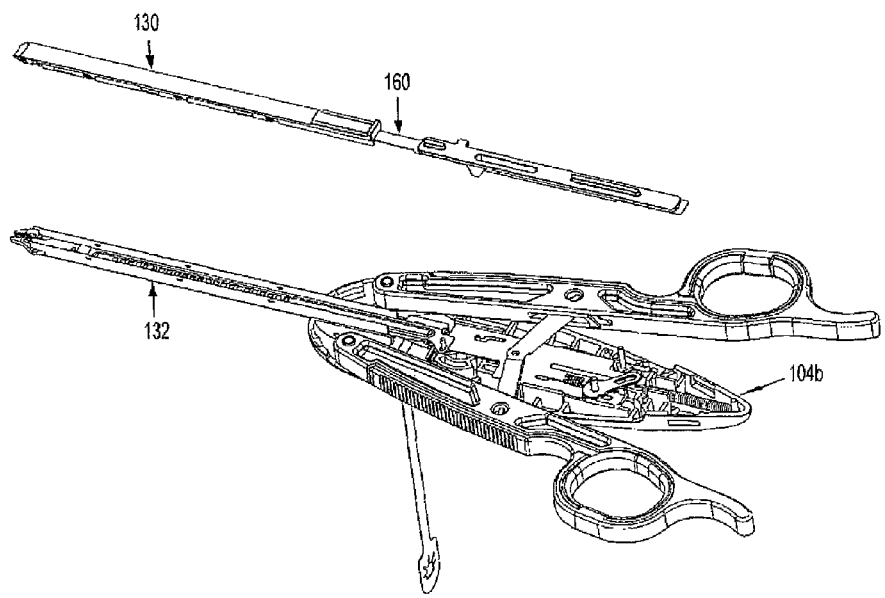
Figure 106:
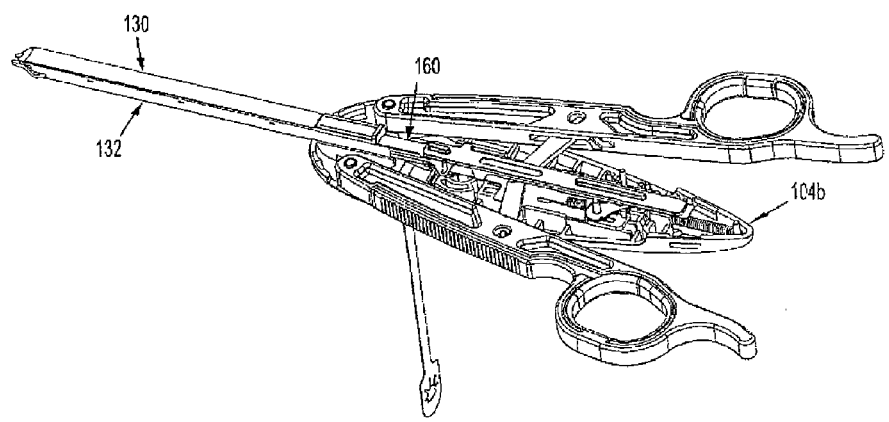

Turning now to FIGS. 105 and 106, with pusher bar 160 a clip carrier 170 connected to cartridge cover 130, cartridge cover 130 is connected to outer channel 132 such that the proximal end of pusher bar 160 overlies lower housing half 104b. In particular, proximal window 160d of pusher bar 160 is positioned over distal end 122a of link members 122 and over pivot point 140a of drive channel 140. When pusher bar 160 is positioned within lower housing half 104b, nub 162d of stabilizer 162 is positioned within slot 154f of arm 154c of bell crank gear 154. (see FIG. 4C).

Figure 107:
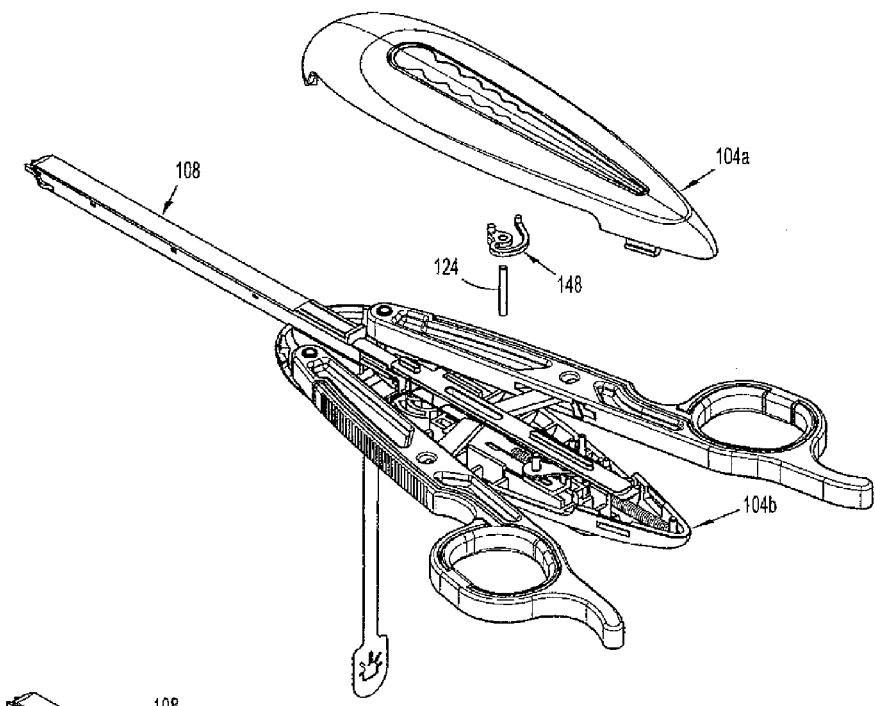
Figure 108:
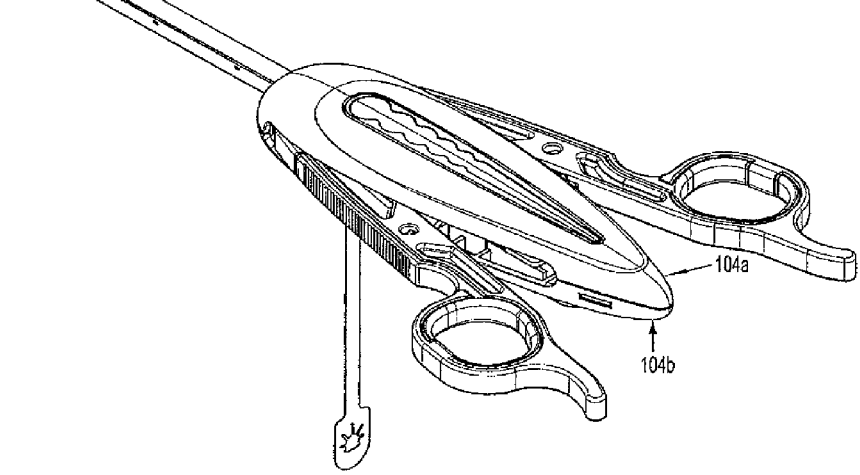

As seen in FIGS. 107 and 108, a drive pin 124 is inserted through proximal window 160d of pusher bar 160, through each distal end 122a of link members 122, through pivot point 140a of drive channel 140 (see FIGS. 97 and 98), through opening 141b of rack member 141 (see FIGS. 91 and 92), and into elongate channel 104e defined in lower housing half 104b (see FIGS. 91 and 92).

With continued reference to FIGS. 107 and 108, an audible/tactile indicator 148 is connected to drive pin 124 so as to move therewith. Next, upper housing half 104a is secured to lower housing half 104b.

Figure 109:
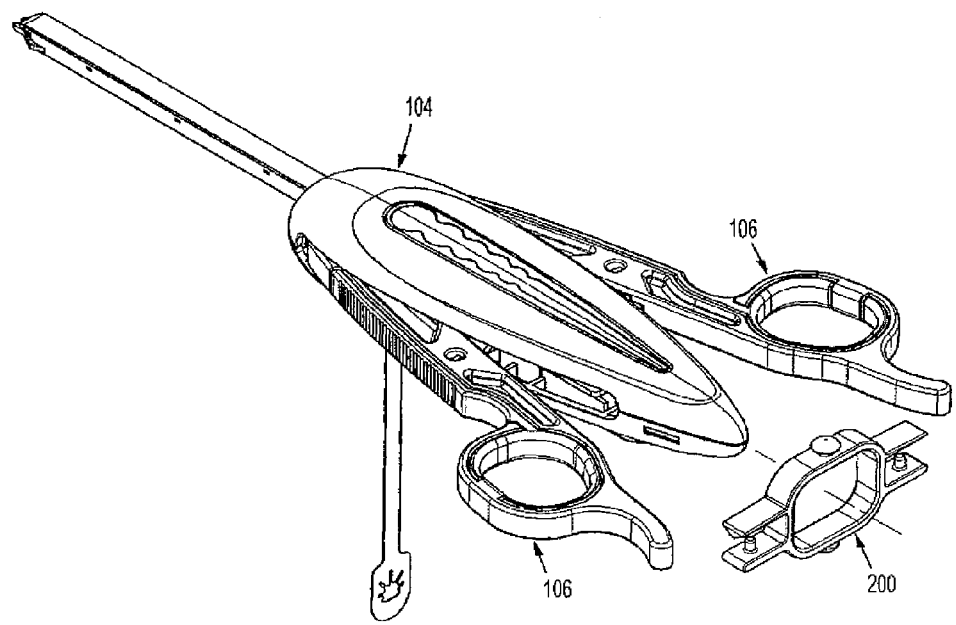
Figure 110:
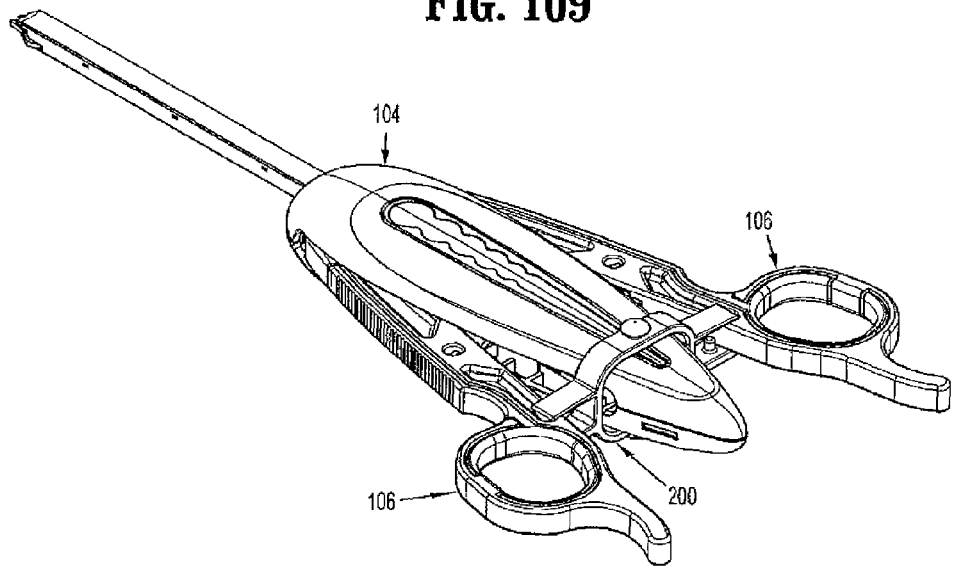

As seen in FIGS. 109 and 110, a shipping wedge 200 is introduced between handles 106 and connected to housing 104. Additionally, a distal or free end of tab 192b is connected to shipping wedge 200 such that upon removal of shipping wedge 200 from housing 104 results in removal of tab 192b and activation of the counter mechanism.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

The invention claimed is:

1. A method of assembling any one of a relatively small scaled surgical clip applier scaled to deliver relatively small surgical clips, a relatively medium scaled surgical clip applier scaled to deliver relatively medium surgical clips, and a relatively large scaled surgical clip applier scaled to deliver relatively large surgical clips, the method comprising the steps of:
   providing a housing for a handle assembly;
   selecting a channel assembly from at least a first channel assembly including a plurality of small surgical clips loaded therein, a second channel assembly including a plurality of medium surgical clips loaded therein, and a third channel assembly including a plurality of large surgical clips loaded therein, wherein each of the first, second and third channel assemblies has an associated stroke length required to load one of the respectively scaled clips into jaws of the clip applier upon firing;
   connecting the selected channel assembly to the housing;
   providing a pusher bar in the selected channel assembly, wherein the pusher bar extends to the handle assembly;
   connecting a motion multiplier system to the pusher bar, the motion multiplier system configured to vary a stroke length of the pusher bar in accordance with the associated stroke length such that, upon firing, the pusher bar is translated the associated stroke length to load one of the respectively scaled clips into jaws of the clip applier, the motion multiplier system including an accelerator rack and a bell crank gear;
   positioning the accelerator rack for slidable disposition within the housing;
   positioning the bell crank gear for pivotable disposition within the housing; and
   engaging the bell crank gear with the accelerator rack such that translation of the accelerator rack effects rotation of the bell crank gear.

2. The method according to claim 1, further comprising the step of selecting a particularly sized pusher bar.

3. The method according to claim 1, further comprising the step of coupling the pusher bar to the bell crank gear such that rotation of the bell crank gear effects translation of the pusher bar.

4. The method according to claim 3, wherein the motion multiplier system varies the rotation of the bell crank gear to thereby vary the stroke length of the pusher bar in accordance with the required stroke length.

5. A method of assembling any one of a relatively small scaled surgical clip applier scaled to deliver relatively small surgical clips, a relatively medium scaled surgical clip applier scaled to deliver relatively medium surgical clips, and a relatively large scaled surgical clip applier, scaled to deliver relatively large surgical clips, the method comprising the steps of:
   providing a housing for a handle assembly;
   selecting a particularly sized channel assembly;
   connecting the particularly sized channel assembly to the housing, wherein the channel assembly includes a plurality of respectively scaled surgical clips loaded therein;
   providing a pusher bar in the channel assembly, wherein the pusher bar extends to the handle assembly; and
   connecting a motion multiplier system to the pusher bar, wherein the motion multiplier system varies a stroke length of the pusher bar upon a firing of one of a relatively small, medium and large scaled clip applier to load the respective small, medium and large clip into jaws of the clip applier.

6. The method according to claim 5, wherein the channel assembly is selected from a first channel assembly including a plurality of small surgical clips loaded therein, a second channel assembly including a plurality of medium surgical clips loaded therein, and a third channel assembly including a plurality of large surgical clips loaded therein.

7. The method according to claim 5, further comprising the step of selecting a particularly sized housing in accordance with the selected particularly sized channel assembly.

8. The method according to claim 5, further comprising the step of selecting a particularly sized pusher bar in accordance with the selected particularly sized channel assembly.

9. The method according to claim 8, wherein the motion multiplier system is connected to the pusher bar such that rotation of motion multiplier system effects translation of the pusher bar.

10. The method according to claim 9, wherein rotation of the motion multiplier system is varied to thereby vary the stroke length of the pusher bar in accordance with a required stroke length of the selected particularly sized channel assembly.

* * * * *